US012778583B2

(12) United States Patent
Choi

(10) Patent No.: US 12,778,583 B2
(45) Date of Patent: Nov. 3, 2026

(54) SURGICAL INSTRUMENT CAPABLE OF REVERSE DRIVE

(71) Applicant: LivsMed Inc., Seongnam-si (KR)

(72) Inventor: Woo Jung Choi, Siheung-si (KR)

(73) Assignee: LivsMed Inc., Seongnam-si (KR)

( * ) Notice: Subject to any disclaimer, the term of this patent is extended or adjusted under 35 U.S.C. 154(b) by 0 days.

(21) Appl. No.: 19/003,336

(22) Filed: Dec. 27, 2024

(65) Prior Publication Data

US 2026/0102159 A1 Apr. 16, 2026

(30) Foreign Application Priority Data

Oct. 14, 2024 (KR) ........................ 10-2024-0139229

(51) Int. Cl.
*A61B 17/072* (2006.01)
*A61B 17/00* (2006.01)

(52) U.S. Cl.
CPC .................. *A61B 17/07207* (2013.01); *A61B 2017/00367* (2013.01)

(58) Field of Classification Search
CPC .... A61B 17/07207; A61B 2017/00367; A61B 2017/00398; A61B 2017/00323; A61B 34/71; A61B 2034/715
USPC ...................................................... 227/176.1
See application file for complete search history.

(56) References Cited

U.S. PATENT DOCUMENTS

| | | | | |
|---|---|---|---|---|
| 7,604,150 | B2 | 10/2009 | Boudreaux | |
| 10,022,194 | B2 | 7/2018 | Prisco | |
| 10,799,239 | B2 * | 10/2020 | Nicholas | A61B 34/71 |
| 2016/0166253 | A1 * | 6/2016 | Knodel | A61B 17/07207 227/175.1 |
| 2017/0265865 | A1 * | 9/2017 | Burbank | A61B 90/361 |
| 2018/0049836 | A1 * | 2/2018 | Shelton, IV | A61B 17/00234 |
| 2020/0405403 | A1 * | 12/2020 | Shelton, IV | A61B 17/3421 |
| 2022/0031351 | A1 * | 2/2022 | Moubarak | A61B 17/0686 |
| 2022/0096067 | A1 * | 3/2022 | Beckman | A61B 17/00 |
| 2023/0045998 | A1 * | 2/2023 | Shelton, IV | A61B 17/07207 |
| 2025/0250474 | A1 * | 8/2025 | Li | C09K 5/063 |

OTHER PUBLICATIONS

Office Action issued in KR 10-2024-0139229; mailed by the Korean Intellectual Property Office on Aug. 21, 2026.

* cited by examiner

*Primary Examiner* — Linda J. Hodge
(74) *Attorney, Agent, or Firm* — Studebaker Brackett PLLC

(57) ABSTRACT

Provided is a surgical instrument capable of reverse drive. The surgical instrument includes: an end tool having at least one driving element activated by a wire; a power transmission unit that controls a linear movement of the wire based on a rotational movement of a conversion element in accordance with power from an actuator; and a shaft connecting the end tool and the power transmission unit. The surgical instrument is configured so that both forward drive in which the driving element is activated according to activation of the actuator and the reverse drive in which the conversion element is activated according to activation of the driving element due to an external force are possible.

17 Claims, 59 Drawing Sheets

3101t1 } 3101t
3101t2

3111 } 3110
3112

Forward-Drive

Back-Drive

SURGICAL INSTRUMENT CAPABLE OF REVERSE DRIVE

CROSS-REFERENCE TO RELATED APPLICATION

This application is based on and claims priority under 35 U.S. C. § 119 to Korean Patent Application No. 10-2024-0139229, filed on Oct. 14, 2024, in the Korean Intellectual Property Office, the disclosure of which is incorporated by reference herein in its entirety.

BACKGROUND

1. Field

The present disclosure relates to a medical device, and more specifically, but not limitedly, to a surgical instrument capable of reverse drive.

2. Description of the Related Art

In recent years, laparoscopic surgery has been actively utilized to reduce postoperative recovery time and complications through small incisions. The laparoscopic surgery is a surgical method in which small holes are drilled in the abdomen of a patient and the inside of the abdominal cavity is observed through these holes, and is widely used in general surgery and the like.

In performing the laparoscopic surgery, various instruments are used. For example, a suturing instrument inserted into the body is used to suture a surgical site in the abdominal cavity, and a surgical stapler for suturing the surgical site using medical staples is utilized as the suturing instrument.

In general, a surgical stapler is a medical apparatus that is often used for cutting and anastomosis of an organ in abdominal and thoracic surgery. The surgical stapler includes an open stapler used in thoracotomy or laparotomy and an endo stapler used in thoracoscopic surgery and celioscopic surgery.

The surgical stapler has advantages of not only shortening surgery time since cutting of a surgical site and anastomosis of an organ are simultaneously performed, but also accurately suturing the surgical site. Moreover, the surgical stapler has advantages of a faster recovery and a smaller scar than those when tissue is cut and sutured using a surgical suture thread, and thus has been widely used in modern invasive surgeries. In particular, the surgical stapler has been widely used in cancer surgery to cut cancer tissue and suture a cut site.

A surgical instrument including a stapler may operate based on power from an actuator. However, in the case of the conventional surgical instrument including the stapler, when the power of the actuator is not transmitted to an end tool due to various reasons, a working member such as an articulation or a blade of the stapler may not be manipulated. Accordingly, when the power supply to the actuator is interrupted during laparoscopic surgery, it is inevitable to switch over to laparotomic surgery.

SUMMARY

An exemplary aspect of the present disclosure is directed to providing a surgical instrument capable of controlling a driving element as intended even in a state where the power transmission between an actuator and a conversion element is decoupled by enabling reverse drive in which the conversion element of a power transmission unit is activated by activating at least one driving element provided on an end tool of the surgical instrument by an external force.

The aspects of the present disclosure are not limited to those mentioned above, and other aspects and benefits not mentioned herein will be understood from the following description and will become apparent from the embodiments of the present disclosure. It is also to be understood that the aspects and benefits of the present disclosure may be realized by means and combinations thereof set forth in the claims.

The surgical instrument capable of the reverse drive according to an embodiment of the present disclosure may include: an end tool having at least one driving element activated by a wire; a power transmission unit that controls a linear movement of the wire based on a rotational movement of a conversion element in accordance with power from an actuator; and a shaft connecting the end tool and the power transmission unit, and may be configured so that both forward drive in which the driving element is activated according to activation of the actuator and the reverse drive in which the conversion element is activated according to activation of the driving element due to an external force are possible.

According to an aspect, the wire may include: a first wire that moves backward in a direction away from a distal unit of the end tool to activate the driving element in a first direction; and a second wire that moves forward toward the distal unit of the end tool to activate the driving element in the first direction.

According to an aspect, the first wire, at least a portion of the driving element, the second wire, and the conversion element may form a closed loop.

According to an aspect, when the driving element is activated in the first direction according to the forward drive, tension of the first wire increases and tension of the second wire decreases, and when the driving element is activated in the first direction according to the reverse drive, the tension of the first wire decreases and the tension of the second wire increases.

According to an aspect, conversion efficiency between the rotational movement of the conversion element and the linear movement of the wire according to the forward drive may be configured to be substantially the same as the conversion efficiency between the linear movement of the wire and the rotational movement of the conversion element according to the reverse drive.

According to an aspect, the reverse drive may be performed in a state where power transmission between the conversion element and the actuator is decoupled.

According to an aspect, the state where the power transmission is decoupled may include at least one of: a state where the conversion element and the actuator are physically spaced; or a state where the power of the actuator is not transmitted to the conversion element due to a failure of the actuator or a discharge of a power supply unit.

According to an aspect, the actuator may be activated by the surgical instrument being driven in a reverse direction in a state where the conversion element and the actuator are not physically spaced apart from each other.

According to an aspect, the end tool includes a plurality of driving elements including a first driving element and a second driving element, and the power transmission unit includes a plurality of conversion elements including a first conversion element corresponding to the first driving element and a second conversion element corresponding to the second driving element, wherein the first conversion element and the second conversion element may be activated in response to one of the plurality of driving elements being driven in the reverse direction.

According to an aspect, the surgical instrument may further include at least one auxiliary pulley disposed between the conversion element and the driving element to support the wire.

According to an aspect, there may be further included a support element that contacts at least one of the conversion element or the auxiliary pulley to provide a frictional force for rotation of at least one of the conversion element or the auxiliary pulley.

According to an aspect, the support element may be configured to prevent unintentional reverse drive of the driving element due to gravity.

According to an aspect, in a state where the conversion element and the activator are coupled, the support element may be spaced apart from at least one of the conversion element or the auxiliary pulley, and in response to decoupling of the conversion element and the activator, the support element may be configured to contact at least one of the conversion element or the auxiliary pulley.

According to an aspect, the driving element may include at least one articulation or at least one of a pair of jaws that rotate within a predetermined angular range according to the linear movement of the wire.

According to an aspect, at least one of the at least one articulation or the pair of jaws may be configured to rotate toward an extension direction of the shaft by being driven in the reverse direction by an end tool insertion guide member when the end tool is removed from the inside of the body, even when the power transmission between the conversion element and the actuator is decoupled while being rotated at a predetermined angle with respect to the extension direction of the shaft inside a surgical target body.

According to an aspect, the surgical instrument may be a stapler having a staple cartridge in the end tool, and the driving element may include a working member that moves forward toward the distal unit of the end tool or moves backward away from the distal unit of the end tool according to the linear movement of the wire.

According to an aspect, the wire may include: a backward wire that moves the working member backward away from the distal unit of the end tool; and a forward wire that moves the working member forward toward the distal unit of the end tool.

According to an aspect, the surgical instrument may further include a protruding member connected to the working member for the reverse drive of the working member and protruding outward from the surgical instrument.

According to an aspect, the protruding member may be configured to be disposed farther from the distal unit of the end tool than the working member so that the end tool is located outside the body while being inserted into the surgical target body, and may be connected to the working member through a flexible extension member.

According to an aspect, the surgical instrument may be a hand-held device, and the surgical instrument may further include a manipulation unit having the actuator and a handle unit and coupled to the power transmission unit.

According to the surgical instrument capable of the reverse drive according to an embodiment of the present disclosure described above, even in an emergency situation where the power transmission of the actuator is interrupted in a situation where the end tool is manipulated inside the body during laparoscopic surgery, as an example, it is possible to control at least one driving element of the end tool by an external force. Accordingly, for example, in the process of moving the end tool out of the body, the articulation of the end tool may be rotated by a trocar for guiding the surgical instrument or body cavity, so that the end tool may be safely taken out of the body. Alternatively, for example, by moving the working member of the stapler on which the blade is mounted by an external force, it is possible to decouple the body tissue that was bitten by the pair of jaws from the end tool.

The benefits of the present disclosure are not limited to those mentioned above, and other benefits not mentioned may be clearly understood by those skilled in the art from the following description.

DETAILED DESCRIPTION

Figure 1:
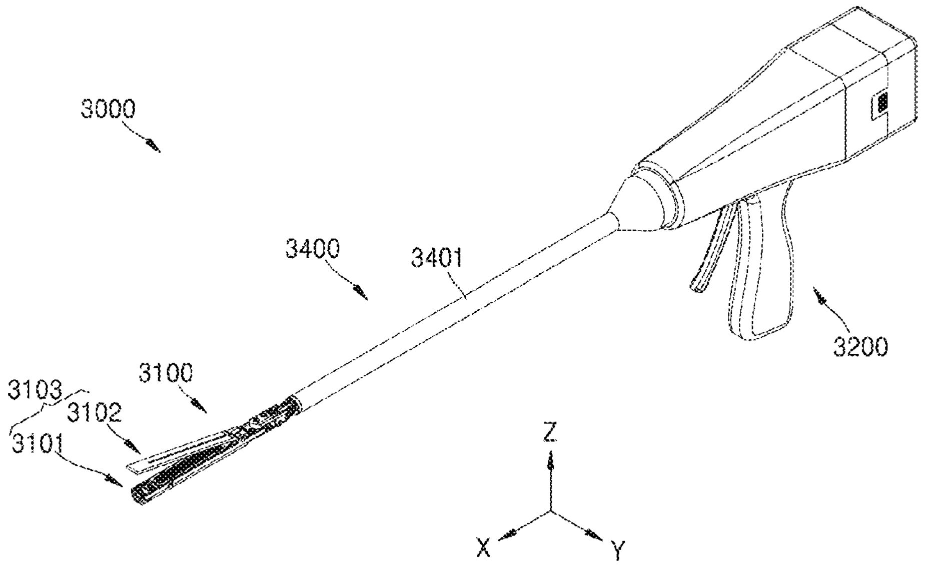
FIG. 1 is a schematic perspective view of a surgical instrument according to an embodiment of the present disclosure.

Hereinafter, various embodiments of the present disclosure are described in conjunction with the accompanying drawings. Various embodiments of the present disclosure may make various changes and have various embodiments, and specific embodiments are illustrated in the drawings and related detailed descriptions are described. However, this is not intended to limit the various embodiments of the present disclosure to specific embodiments, and should be understood to include all changes and/or equivalents or substitutes included in the spirit and technical scope of the various embodiments of the present disclosure. In connection with the description of the drawings, similar reference numerals are used for similar components.

Expressions such as "comprise" or "may comprise" that may be used in various embodiments of the present disclosure indicate the presence of the corresponding function, operation, or component disclosed, and do not limit one or more additional functions, operations, or components. In addition, in various embodiments of the present disclosure, terms such as "comprise" or "have" are used to specify the presence of stated features, integers, steps, operations, components, parts, or a combination thereof, but do not preclude the presence or addition of one or more other features, integers, steps, operations, components, parts, or combinations thereof.

In various embodiments of the present disclosure, the expression such as "or" includes any and all combinations of words listed together. For example, "A or B" may include A, B, or both A and B.

Although the expressions such as "first," "second," etc. used in various embodiments of the present disclosure may modify various components of the various embodiments, they do not limit the components. For example, the expressions do not limit the order and/or importance of corresponding components. These expressions may be used to distinguish one component from the other components. For example, a first user device and a second user device are both user devices and represent different user devices. For example, a first component may be referred to as a second component without departing from the scope of right of various embodiments of the present disclosure, and similarly, the second component may also be referred to as the first component.

In an embodiment of the present disclosure, terms such as "module," "unit," or "part" are used to refer to components that perform at least one function or operation, and these components may be implemented as hardware or software, or as a combination of hardware and software. In addition, a plurality of "modules," "units," "parts," etc. may be integrated into at least one module or chip and implemented with at least one processor, except in the cases where each thereof needs to be implemented with individual specific hardware.

Terms used in various embodiments of the present disclosure are merely used to describe specific embodiments and are not intended to limit the various embodiments of the present disclosure. A singular expression includes a plural expression, unless the context clearly states otherwise.

Unless otherwise defined, all terms including technical and scientific terms used herein have the same meaning as commonly understood by those having ordinary skill in the art to which various embodiments of the present disclosure pertains.

It will be further understood that terms, such as those defined in commonly used dictionaries, should be interpreted as having a meaning that is consistent with their meaning in the context of the relevant art and will not be interpreted in an idealized or overly formal sense unless expressly so defined in various embodiments of the present disclosure.

Hereinafter, various embodiments of the present disclosure will be described in detail using the accompanying drawings.

Surgical Instrument—End Tool

Figure 2:
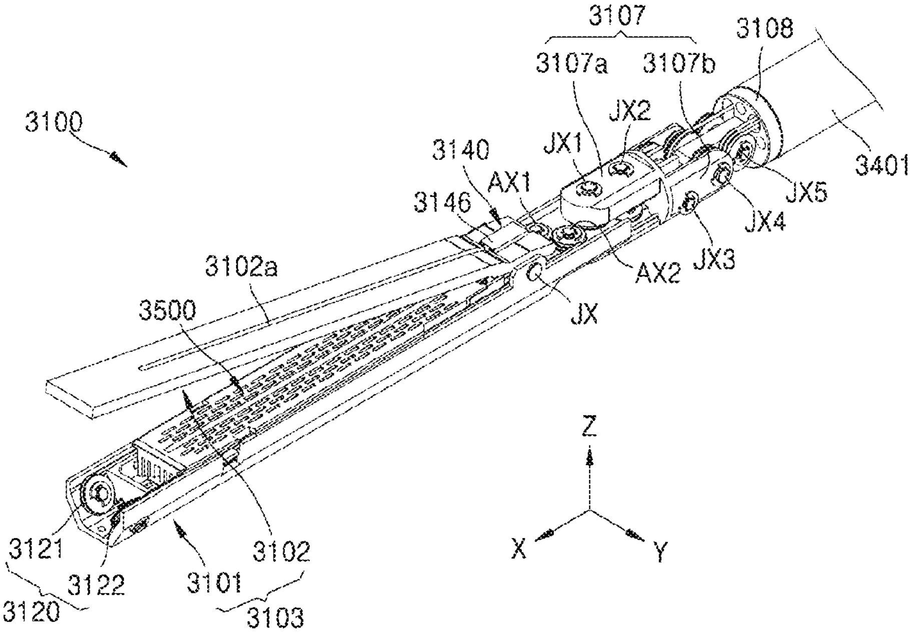
FIG. 2 is a schematic perspective view of the end tool of FIG. 1.
Figure 3:
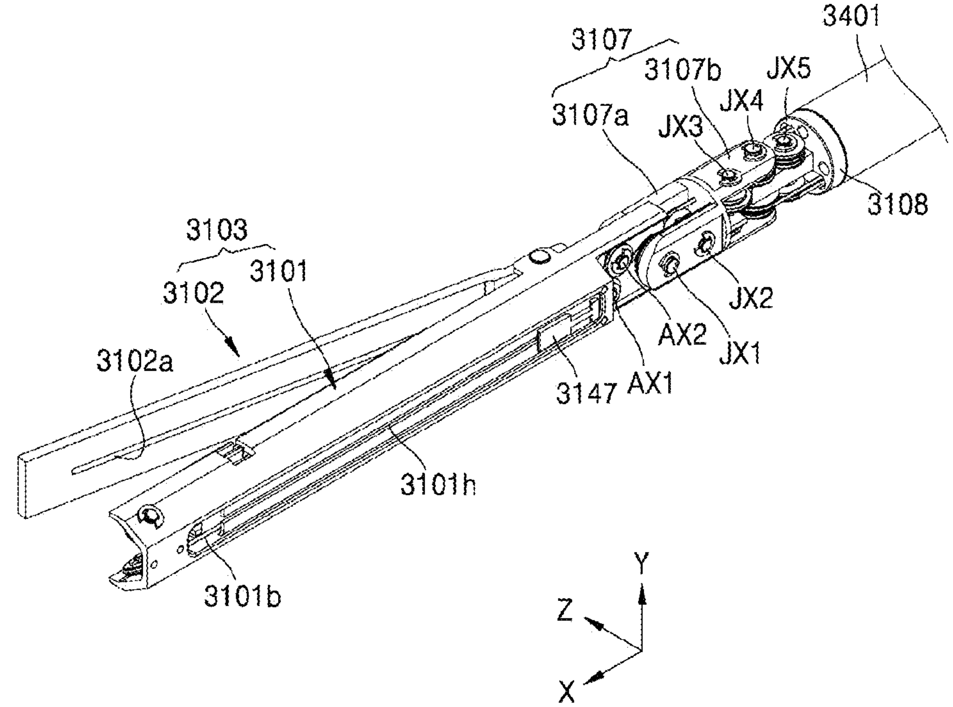
FIG. 3 is a perspective view of the end tool of FIG. 2 as seen from a different angle.
Figure 4:
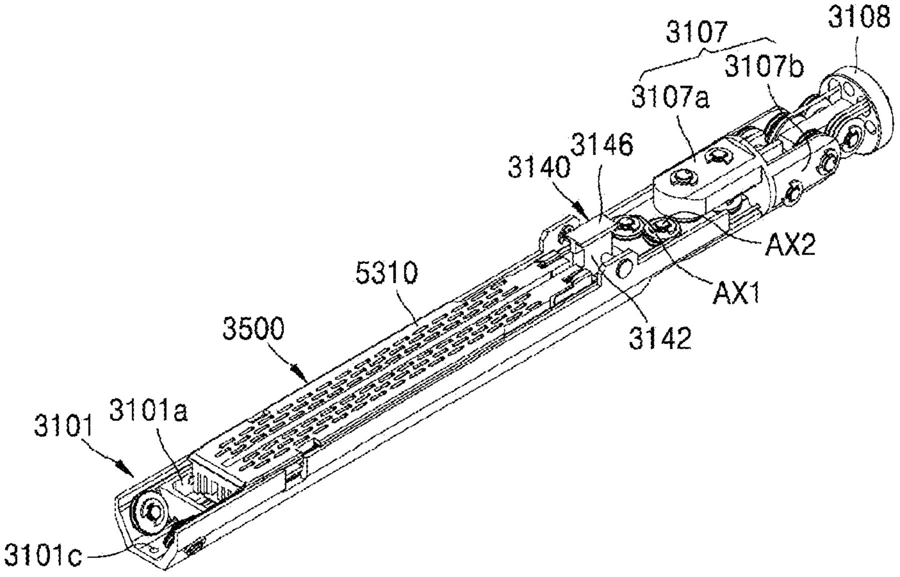
FIG. 4 is a schematic perspective view of the end tool of FIG. 50 with a second jaw removed.
Figure 5:
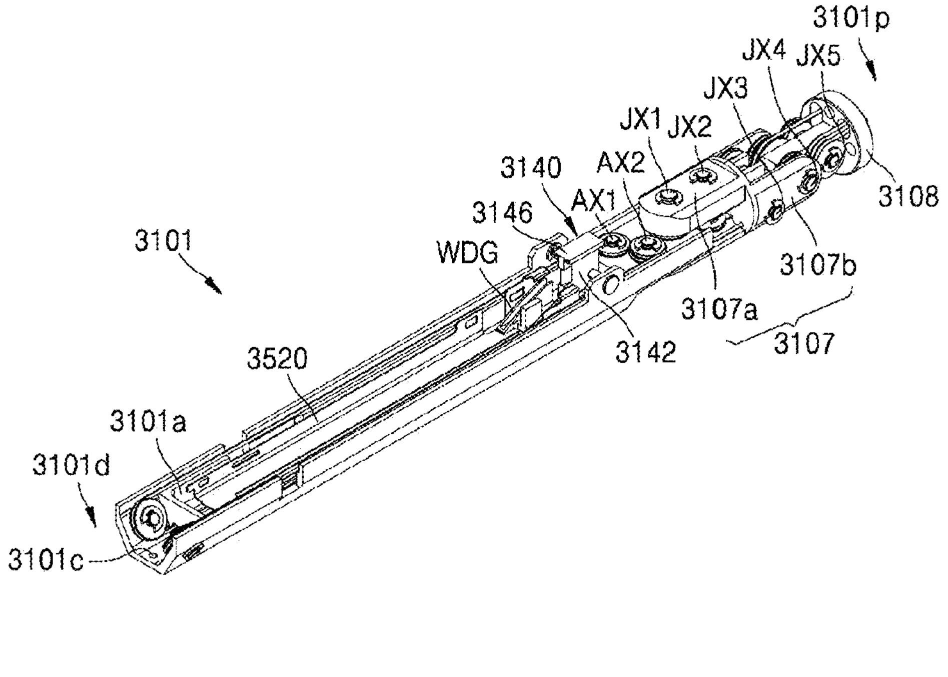
FIG. 5 is a schematic perspective view of the end tool of FIG. 4 with a cartridge removed.
Figure 6:
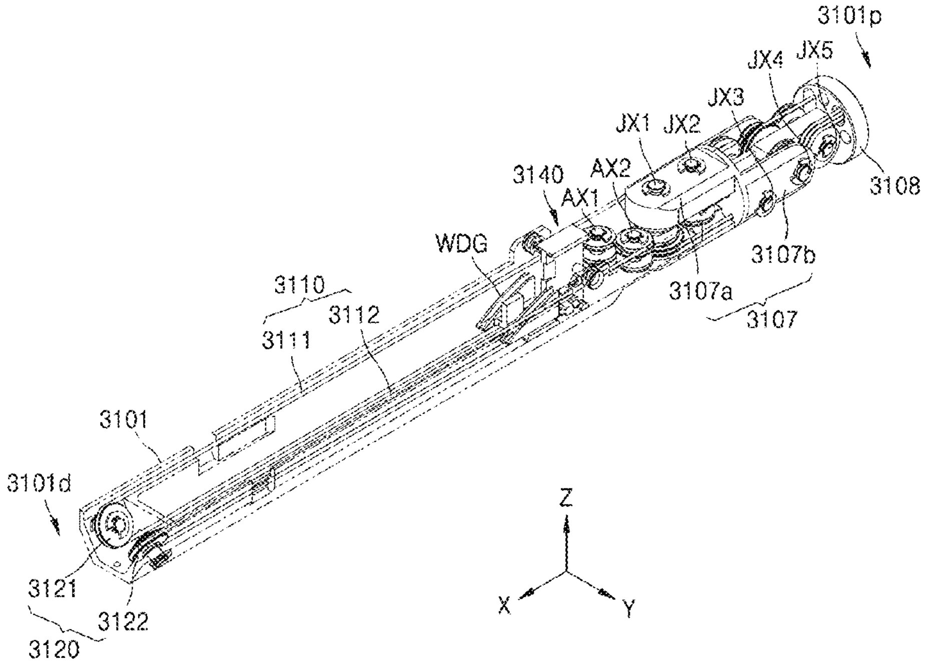
FIG. 6 is a transparent perspective view of FIG. 5.
Figure 7:
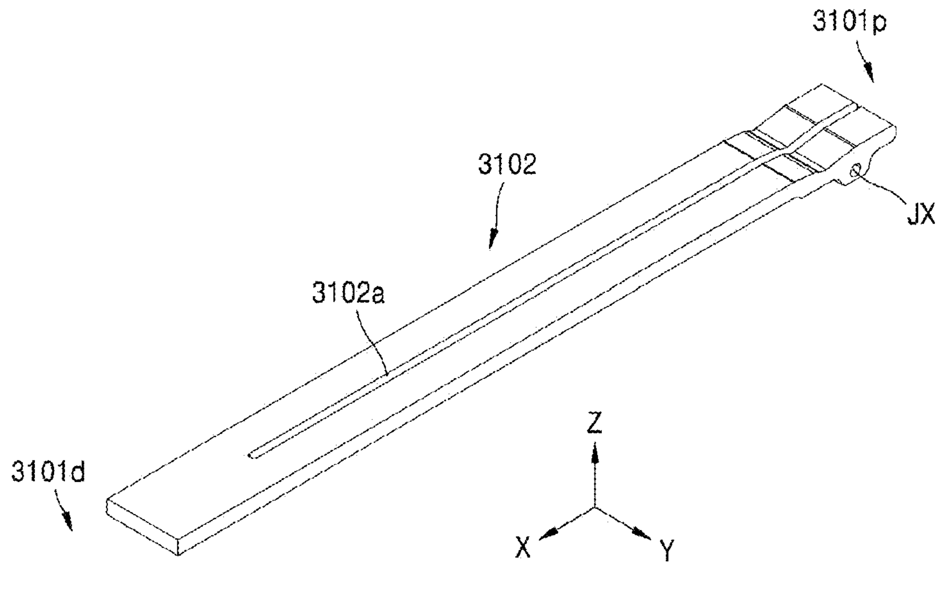
FIG. 7 is a schematic perspective view of the second jaw of the end tool of FIG. 1.
Figure 8:
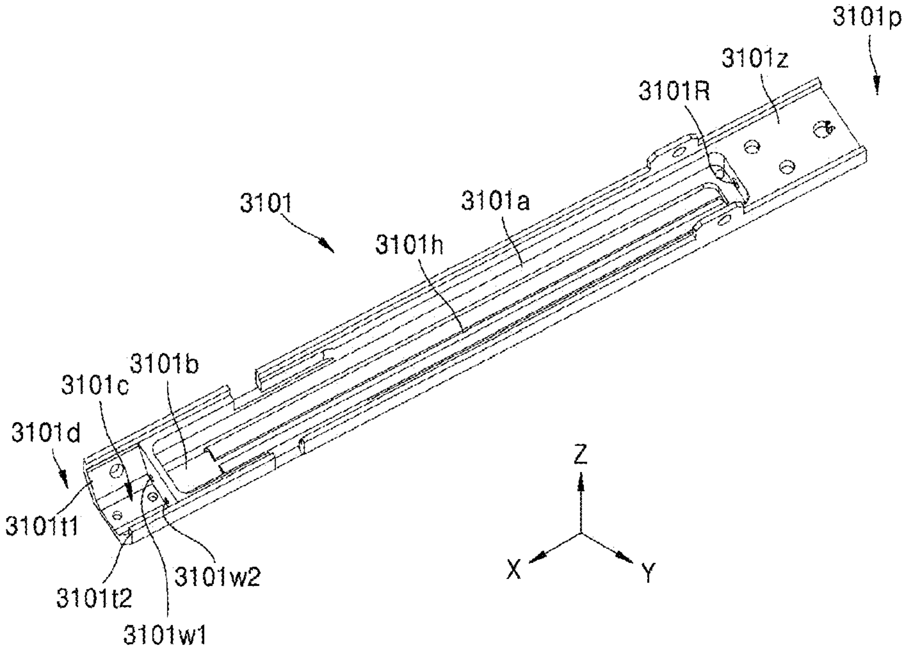
FIG. 8 is a schematic perspective view of a first jaw of the end tool of FIG. 1.
Figure 9:
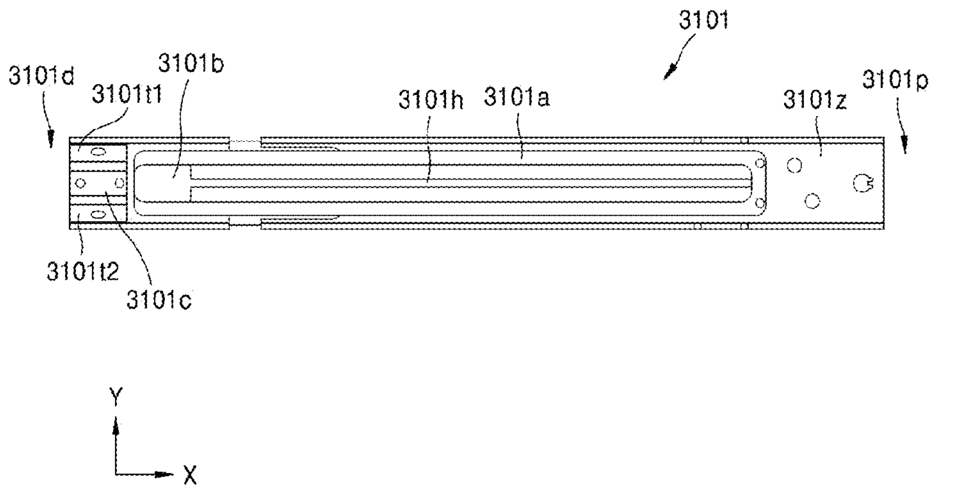
FIG. 9 is a schematic plan view of the first jaw of the end tool of FIG. 1.
Figure 10:
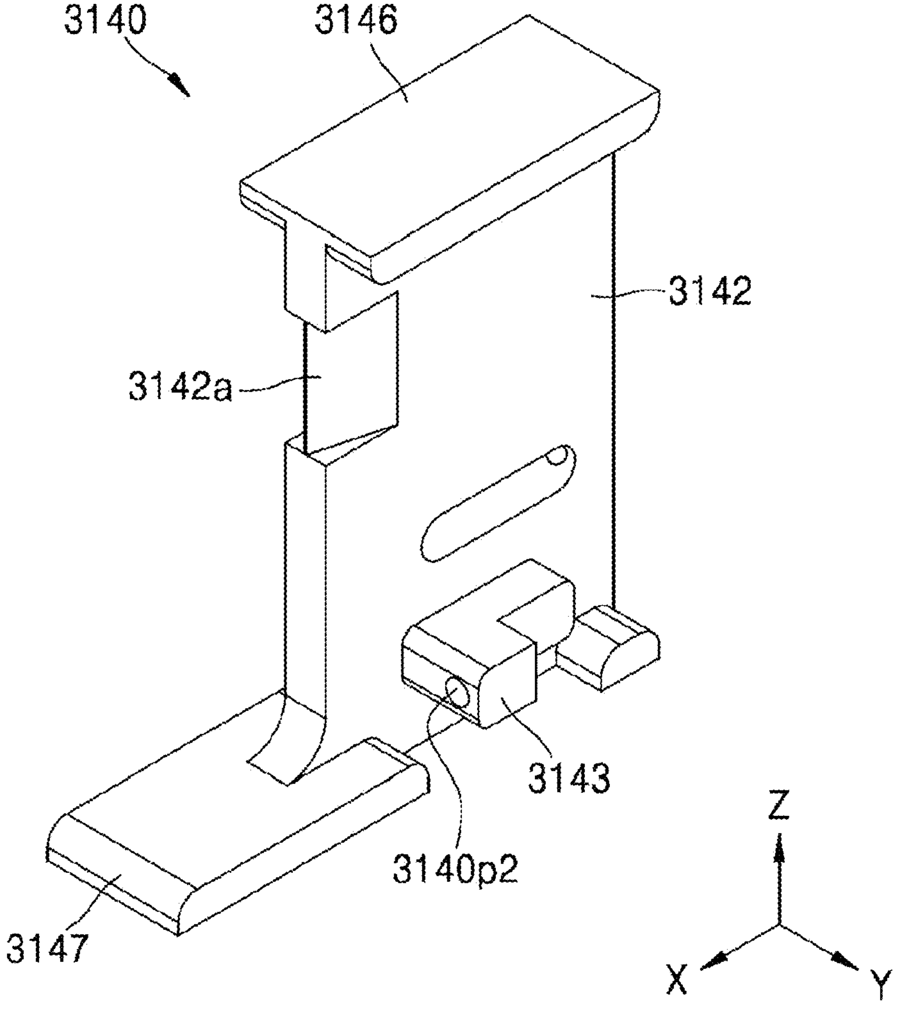
FIG. 10 is a perspective view of the working member of the end tool of FIG. 1.
Figure 11:
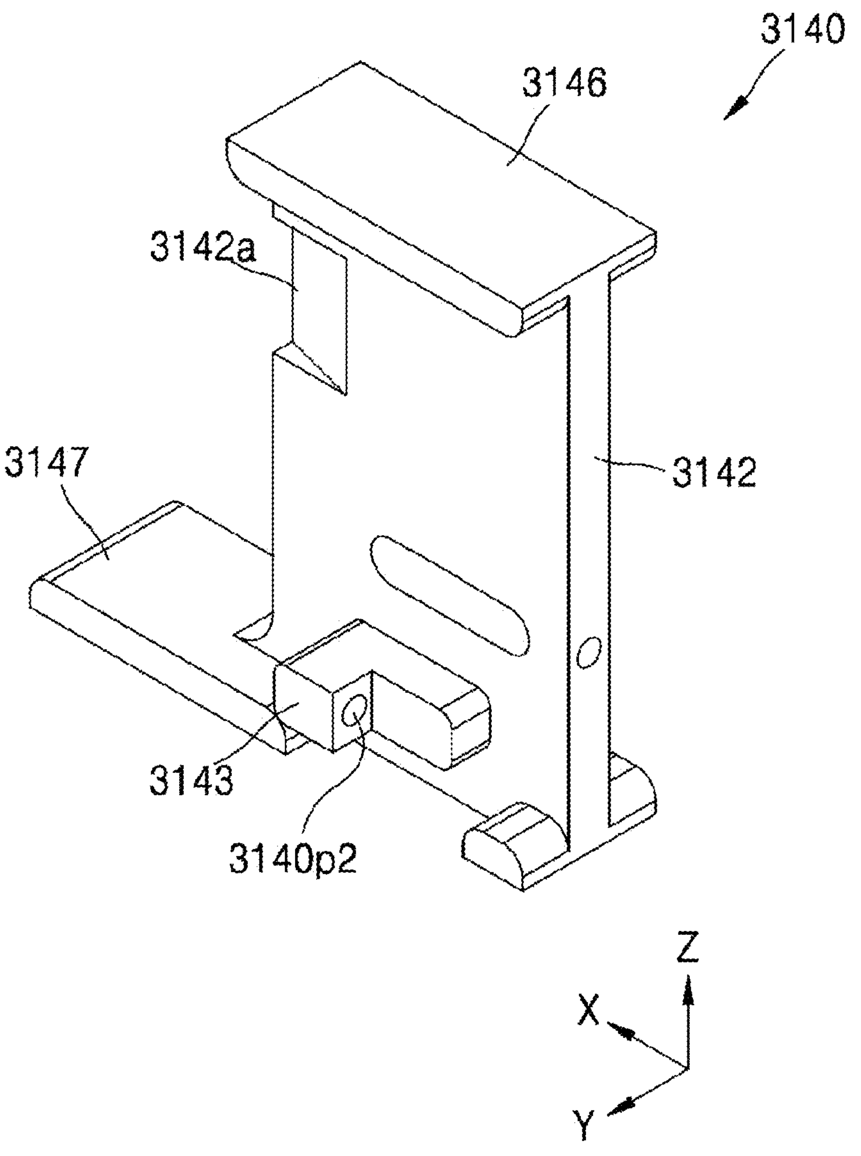
FIG. 11 is a perspective view of the working member of FIG. 10 as seen from a different angle.
Figure 12:
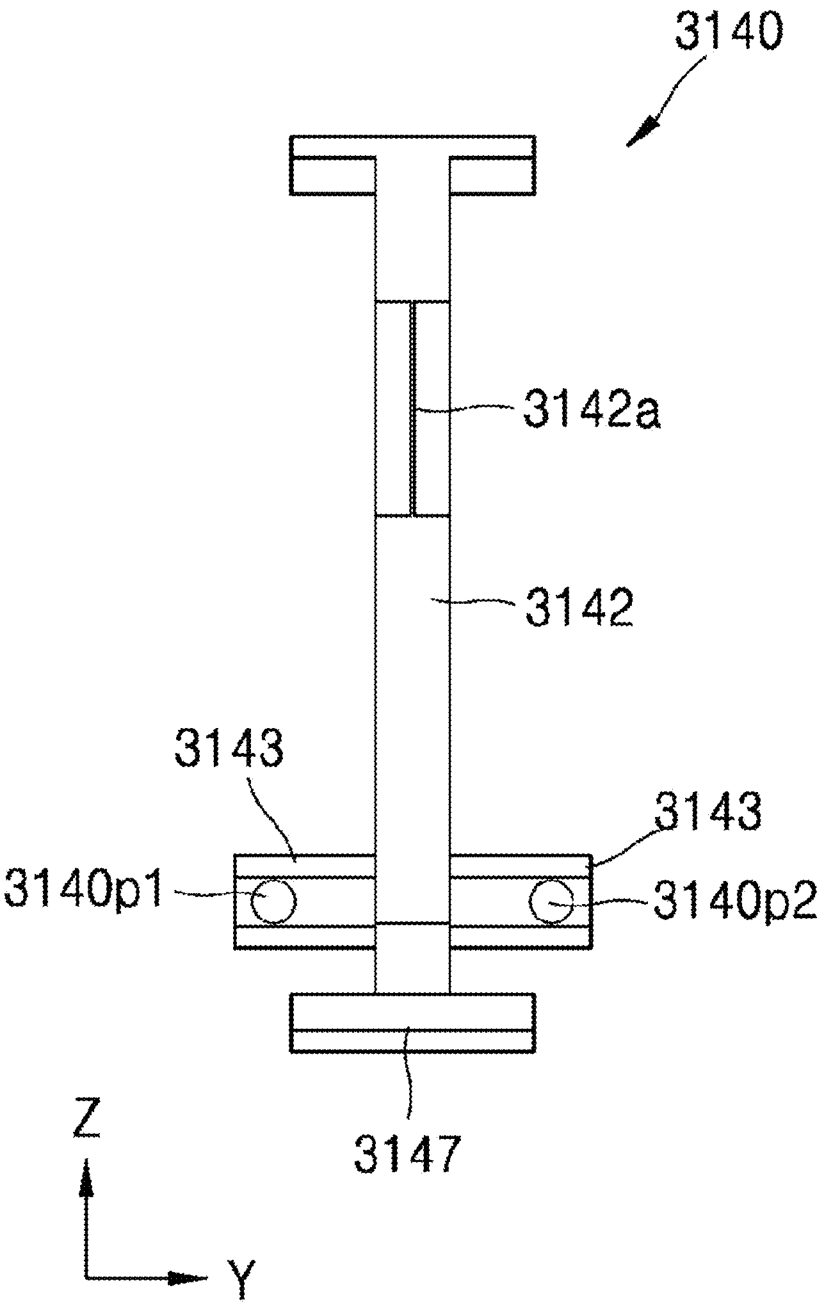
FIG. 12 is a front view of the working member of FIG. 10 as seen from one direction.
Figure 13:
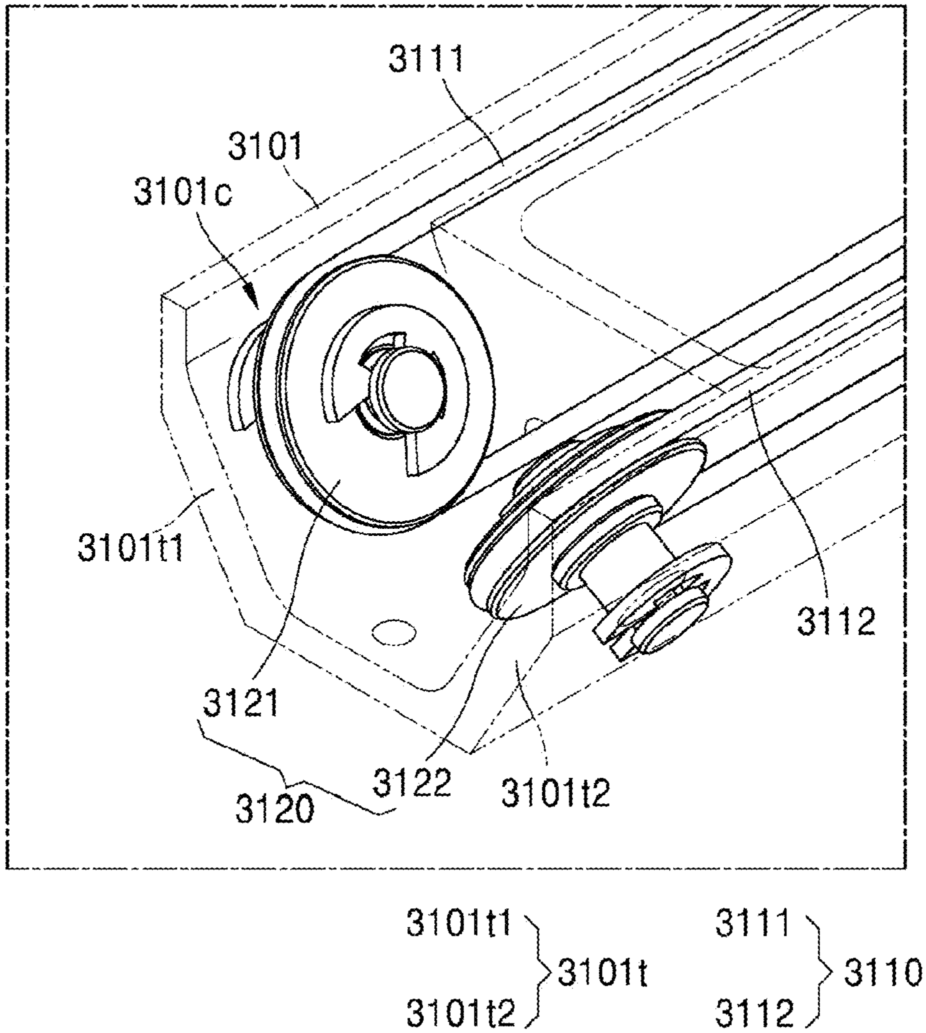
FIG. 13 is a schematic perspective view of a portion of the end tool of FIG. 1.
Figure 14:
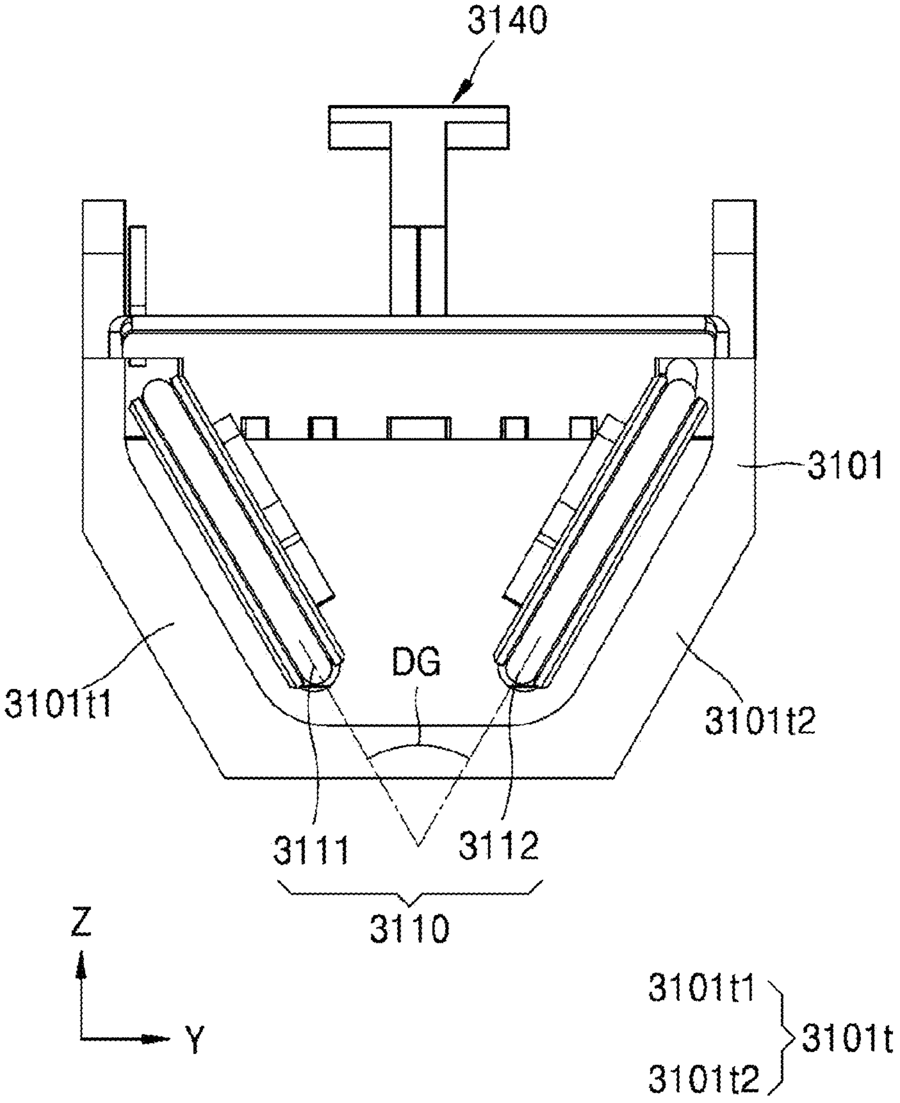
FIG. 14 is a front view of FIG. 13 as seen from one direction.
Figure 15:
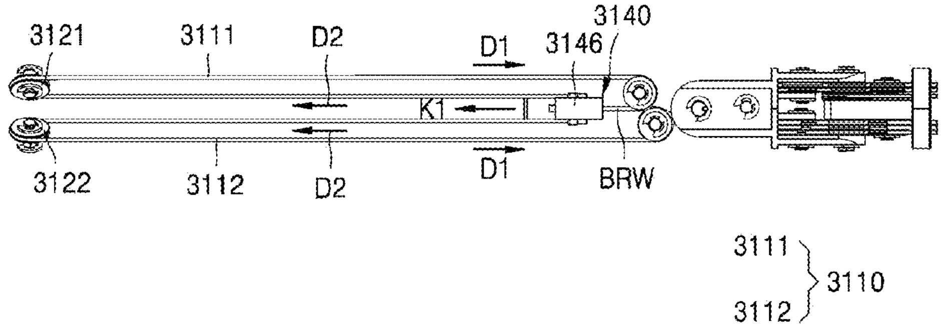
FIG. 15 is a schematic plan view of the working member, fixed pulley, and forward wire of the end tool of FIG. 1.
Figure 16:
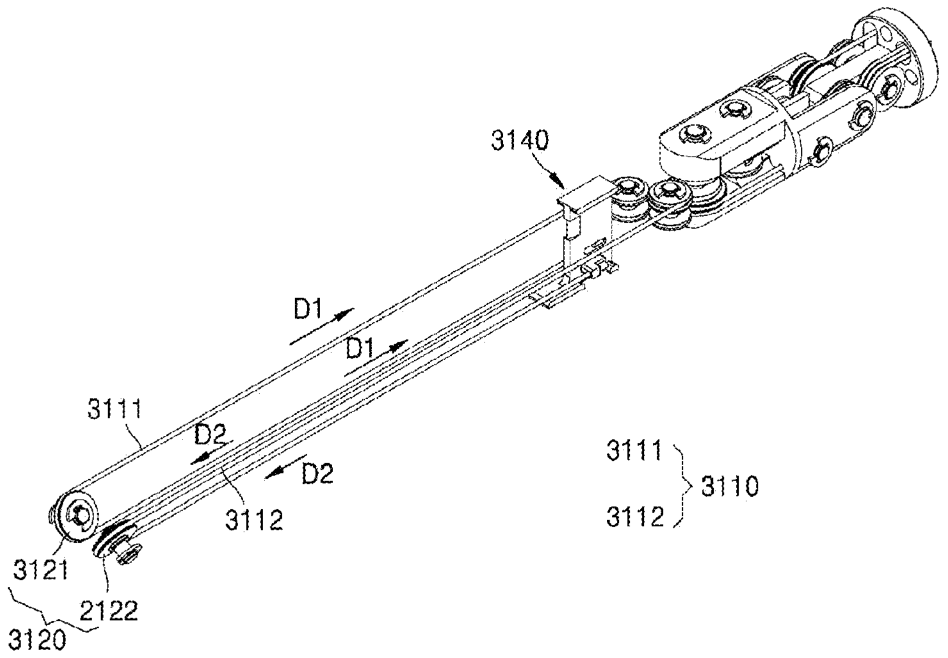
FIG. 16 is a schematic perspective view of the working member, fixed pulley, and forward wire of the end tool of FIG. 1.
Figure 17:
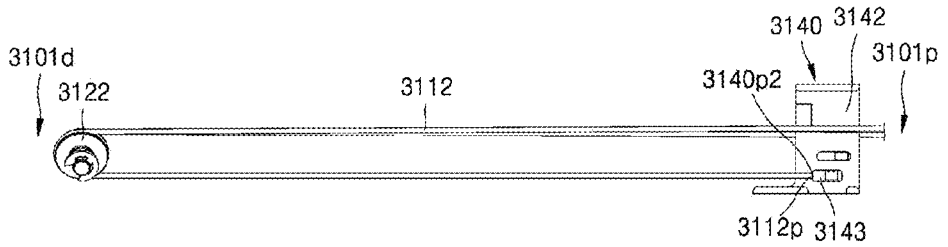
FIGS. 17 and 18A to 18C are schematic diagrams illustrating the operation of the working member of the end tool of FIG. 1.
Figure 21:
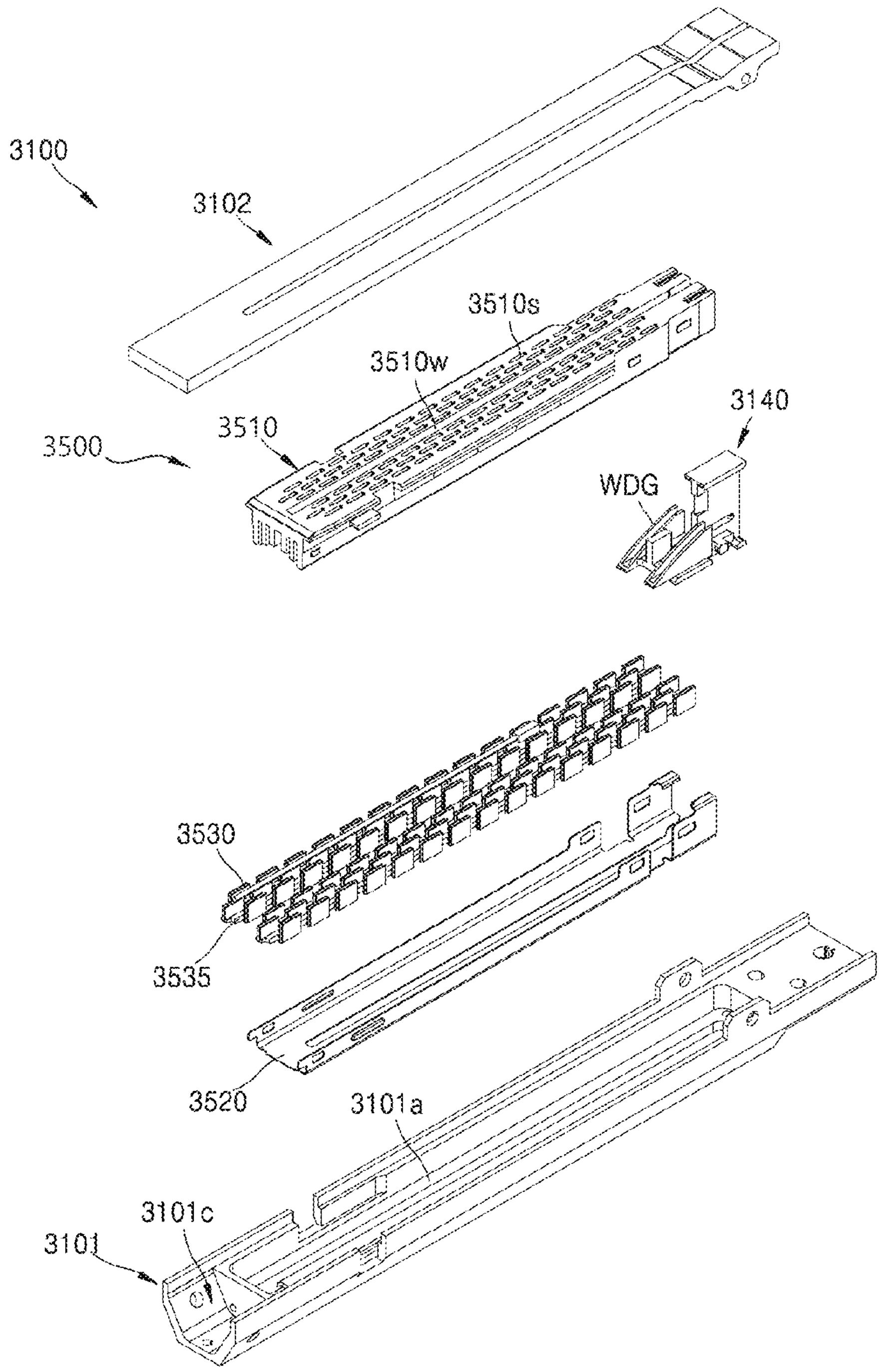
FIG. 21 is a perspective view of the first jaw and cartridge of the surgical instrument of FIG. 1.
Figure 22:
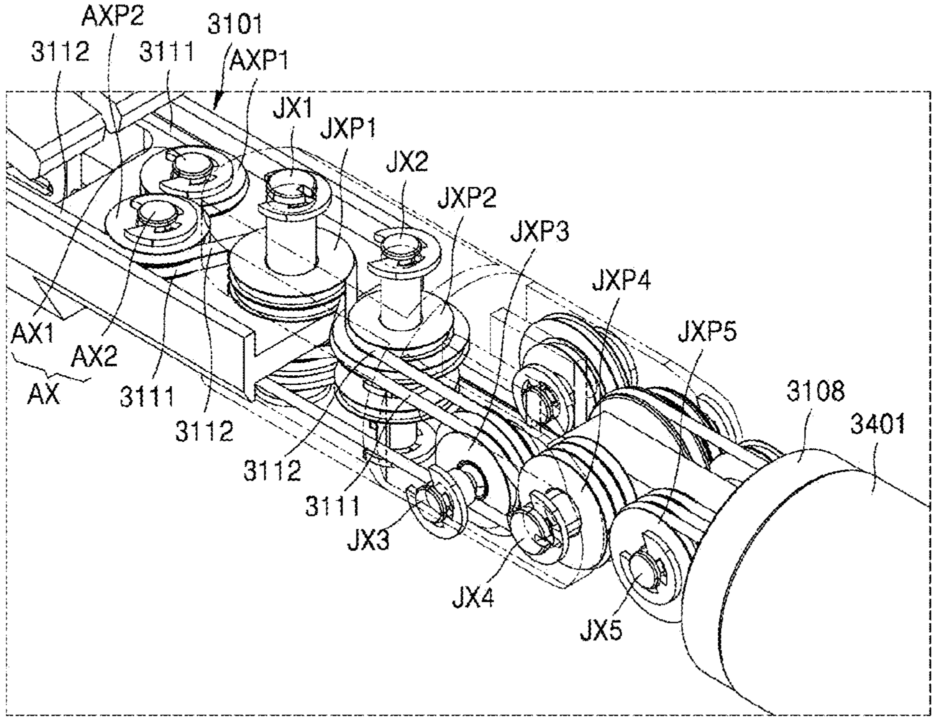
FIGS. 22 and 23 are views of a switching pulley, a yaw pulley, and a pitch pulley of the end tool of the surgical instrument of FIG. 1.
Figure 23:
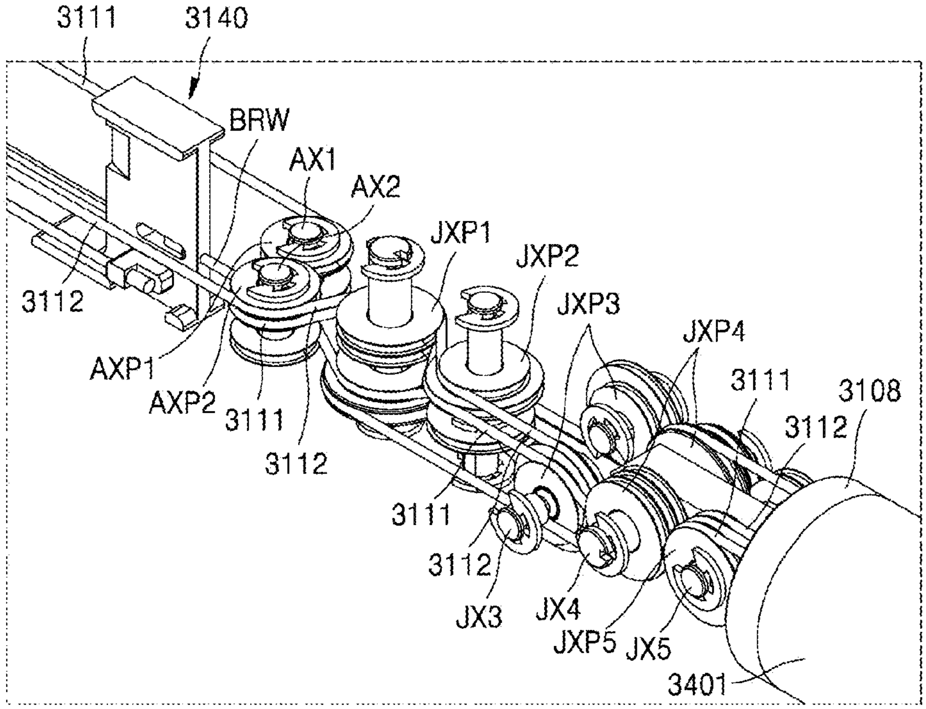

FIG. 1 is a schematic perspective view of a surgical instrument according to an embodiment of the present disclosure. FIG. 2 is a schematic perspective view of the end tool of FIG. 1. FIG. 3 is a perspective view of the end tool of FIG. 2 as seen from a different angle. FIG. 4 is a schematic perspective view of the end tool of FIG. 50 with a second jaw removed. FIG. 5 is a schematic perspective view of the end tool of FIG. 4 with a cartridge removed. FIG. 6 is a transparent perspective view of FIG. 5. FIG. 7 is a schematic perspective view of the second jaw of the end tool of FIG. 1. FIG. 8 is a schematic perspective view of a first jaw of the end tool of FIG. 1. FIG. 9 is a schematic plan view of the first jaw of the end tool of FIG. 1. FIG. 10 is a perspective view of the working member of the end tool of FIG. 1. FIG. 11 is a perspective view of the working member of FIG. 10 as seen from a different angle. FIG. 12 is a front view of the working member of FIG. 10 as seen from one direction. FIG. 13 is a schematic perspective view of a portion of the end tool of FIG. 1. FIG. 14 is a front view of FIG. 13 as seen from one direction. FIG. 15 is a schematic plan view of the working member, fixed pulley, and forward wire of the end tool of FIG. 1. FIG. 16 is a schematic perspective view of the working member, fixed pulley, and forward wire of the end tool of FIG. 1. FIGS. 17 and 18 are schematic diagrams illustrating the operation of the working member of the end tool of FIG. 1. FIGS. 19 and 20 are diagrams illustrating an optional embodiment in which a backward wire is added to the end tool of FIG. 1. FIG. 21 is a perspective view of the first jaw and cartridge of the surgical instrument of FIG. 1. FIGS. 22 and 23 are views of a switching pulley, a yaw pulley, and a pitch pulley of the end tool of the surgical instrument of FIG. 1.

A surgical instrument 3000 according to an embodiment of the present disclosure includes an end tool 3100, a manipulation unit 3200, and a connection unit 3400.

Herein, the connection unit 3400 is formed in the shape of a hollow shaft, and one or more wires and electric wires may be accommodated therein. The manipulation unit 3200 is coupled to one end portion of the connection unit 3400, the end tool 3100 is coupled to the other end portion thereof, so that the connection unit 3400 may serve to connect the manipulation unit 3200 and the end tool 3100. As an example, the connection unit 3400 may include a straight line unit 3401, and although not shown, may also include one or more curved units for ease of use and control of disposition of the configuration of manipulation.

The manipulation unit 3200 is formed at the one end portion of the connection unit 3400 and is provided with an interface that may be directly controlled by a medical doctor, for example, a tong shape, a stick shape, a lever shape, or the like. When the medical doctor controls the manipulation unit 3200, the end tool 3100 connected to the interface and inserted into the body of a surgical patient performs certain activation, thereby performing surgery. Herein, although the manipulation unit 3200 is illustrated in FIG. 1 as being formed in the shape of a handle that is in close contact with a finger and performs one or more operations, such as pulling or pushing, the idea of the present disclosure is not limited thereto, and various types of manipulation units that are connected to the end tool 3100 and manipulate the end tool 3100 may be possible.

The end tool 3100 is formed on the other end portion of the connection unit 3400, and performs necessary operations for surgery by being inserted into a surgical site. In an example of the end tool 3100 described above, a pair of jaws 3103 for performing a grip operation may be used. However, the idea of the present disclosure is not limited thereto, and various devices for performing surgery may be used as the end tool 3100. For example, a configuration of a cantilever cautery may also be used as the end tool. The end tool 3100 is connected by the manipulation unit 3200 and the power transmission unit (not shown, for example wire), and receives a driving force of the manipulation unit 3200 through the power transmission unit to perform an operation necessary for surgery, such as gripping, cutting, suturing, or the like.

Hereinafter, the end tool 3100 of the surgical instrument 3000 of FIG. 1 will be described in more detail.

FIG. 2 is a schematic perspective view of the end tool of FIG. 1. FIG. 3 is a perspective view of the end tool of FIG. 2 as seen from a different angle. FIG. 4 is a schematic perspective view of the end tool of FIG. 1 with a second jaw removed. FIG. 5 is a schematic perspective view of the end tool of FIG. 4 with a cartridge removed. FIG. 6 is a transparent perspective view of FIG. 5.

The end tool 3100 may include a jaw 3103, a plurality of fixed pulleys 3120, and a plurality of forward wires 3110. The plurality of fixed pulleys 3120 may include two or more pulleys, for example, a first fixed pulley 3121 and a second fixed pulley 3122. The plurality of forward wires 3110 may include two or more wires, for example, a first forward wire 3111 and a second forward wire 3112.

The jaw 3103 may perform various functions, for example, a gripping operation, and may include, as a specific example, a pair of jaws, namely, a first jaw 3101 and a second jaw 3102. Herein, each of the first jaw 3101 and the second jaw 3102, or a component encompassing the first jaw 3101 and the second jaw 3102 may be referred to as the jaw 3103.

The first jaw 3101 and the second jaw 3102 may be disposed opposite to each other, and may perform a motion to be close to each other and a motion to be away from each other, and may be formed to rotate about an axis (JX), for example.

A cartridge 3500 may be disposed to be accommodated in the first jaw 3101, and a plurality of staples are disposed inside the cartridge 3500. In a state where the first jaw 3101 and the second jaw 3102 are close to each other, for example, in a state where body tissue is interposed therebetween and the first jaw 3101 and the second jaw 3102 are closed, a working member 3140 receives a force from the plurality of forward wires 3110 and performs a motion in the direction of a distal unit 3101*d* of the first jaw 3101 to push up the staples, so that stapling may be performed. In this connection, one or more clamps 3146 and 3147 of the working member 3140 may be moved forward while applying pressure to an outer surface of the first jaw 3101 and the second jaw 3102 while protruding outside the first jaw 3101 and the second jaw 3102, so that the stapling process may proceed smoothly. As an optional embodiment, the cartridge 3500 may have a case 3520 corresponding to the bottom and may have a form in which the case 3520 is disposed on the first jaw 3101.

The working member 3140 may be used together with a wedge (WDG). For example, the wedge (WDG) may be prepared separately from the working member 3140 and then disposed adjacent to the working member 3140 on the first jaw 3101. In addition, as another example, the working member 3140 and the wedge (WDG) may be formed integrally. The wedge (WDG) may be disposed on at least one side of a main body 3142 and may be formed to have a predetermined inclined surface. In other words, the wedge (WDG) may be formed to have a predetermined inclination in an extension direction of the end tool 3100. In other words, the height of a proximal unit 3101*p* may be formed to be higher than that of the distal unit 3101*d* of the first jaw 3101.

The wedge (WDG) as such may be formed to be able to sequentially contact a withdrawal member 3535 (FIG. 21) or a plurality of staples 3530 (FIG. 21) disposed in the cartridge 3500, and may perform a role of sequentially pushing up the staples 3530.

The plurality of fixed pulleys 3120 may be disposed on the first jaw 3101 so as to be closer to the distal unit 3101*d* of the first jaw 3101 than the cartridge 3500, in other words, the plurality of fixed pulleys 3120 may be disposed on the front of the cartridge 3500. For example, the plurality of fixed pulleys 3120 may be disposed in a front space unit 3101*c* of the first jaw 3101, and the specific details will be described later.

In addition, the end tool 3100 of the surgical instrument of an embodiment of the present disclosure may include one or more members, such as an articulation member, connecting the jaw 3103 and the connection unit 3400. In addition, as an optional embodiment, the end tool 3100 may include an end tool hub 3108 and a pitch hub 3107.

The end tool hub 3108 may be disposed to connect the end tool 3100 and the straight line unit 3401 of the connection unit 3400.

For example, the end tool hub 3108 may correspond to a pulley axis (JX4), and this pulley axis (JX4) may be a pitch rotation axis. As a specific example, the end tool 3100 may rotate up and down in the drawing around the pulley axis (JX4). In addition, one or more pulleys may be disposed adjacent to this pulley axis (JX4).

The end tool hub 3108 may be in the form of a bar that protrudes long from the center of a surface corresponding to the straight line unit 3401 of the connection unit 3400, for example, a main area in the form of a disc, and the pulley axis (JX4) and another pulley axis (JX5) may additionally correspond to this bar area.

The pitch hub 3107 is connected to the end tool hub 3108 and the jaw 3103.

The pitch hub 3107 may be axially coupled with the end tool hub 3108 based on the one pulley axis (JX4). The pitch hub 3107 may rotate around the one pulley axis (JX4) while being connected to the end tool hub 3108. In other words, the end tool 3100 may perform a pitch motion by rotating the pitch hub 3107 around the one pulley axis (JX4) with respect to the end tool hub 3108.

In addition, the jaw 3103 of the end tool 3100 may be axially coupled with the pitch hub 3107 based on one pulley axis (JX1). The jaw 3103 may rotate around the one pulley axis (JX1) while being connected to the pitch hub 3107. In other words, the jaw 3103 of the end tool 3100 may perform a yaw motion by rotating around the one pulley axis (JX1) with respect to the pitch hub 3107.

As a result, when the yaw motion of the end tool 3100 is performed, the jaw 3103 rotates around the one pulley axis (JX1) with respect to the pitch hub 3107, and when the pitch motion of the end tool 3100 is performed, the pitch hub 3107 rotates around the one pulley axis (JX4) with respect to the end tool hub 3108. Accordingly, the jaw 3103 coupled with the pitch hub 3107 rotates around the pitch hub 3107.

The pitch hub 3107 may include a first hub 3107*a* and a second hub 3108.

The first hub 3107*a* of the peach hub 3107 may be connected to the jaw 3103, and may be formed long so as to be connected to one area of the first jaw 3101, and as a specific example, may include two bar shapes that are parallel and opposite to each other, and one area of the first jaw 3101 may be disposed and coupled therebetween.

A second hub 3107*b* of the pitch hub 3107 is connected to the end tool hub 3108, and may include, for example, two bar shapes that are parallel and opposite to each other, and one area of the end tool hub 3108 may be disposed and coupled therebetween.

As described above, another pulley axis (JX5) may be disposed on the end tool hub 3108, wherein another pulley axis (JX5) is spaced apart from the pulley axis (JX4) and closer to the connection unit 3400 (FIG. 1) than the one pulley axis (JX4) is. The pulley axis (JX4) and the pulley axis (JX5) may include shafts in a direction parallel to each other.

The pitch hub 3107 may be provided with another pulley axis (JX2) disposed adjacent to and parallel to the pulley axis (JX1), and the pulley axis (JX1) and the pulley axis (JX2) may be sequentially disposed in different directions, for example, in an intersecting or orthogonal direction, with the pulley axis (JX3) and the pulley axis (JX4) facing the connection unit (or away from the working member).

The pulley axis (JX4) may be a pitch motion axis of the end tool 3100, and the pulley axis (JX1) may be a yaw motion axis.

The pulley axis (JX3) and the pulley axis (JX5) may be pitch auxiliary pulley axes, and the pulley axis (JX2) may be a yaw auxiliary pulley axis. These pulley axes (JX1, JX2, JX3, JX4, JX5) may have at least one area of a drive wire, for example, a wire transmitting a driving force for a pitch motion or a wire transmitting a driving force for a yaw motion, contacted or wound.

The pulley axes (JX2, JX3, JX5) adjacent to the pulley axis (JX4) as a pitch motion axis and the pulley axis (JX1) as a yaw motion axis may control the path along which the drive wires are wound around the pulley axle (JX4) and the pulley axle (JX1), thereby ensuring the efficiency of the disposition of the drive wires and the stability of the path and transmission of force through the drive wires.

In addition, these pulley axes (JX1, JX2, JX3, JX4, JX5) may have at least one area of a forward wire 3110 contacted or wound.

A more specific description of the disposition of these pulley axes (JX1, JX2, JX3, JX4, and JX5) will be described later.

One or more switching pulley axes (AX1, AX2) may be disposed on the end tool 3100, and one or more pulleys corresponding to the switching pulley axes (AX1, AX2) may be disposed.

For example, the switching pulley axes (AX1, AX2) may be disposed in a direction close to the proximal unit 3101*p* of the first jaw 3101, as a specific example, and may be disposed closer to the distal unit 3101*d* of the first jaw 3101 than at least the pulley axes (JX1, JX2, JX3, JX4, JX5) described above are.

The pulley axes (AX1, AX2) may be formed parallel to each other, and may be disposed so that their forward and backward locations are different from each other, so that the switching pulley axis (AX1) and the switching pulley axis (AX2) are disposed sequentially based on the distal unit 3101*d* of the first jaw 3101, and may be disposed so that some areas overlap.

The switching pulley axes (AX1, AX2) are provided with an area in which at least one area of the forward wire 3110 is wound or contacted, so that the forward wire 3110 may arrange and guide a path before entering the pulley axes (JX1, JX2, JX3, JX4, JX5). A more specific description of the disposition of the switching pulley axles (AX1, AX2) will be provided later.

As illustrated in FIG. 6, the first forward wire 3111 and the second forward wire 3112 are wound around the first fixed pulley 3121 and the second fixed pulley 3122 in the first jaw 3101 to change direction, and are connected to the rear of the end tool 3100 through at least one area of the switching pulley axes (AX1, AX2) and the pulley axes (JX1, JX2, JX3, JX4, JX5), and further extended to the manipulation unit 3200 (FIG. 1) through the connection unit 3400 so as to be precisely controlled. Thus, precise motion control of the working member 3140 may be easily implemented, and the specific details thereof will be described later.

The jaw 3103 of the end tool 3100 will be described in more detail.

FIG. 7 is a schematic perspective view of the second jaw of the end tool of FIG. 1.

The second jaw 3102 is formed entirely in an elongated rod shape, and for example, the second jaw 3102 may be formed to correspond to at least one area of the first jaw 3101 in the rod shape.

The proximal unit 3101*p* of the second jaw 3102 may include an area that is coupled to the first jaw 3101. For example, the proximal unit 3101*p* may be formed to be rotatable relative to the first jaw 3101 around an axis (JX).

The second jaw 3102 may have various shapes, and as a specific example, a plurality of anvil grooves may be formed in at least one area of a surface of the second jaw 3102 facing the first jaw 3101, and these anvil grooves may include a shape corresponding to the shape of the staple 3530.

The anvil groove of the second jaw 3102 may serve as a support to allow the staple 3530 to be bent when the working member 3140 pushes up the staple 3530 in a staple operation.

The second jaw 3102 includes a guide groove 3102*a*. The guide groove 3102*a* may have a shape that is elongated along the length direction of the second jaw 3102.

The guide groove 3102*a* may be formed to guide the working member 3140 and may be a groove that penetrates an area facing the working member 3140. Thus, one area of the working member 3140, for example, at least one area of the main body 3142 of the working member 3140 or a first clamp 3146 connected thereto may pass through the guide groove 3102*a* and be discharged to the outside of the second jaw 3102. When the working member 3140 moves forward, the first clamp 3146 passes through the guide groove 3102*a* of the second member 3102 and is exposed to the outside of the second jaw 3102, and may contact or apply pressure to an upper surface of the second jaw 3102. Through the movement of the working member 3140, the first clamp 3146 applies pressure to the upper surface of the second jaw 3102, and a second clamp 3147 to be described later applies pressure to a lower surface of the first jaw 3101, so that the gap between the second jaw 3102 and the first jaw 3101 narrows, and the second jaw 3102 may naturally maintain a closed state with respect to the first jaw 3101.

FIG. 8 is a schematic perspective view of a first jaw of the end tool of FIG. 1. FIG. 9 is a schematic plan view of the first jaw of the end tool of FIG. 1.

Referring to FIGS. 8 and 9, the first jaw 3101 is formed entirely in an elongated rod shape, a rotation axis may be disposed in the proximal unit to enable rotational motion, and this rotation axis may correspond to the rotation axis (JX) formed in the second jaw 3102 described above. In addition, the cartridge 3500 (FIG. 1) may be accommodated on the side closer to the distal unit 3101*d* than the rotation axis.

For example, the first jaw 3101 may be formed entirely as a hollow box with one side (upper surface) removed, and a cartridge accommodation unit 3101*a* capable of accommodating the cartridge 3500 may be formed inside the first jaw 3101. In other words, the first jaw 3101 may be formed with a cross section that is approximately in a 'U' shape.

A guide groove 3101*h* may be formed on a bottom surface of the first jaw 3101, in other words, the bottom surface opposite to the upper open area removed on one side. Specifically, the guide groove 3101*h* may be formed to guide the linear motion of the working member 3140.

The guide groove 3101*h* may be formed to guide the working member 3140, and may be a groove that penetrates the area facing the working member 3140. Thus, one area of the working member 3140, for example, at least one area of the main body 3142 of the working member 3140 or the second clamp 3147 connected thereto, may pass through the guide groove 3101*h* and be discharged to the outside of the first jaw 3101. When the working member 3140 moves forward, the second clamp 3147 passes through the guide groove 3101*h* of the first jaw 3101 and is exposed to the outside of the first jaw 3101, and may contact or apply pressure to the lower surface of the first jaw 3101. Through the movement of the working member 3140, the second clamp 3147 applies pressure to the lower surface of the first jaw 3101, and the first clamp 3146 applies pressure to the upper surface of the second member 3102, so that the gap between the second jaw 3102 and the first jaw 3101 narrows, and the second jaw 3102 may naturally maintain a closed state with respect to the first jaw 3101.

As an optional embodiment, the first jaw 3101 may include a window 3101*b*. After the work of the working member 3140 or after the use of the end tool 3100, the second clamp 3147 of the working member 3140 may correspond to the window 3101*b* and release the coupling state of the first jaw 3101 and the working member 3140.

The first jaw 3101 may include a forward space unit 3101*c* in front of a cartridge accommodation unit 3101*a*.

For example, the forward space unit 3101*c* may be disposed closer to the distal unit 3101*d* of the first jaw 3101 than the cartridge accommodation unit 3101*a* is. The plurality of fixed pulleys 3120 may be disposed in the forward space unit 3101*c*, for example, the first fixed pulley 3121 and the second fixed pulley 3122 may be disposed (see, for example, FIGS. 2 to 6).

Each of two outer side surfaces corresponding to the front space unit 3101*c* includes a first side surface 3101*t*1 and a second side surface 3101*t*2, and the first fixed pulley 3121 and the second fixed pulley 3122 may be disposed to correspond to the first side surface 3101*t*1 and the second side surface 3101*t*2.

The first side surface 3101*t*1 and the second side surface 3101*t*2 may each be formed in an inclined shape. For example, the first side surface 3101*t*1 and the second side surface 3101*t*2 may not be parallel to each other with the same gap, but may have a shape in which the gap decreases along a downward direction.

As a specific example, the gap between the first side surface 3101*t*1 and the second side surface 3101*t*2 may be formed to become narrower along a direction away from the second jaw 3102.

Since the first fixed pulley 3121 and the second fixed pulley 3122 are disposed corresponding to the first side surface 3101*t*1 and the second side surface 3101*t*2, respectively, the spacing between the first fixed pulley 3121 and the second fixed pulley 3122 may be disposed in an inclined shape so that the spacing therebetween becomes narrower with respect to the direction away from the second jaw 3102 (FIG. 2). The first fixed pulley 3121 and the second fixed pulley 3122 may be symmetrical and may have the same size.

In addition, a first passage 3101*w*1 and a second passage 3101*w*2 are formed adjacent to the front space unit 3101*c*, and these passages may be, for example, in the form of through holes formed in a barrier wall, and may be areas through which the first forward wire 3111 and the second forward wire 3112 pass, respectively.

As an optional embodiment, when a rearward wire (for example, see FIG. 19) is disposed, the first jaw 3101 may include a rear passage 3101R corresponding to the rearward wire.

In addition, the first jaw 3101 may include a coupling area 3101*z* adjacent to the proximal unit 3101*p*. The coupling area 3101*z* is an area that is coupled to the pitch hub 3107, and may be, for example, in the form of a plate that is formed long to correspond to the first hub 3107*a* of the pitch hub 3107. The coupling area 3101*z* may be disposed and coupled between two bar-shaped first hubs 3107*a* of the pitch hub 3107.

The working member 3140 will be described in detail.

FIG. 10 is a perspective view of the working member of the end tool of FIG. 1. FIG. 11 is a perspective view of the working member of FIG. 10 as seen from a different angle. FIG. 12 is a front view of the working member of FIG. 10 as seen from one direction.

The working member 3140 may include the main body 3142, the first clamp 3146, and the second clamp 3147. The working member 3140 may be used together with the wedge (see WDG of FIGS. 4 and 5). For example, the wedge (WDG) may be prepared separately from the working member 3140 and then disposed adjacent to the working member 3140 in the first jaw 3101. In addition, as another example, the working member 3140 and the wedge (WDG) may be formed integrally. In this specification, for the convenience of explanation, descriptions and illustrations are made on the premise that the working member 3140 and the wedge (WDG) are prepared separately.

The wedge (WDG) may be disposed on at least one side of the main body 3142 and may be formed to have a predetermined inclined surface. In other words, the wedge (WDG) may be formed to have a predetermined inclination in the extension direction of the end tool 3100. In other words, the height of the proximal unit 3101*p* may be formed to be higher than that of the distal unit 3101*d* of the first jaw 3101.

The wedge (WDG) as such may be formed to be able to sequentially contact the withdrawal member 3535 (FIG. 21) or the plurality of staples 3530 (FIG. 21), and may perform a role of sequentially pushing up the staples 3530.

The main body 3142 may be in the form of a long column, for example, in the form of a plate-shaped column. In addition, a blade area 3142*a* may be formed in one area of the main body 3142, and an edge unit that is formed sharply and cuts tissue may be formed in the blade area 3142*a*. When at least a portion of the edge unit formed in the blade area 3142*a* of the main body 3142 is withdrawn to the outside of the first jaw 3101 and the cartridge 3500, the tissue disposed between the first jaw 3101 and the second jaw 3102 may be cut.

The first clamp 3146 may be formed in one area of the main body 3142, and the second clamp 3147 may be formed in another area. For example, the main body 3142 may be disposed between the first clamp 3146 and the second clamp 3147.

The first clamp 3146 and the second clamp 3147 may be formed to have an area at least wider than the main body 3142. Thus, the first clamp 3146 is fitted into the guide groove 3102*a* formed along the length direction of the second jaw 3102, penetrates the guide groove 3102*a*, and is disposed on or in contact with the upper surface of the second jaw 3102, and at the same time, the second clamp 3147 is fitted into the guide groove 3101*h* formed along the length direction of the first jaw 3101, penetrates the guide groove 3101*h*, and is disposed on or in contact with the lower surface of the first jaw 3101, so that the first clamp 3146 and the second clamp 3147 may move. Thus, when the working member 3140 moves, the first clamp 3146 and the second clamp 3147 may apply a force in the direction in which the second jaw 3102 and the first jaw 3101 come closer to each other.

As a result, when the working member 3140 moves from the proximal unit 3101*p* of the first jaw 3101 to the distal unit 3101*d*, the operation of the second jaw 3102 approaching the first jaw 3101, i.e., the closing operation of the jaw 3103, may be naturally implemented through the first clamp 3146 and the second clamp 3147.

The first clamp 3146 and the second clamp 3147 may be at different locations in the forward direction with respect to the main body 3142. For example, the second clamp 3147 may be located further forward than the first clamp 3146, and for example, when the working member 3140 is disposed on the first jaw 3101, the second clamp 3147 may be located closer to the distal unit 3101*d* of the first jaw 3101 than the first clamp 3146 is. Thus, when the working member 3140 moves forward in the closed state of the first jaw 3101 and the second jaw 3102, the first jaw 3101 and the second jaw 3102 may be maintained more efficiently and stably during stapling.

A first connection area 3140*p*1 and a second connection area 3140*p*2 may be formed in one area of the main body 3142, for example, in one area of the front, specifically, in one area facing the distal unit 3101*d* of the first jaw 3101.

The first connection area 3140*p*1 and the second connection area 3140*p*2 may be areas where the first forward wire 3111 and the second forward wire 3112 are connected, respectively, and may have a fixing groove shape, for example, so that one area of each end of the first forward wire 3111 and the second forward wire 3112 is accommodated or fixed. When the first forward wire 3111 and the second forward wire 3112 are connected to the first connection area 3140*p*1 and the second connection area 3140*p*2 and the first forward wire 3111 and the second forward wire 3112 are pulled, the force that pulls the first forward wire 3111 and the second forward wire 3112 is transmitted to the working member 3140 through the first connection area 3140*p*1 and the second connection area 3140*p*2, so that the working member 3140 may move, in other words, move forward.

As an optional embodiment, the first connection area 3140*p*1 and the second connection area 3140*p*2 may be formed on a side unit 3143 of the working member 3140.

The side unit 3143 may have a shape that protrudes outward from each of the two side surfaces of the main body 3142. By forming the first connection area 3140*p*1 and the second connection area 3140*p*2 on the side unit 3143 protruding on both sides of the main body 3142, a space for connecting the first forward wire 3111 and the second forward wire 3112 to the first connection area 3140*p*1 and the second connection area 3140*p*2 may be easily secured.

In addition, the first connection area 3140*p*1 and the second connection area 3140*p*2 are formed on the side unit 3143 on both sides with the main body 3142 as the center, and the first forward wire 3111 and the second forward wire 3112 are connected to the first connection area 3140*p*1 and the second connection area 3140*p*2, so that the first forward wire 3111 and the second forward wire 3112 may be pulled to both sides with the main body 3142 as the center, and may also be pulled at symmetrical locations, so that a precise forward motion of the working member 3140 may be controlled.

As an optional embodiment, a connection area for a backward wire may be formed in the rear area of the main body 3142.

FIG. 13 is a schematic perspective view of a portion of the end tool of FIG. 1. FIG. 14 is a front view of FIG. 13 as seen from one direction.

Referring to FIGS. 13 and 14, the first fixed pulley 3121 and the second fixed pulley 3122 may be disposed not parallel with each other but rather in an inclined shape. For example, based on the drawing, as a specific example, the first fixed pulley 3121 and the second fixed pulley 3122 may be disposed so that the gap between the first fixed pulley 3121 and the second fixed pulley 3122 becomes narrower along a direction away from the second jaw 3102 (FIG. 2).

Specifically, the first fixed pulley 3121 and the second fixed pulley 3122 may be disposed opposite to each other in the front space unit 3101*c* located in front of the cartridge accommodation unit 3101*a* of the first jaw 3101, and as a specific example, the first fixed pulley 3121 and the second fixed pulley 3122 may be disposed in a symmetrical shape. In addition, the first fixed pulley 3121 and the second fixed pulley 3122 may be formed to have the same size.

Each of the two outer side surfaces corresponding to the front space unit 3101*c* includes the first side surface 3101*t*1 and the second side surface 3101*t*2, and the first fixed pulley 3121 and the second fixed pulley 3122 may be disposed to correspond to the first side surface 3101*t*1 and the second side surface 3101*t*2.

The first side surface 3101*t*1 and the second side surface 3101*t*2 may each be formed in an inclined shape. For example, the first side surface 3101*t*1 and the second side surface 3101*t*2 may not be parallel to each other with the same gap, but may have a shape in which the gap decreases along a downward direction. As a specific example, the gap between the first side surface 3101*t*1 and the second side surface 3101*t*2 may be formed to become narrower along a direction away from the second jaw 3102 (FIG. 2). In addition, the first side 3101*t*1 and the second side 3101*t*2 may have a symmetrical shape.

The first fixed pulley 3121 and the second fixed pulley 3122 may be wound with the first forward wire 3111 and the second forward wire 3112, respectively, and the areas wound downward may face the first connection area 3140*p*1 and the second connection area 3140*p*2 of the aforementioned working member 3140.

Through this shape, the balance characteristics of the disposition of the first fixed pulley 3121 and the second fixed pulley 3122 and the first forward wire 3111 and the second forward wire 3112 based on the direction of motion of the working member 3140 may be improved, and for example, a symmetrical shape may be easily implemented. In addition, the shaking or rotational moment that occurs when the first forward wire 3111 and the second forward wire 3112 are pulled may be reduced, thereby reducing or preventing the vibration of the end tool 3100.

In addition, the shape of the end tool 3100, for example, one side of the first jaw 3101, which is one side of the jaw 3103, and as a specific example, the width of the main area of the lower side may be formed to be reduced, so that the overall compact structure of the end tool 3100 may be implemented.

In addition, the first fixed pulley 3121 and the second fixed pulley 3122 may be disposed not parallel with each other but rather in an inclined shape, through which the two forward wires 3111 and 3112 are wound around the lower side of the first fixed pulley 3121 and the second fixed pulley 3122 and connected to the working member 3140, and, for example, are disposed in the lower area of the cartridge 3500 by passing through the first passage 3101*w*1 and the second passage 3101*w*2, and the other area of the two forward wires 3111 and 3112 is wound around the upper side of the first fixed pulley 3121 and the second fixed pulley 3122 and disposed on both sides of the cartridge 3500. In other words, the first fixed pulley 3121 and the second fixed pulley 3122 may be disposed between both side surfaces of the cartridge 3500 and the first jaw 3101, respectively.

By disposing these two forward wires 3111 and 3112, it is possible to avoid fixing the working member 3140 to the center line of the forward wires 3111 and 3112, thereby maintaining the durability of the working member 3140, and to implement a compact shape of the working member 3140.

In addition, since the two forward wires 3111 and 3112 are disposed in a shape that is inclined on both sides, for example, the first fixed pulley 3121 and the second fixed pulley 3122 in a symmetrical shape, the maximum tension applied to the two forward wires 3111 and 3112 is made to be the same or almost similar, so that the fatigue life of each may be improved.

In addition, it is possible to control one area of the two forward wires 3111 and 3112 to pass symmetrically toward the lower side of the cartridge 3500 and the other area to pass symmetrically toward both sides of the cartridge 3500, thereby reducing or preventing unintended movement or vibration of the end tool 3100 or the instrument 3000 including the same caused by undesired moment or rotational force generated when pulling the two forward wires 3111 and 3112.

Referring to FIG. 14, the first fixed pulley 3121 and the second fixed pulley 3122 may be disposed not parallel but rather in a slanted shape, in other words, an inclined shape.

For example, the first fixed pulley 3121 and the second fixed pulley 3122 may be disposed to be slanted at 35 degrees (Deg) to 51 degrees (Deg) based on the vertical line (parallel to a Z-axis) as shown in FIG. 14, respectively.

In addition, as another expression, the central axis of the first fixed pulley 3121 and the central axis of the second fixed pulley 3122 may not be parallel to each other but may have an angle and be inclined. For example, the central axis of the first fixed pulley 3121 and the central axis of the second fixed pulley 3122 may be disposed to be slanted at 78 degrees (Deg) to 110 degrees (Deg).

In addition, as another expression, as illustrated in FIG. 14, the first fixed pulley 3121 and the second fixed pulley 3122 may have an adjacent angle (DG) and be inclined.

The adjacent angle (DG) may be 70 degrees (deg) to 102 degrees (deg).

When the adjacent angle (DG) is smaller than 70 degrees or exceeds 102 degrees, the diameters of the first fixed pulley 3121 and the second fixed pulley 3122 accommodated within the defined space of the first jaw 3101 become smaller. As a result, the stress applied to the wound forward wire 3111 and 3112 may increase, and the maximum allowable tension and durability of the forward wire 3111 and 3112 may decrease. Accordingly, the adjacent angle (DG) may be 70 degrees (deg) to 102 degrees (deg), and for a specific example, the adjacent angle (DG) may be 86 degrees. This adjacent angle (DG) may also be applied to the embodiments described below.

The disposition relationship of the working member 3140 and the plurality of forward wires 3110 and the plurality of fixed pulleys 3120 will be further described.

FIG. 15 is a schematic plan view of the working member, fixed pulley, and forward wire of the end tool of FIG. 1. FIG. 16 is a schematic perspective view of the working member, fixed pulley, and forward wire of the end tool of FIG. 1.

As described above, the first fixed pulley 3121 and the second fixed pulley 3122 may be disposed in the front space unit 3101*c* of the first jaw 3101, and each of the first fixed pulley 3121 and the second fixed pulley 3122 may be fixed to the first jaw 3101 so as not to move, or may be fixed so as to be rotatable around one axis.

The first forward wire 3111 and the second forward wire 3112 may be wound around an outer peripheral surface of the first fixed pulley 3121 and the second fixed pulley 3122. To this end, the groove may be formed on the outer peripheral surface of the first fixed pulley 3121 and the second fixed pulley 3122.

The first fixed pulley 3121 and the second fixed pulley 3122 may be disposed at least at the distal unit 3101*d* of the first jaw 3101 relative to the working member 3140.

The first forward wire 3111 may be extended to have a length along the length direction of the first jaw 3101, and an area of one end thereof may be extended to the proximal unit 3101*p* of the first jaw 3101 and connected to the inside of a driving unit, for example, the manipulation unit 3200 (FIG. 2), via the switching pulley axis (AX1, AX2) or the switching pulleys coupled thereto and the pulley axis (JX1, JX2, JX3, JX4, JX5) or pulleys coupled thereto, so that the driving unit may be pulled by manipulating the manipulation unit 3200.

Another end of the first forward wire 3111 extends in a direction toward the distal unit 3101*d* of the first jaw 3101 along the length direction of the first jaw 3101, contacts an area of the first fixed pulley 3121, is wound from the upper side, comes out downward, and extends in a direction toward the proximal unit 3101*p* of the first jaw 3101, so as to be connected and fixed to the first connection area 3140*p*1 of the working member 3140.

As an optional embodiment, an area of the first forward wire 3111 that extends to the distal unit 3101*d* of the first jaw 3101 and faces the upper side of the first fixed pulley 3121 may be parallel to an area that extends from the lower side of the first fixed pulley 3121 and toward the proximal unit 3101*p* of the first jaw 3101 and faces the first connection area 3140*p*1 of the working member 3140.

Thus, when the first forward wire 3111 is pulled toward the proximal unit 3101*p*, the pulling force may be effectively transmitted to the working member 3140. In addition, as an example, when the first forward wire 3111 is pulled toward the proximal unit 3101*p*, the ratio of the forward distance of the working member 3140 corresponding to the pulling force may be precisely controlled at a set ratio. As a specific example, when the first forward wire 3111 is pulled toward the proximal unit 3101*p*, the ratio of the pulling force and the forward distance of the working member 3140 may be easily controlled to a value that is equal to or substantially equal to 1 to 1 or similar.

The second forward wire 3112 may be extended to have a length along the length direction of the first jaw 3101, and an area of one end thereof may be extended to the proximal unit 3101*p* of the first jaw 3101 and connected to the inside of the driving unit, for example, the manipulation unit 3200 (FIG. 2), via the switching pulley axis (AX1, AX2) or the switching pulleys coupled thereto and the pulley axis (JX1, JX2, JX3, JX4, JX5) or pulleys coupled thereto, so that the driving unit may be pulled by manipulating the manipulation unit 3200.

Another end of the second forward wire 3112 extends in a direction toward the distal unit 3101*d* of the first jaw along the length direction of the first jaw 3101, contacts an area of the second fixed pulley 3122, is wound from the upper side, comes out downward, and extends in a direction toward the proximal unit 3101*p* of the first jaw 3101, so as to be connected and fixed to the second connection area 3140*p*2 of the working member 3140.

As an optional embodiment, an area of the second forward wire 3112 that extends to the distal unit 3101*d* of the first jaw 3101 and faces the upper side of the second fixed pulley 3122 may be parallel to an area that extends from the lower side of the second fixed pulley 3122 and toward the proximal unit 3101*p* of the first jaw 3101 and faces the second connection area 3140*p*2 of the working member 3140.

Thus, when the second forward wire 3112 is pulled toward the proximal unit 3101*p*, the pulling force may be effectively transmitted to the working member 3140.

As illustrated in FIG. 15 and FIG. 16, when the first forward wire 3111 and the second forward wire 3112 are pulled in a first direction (D1), an area of the first forward wire 3111 and the second forward wire 3112 moves in the first direction (D1). Accordingly, an area of the forward wire 3110 that is wound in an upper side of the first fixed pulley 3121 and the second fixed pulley 3122 and comes out downward moves in a second direction (D2) opposite to the first direction (D1). Accordingly, the force of the first forward wire 3111 and the second forward wire 3112 is transmitted to the first connection area 3140*p*1 and the second connection area 3140*p*2 connected to the first forward wire 3111 and the second forward wire 3112. By the force, the working member 3140 also performs motion in the same direction (K1) as the second direction (D2), that is, forward motion.

FIGS. 17 and 18A to 18C are schematic diagrams illustrating the operation of the working member of the end tool of FIG. 1.

Referring to FIGS. 17 and 18, for convenience of explanation, the first jaw 3101 is excluded, and the first forward wire 3111, the second forward wire 3112, the first fixed pulley 3121, the second fixed pulley 3122, and the working member 3140 are illustrated.

Figure 18A:
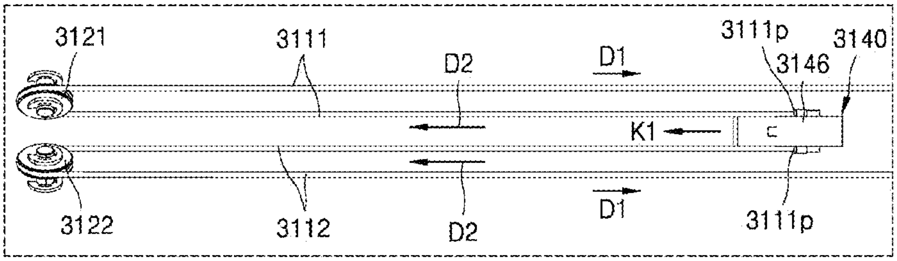
Figure 18B:
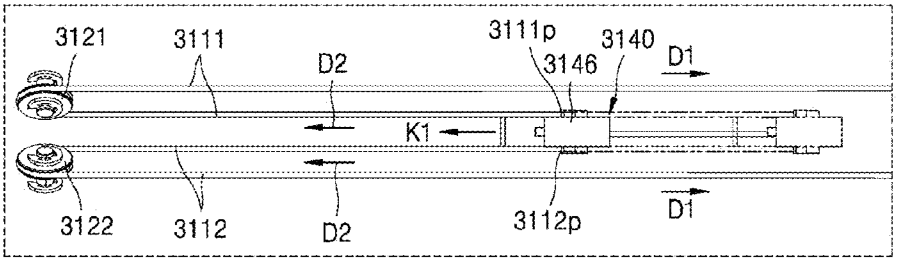
Figure 18C:
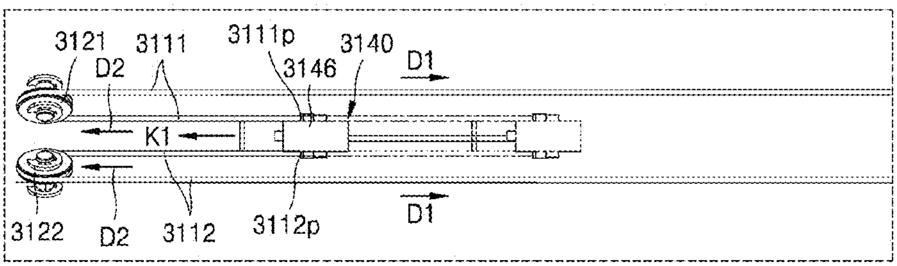
Figure 19:
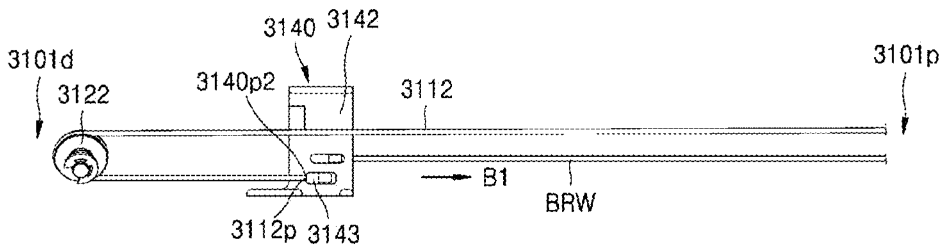
FIGS. 19 and 20A to 20C are diagrams illustrating an optional embodiment in which a backward wire is added to the end tool of FIG. 1.

Referring to FIG. 17, the working member 3140 may move in a left direction, in other words, move forward in the direction of the distal unit 3101*d*, and this forward motion is sequentially illustrated in FIGS. 18A, 18B, and 18C.

As illustrated in FIG. 18A, when the first forward wire 3111 and the second forward wire 3112 are pulled in the first direction (D1), each area of the first forward wire 3111 and the second forward wire 3112 is pulled in the first direction (D1). Accordingly, the areas of the first forward wire 3111 and the second forward wire 3112 that are wound upward and come out downward from the first fixed pulley 3121 and the second fixed pulley 3122 move in the second direction (D2) opposite to the first direction (D1). Accordingly, the force of the first forward wire 3111 and the second forward wire 3112 is transmitted respectively to the first connection area 3140*p*1 and the second connection area 3140*p*2 connected to the first forward wire 3111 and the second forward wire 3112. By the force, the working member 3140 also performs motion in the same direction (K1) as the second direction (D2), that is, forward motion, so that the working member 3140 is in the forward location of FIG. 18B.

Then, as illustrated in FIG. 18B, when the first forward wire 3111 and the second forward wire 3112 are further pulled in the first direction (D1), an area of the first forward wire 3111 and the second forward wire 3112 is further pulled in the first direction (D1). Accordingly, the area of the first forward wire 3111 and the second forward wire 3112 that is wound upward and comes out downward of the first fixed pulley 3121 and the second fixed pulley 3122 moves further in the second direction (D2) opposite to the first direction (D1). Accordingly, the force of the first forward wire 3111 and the second forward wire 3112 is transmitted respectively to the first connection area 3140*p*1 and the second connection area 3140*p*2 connected to the first forward wire 3111 and the second forward wire 3112. By the force, the working member 3140 moves further in the same direction (K1) as the second direction (D2), in other words, moves forward to a location further than FIG. 18B. As illustrated in FIG. 18C, the working member 3140 moves forward to a location further than FIG. 18B.

Although not illustrated, the form corresponding to the side view explaining the operation of the working member described above may be applied as is or by modifying the same within an appropriate range in the case of the end tool 3100 of an embodiment of the present disclosure.

FIGS. 19 and 20 are diagrams illustrating an optional embodiment in which backward wire is added to the end tool of FIG. 1.

Referring to FIGS. 19 and 20, the end tool of an embodiment of the present disclosure may further include the backward wire (BRW).

For example, the structure of FIG. 19 may be a case in which the backward wire (BRW) is further added to the structure of FIG. 17.

Referring to FIGS. 19 and 20A to 20C, for convenience of explanation, the first jaw 3101 is excluded, and the first forward wire 3111, the second forward wire 3112, the first fixed pulley 3121, the second fixed pulley 3122, the working member 3140, and the backward wire (BRW) are illustrated.

Figure 20A:
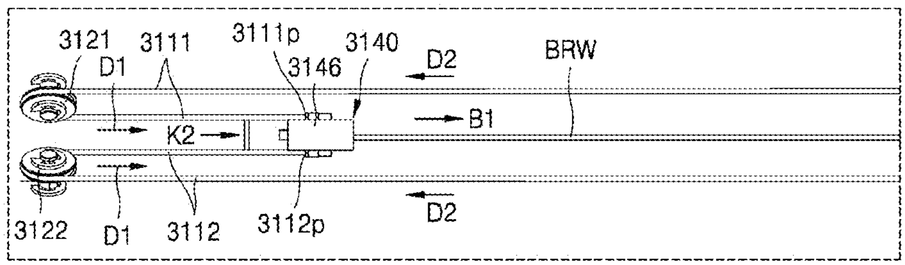
Figure 20B:
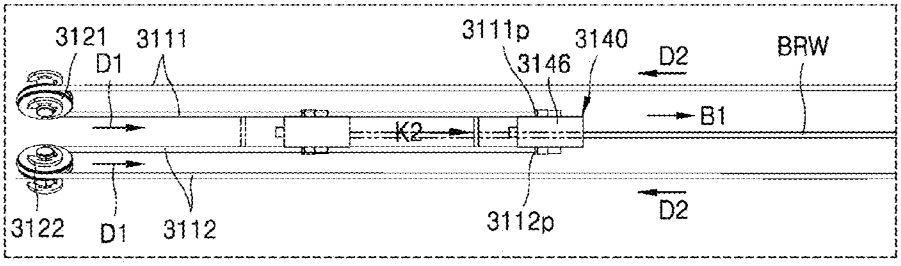
Figure 20C:
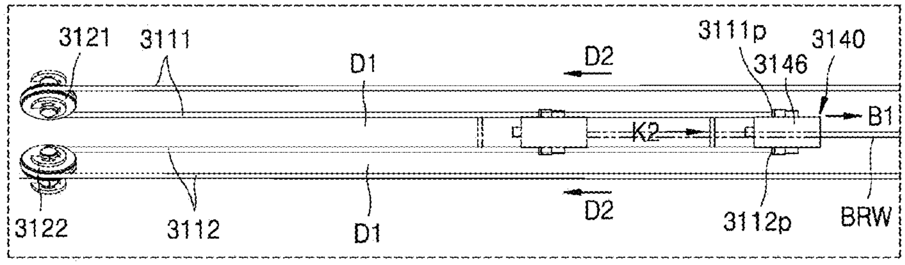

Referring to FIG. 19, the working member 3140 may move in the right direction, in other words, move backward in the direction of the proximal unit 3101*p*, and this backward movement is sequentially illustrated in FIGS. 20A, 20B, and 20C.

The backward wire (BRW) may be connected to an area of the working member 3140, for example, the rear of the working member, as a specific example, the opposite surface of an edge forming area of the blade area 3142*a* among the areas of the main body 3142.

The driving unit or a driving transmission unit (for example, a wire or a pulley, etc.) that may pull the backward wire (BRW) may be connected to the backward wire (BRW), and the backward wire (BRW) may be operated according to manual or automatic manipulation. For example, the backward wire (BRW) may be pulled by the manipulation unit 3200 (FIG. 1).

By pulling the backward wire (BRW), the working member 3140 may move backward.

For example, as illustrated in FIG. 20A, when the working member 3140 pulls the backward wire (BRW) in a backward direction (B1) while being adjacent to the distal unit (3101*d*) of the first jaw 3101, the working member 3140 connected to the backward wire (BRW) moves backward in the same direction (K2).

In this connection, the first forward wire 3111 and the second forward wire 3112 may be in a state where no pulling force is applied.

When the working member 3140 moves backward (K2), the areas of the first forward wire 3111 and the first forward wire 3112 connected to the first connection area 3140*p*1 and the second connection area 3140*p*2 of the working member 3140 move in the same direction (D1), and the areas of the first forward wire 3111 and the second forward wire 3112 wound downward and disposed upward through the first fixed pulley 3121 and the second fixed pulley 3122 may move in the opposite direction (D2). Accordingly, the working member 3140 is in the location of FIG. 20B, having moved backward so as to be adjacent to the proximal unit 3101*p* than FIG. 20A.

Then, as illustrated in FIG. 20B, when the backward wire (BRW) is further pulled in the backward direction (B1), the working member 3140 connected to the backward wire (BRW) moves backward in the same direction (K2). In this connection, the first forward wire 3111 and the second forward wire 3112 may be in a state where no pulling force is applied. The areas of the first forward wire 3111 and the second forward wire 3112 connected to the first connection area 3140*p*1 and the second connection area 3140*p*2 of the working member 3140 may move in the same direction (D1), and the areas of the first forward wire 3111 and the second forward wire 3112 wound downward and disposed upward through the first fixed pulley 3121 and the second fixed pulley 3122 may move in the opposite direction (D2). Accordingly, the working member 3140 is in the location of FIG. 20C, having moved backward so as to be adjacent to the proximal unit 3101*p* than FIG. 20*b*.

In addition, although not illustrated, the aforementioned configuration may be selectively applied to the end tool 3100 of an embodiment of the present disclosure.

The cartridge 3500 accommodated in the end tool 3100 of FIG. 2 and the staple operation will be described in more detail.

FIG. 21 is a perspective view of the first jaw and cartridge of the surgical instrument of FIG. 1.

Referring to FIGS. 1, 2, 3, 4, and 21, the cartridge 3500 may be disposed in the first jaw 3101, and for example, the cartridge 3500 may be disposed by being coupled to the cartridge accommodation unit 3101*a* of the first jaw 3101. For example, the cartridge 3500 may be formed integrally with the first jaw 3101 while the working member 3140 is disposed in the first jaw 3101. In addition, as an optional embodiment, the cartridge 3500 may be formed so as to be mountable and detachable from the first jaw 3101.

The cartridge 3500 includes the plurality of staples 3530 inside to perform tissue suturing and perform cutting through the working member 3140. Herein, the cartridge 3500 may include a cover 3510, the staple 3530, and the withdrawal member 3535.

The cover 3510 may be formed to cover an upper portion of the cartridge accommodation unit 3101*a* of the first jaw 3101. The cover 3510 may be formed with staple holes 3510*s* through which the plurality of staples 3530 may be discharged to the outside. Before the stapling operation, the staples 3530 accommodated inside the cartridge accommodation unit 3101*a* are pushed upward by the working member 3140 during the stapling operation, and are withdrawn to the outside of the cartridge 3500 through the staple holes 3510*s* of the cover 3510, so that stapling may be performed.

The cover 3510 may be formed with a slit 3510*w* along its length direction. The blade area 3142*a* of the main body 3142 of the working member 3140 may protrude to the outside of the cartridge 3500 through the slit 3510*w*. As the blade of the main body 3142 of the working member 3140 passes along the slit 3510*w*, the tissue on which stapling has been completed may be cut.

As an optional embodiment, the cartridge 3500 may include the case 3520, and after the case 3520 is disposed in the cartridge accommodation unit 3101*a* of the first jaw 3101, the cartridge 3500 may be disposed in the case 3520.

The plurality of staples 3530 may be disposed inside the cartridge accommodation unit 3101*a* of the first jaw 3101. As the working member 3140 moves linearly in one direction, the plurality of staples 3530 are sequentially pushed up from the inside to the outside of the cartridge accommodation unit 3101*a* of the first jaw 3101, so that suturing, in other words, stapling, may be performed. Herein, the material of the staples 3530 may include a material that is durable and does not have an abnormal effect on the human body, and may include, for example, titanium, stainless steel, etc.

The withdrawal member 3535 may be further disposed between the staples 3530 and the cartridge accommodation unit 3101*a* of the first jaw 3101. In other words, it may be expressed that the staples 3530 are disposed on an upper portion of the withdrawal member 3535. In this connection, the working member 3140 moves linearly in one direction to push up the withdrawal member 3535, and this withdrawal member 3535 may push up the staples 3530.

As such, the working member 3140 pushes up the staples 3530 including both the case where the working member 3140 directly pushes up the staples 3530 and the case where the working member 3140 pushes up the withdrawal member 3535 so that the withdrawal member 3535 pushes up the staples 3530 (in other words, the working member 3140 indirectly pushes up the staples 3530).

As described above, the working member 3140 may be disposed inside the cartridge accommodation unit 3101*a* of the first jaw 3101. In addition, the working member 3140 may include the wedge (WDG) or may be used together with the wedge (WDG). The wedge (WDG) may move together with the movement of the working member 3140 so that the wedge (WDG) may directly push up the staple 3530, or the wedge (WDG) may push up the withdrawal member 3535 to push up the staple 3530.

As described above, the motion of the first forward wire 3111 and the second forward wire 3112, in other words, the pulling of the first forward wire 3111 and the second forward wire 3112, may cause the working member 3140 connected thereto to move forward in the direction of the distal unit 3101*d* of the first jaw 3101.

Through the forward motion of the working member 3140, the wedge (WDG) pushes up the withdrawal member 3535, thereby raising the staple 3530, and simultaneously, cutting may be performed through a blade of the working member 3140. In addition, as an optional embodiment, in the case of the end tool that connects the backward wire (BRW) to the working member 3140, the working member 3140 may be moved backward in the direction of the proximal unit 3101*p* of the first jaw 3101 by pulling the backward wire (BRW).

FIGS. 22 and 23 are views of a switching pulley, a yaw pulley, and a pitch pulley of the end tool of the surgical instrument of FIG. 1.

As described above, the end tool 3100 may be connected to the connection unit 3400, and the end tool 3100 may rotate around one axis based on the connection unit 3400 and rotate around another axis.

For example, the end tool 3100 may perform a pitch motion, in other words, an up-and-down rotational motion as shown in FIGS. 2 and 21, and the end tool 3100 may perform a yaw motion, in other words, a left-right rotational motion as shown in FIGS. 2 and 21. The rotation axis of the pitch motion and the rotation axis of the yaw motion may be intersecting or orthogonal.

For example, the end tool 3100 may include one or more members connecting the jaw 3103 and the connection unit 3400, for example, the articulation member, and may include the end tool hub 3108 and the pitch hub 3107.

The end tool hub 3108 may be disposed to connect the straight line unit 3401 of the end tool 3100 and the connection unit 3400. For example, the end tool hub 3108 may correspond to the pulley axis (JX4), and this pulley axis (JX4) may be a rotation axis of the pitch motion.

As a specific example, the end tool 3100 may rotate around the pulley axis (JX4), the pitch hub 3107 may rotate around the pulley axis (JX4), and the jaw 3103 may be connected to the pitch hub 3107 and may perform a rotational motion, in other words, a pitch motion, around the pulley axis (JX4) as an integral part of the pitch hub 3107.

The pitch hub 3107 may be connected to the end tool hub 3108 and the jaw 3103, and may be axially coupled with the end tool hub 3108 based on the pitch pulley axis (JX4) to rotate around the pulley axis (JX4). In addition, the jaw 3103 may be axially coupled with the pitch hub 3107 based on the one pulley axis (JX1). The jaw 3103 may rotate around the one pulley axis (JX1) while being connected to the pitch hub 3107, in other words, perform a yaw motion.

In addition to the pulley axis for the articulation motion of the end tool 3100, in other words, the pulley axis (JX4) for the pitch motion and the pulley axis (JX1) for the yaw motion, an auxiliary pulley axis may additionally be disposed.

For example, another pulley axis (JX2) is disposed adjacent to and parallel to the pulley axis (JX1) on the pitch hub 3107. The pulley axis (JX2) may have an axis parallel to the pulley axis (JX1), and the pulley axis (JX2) may be disposed further from the working member 3140 than the pulley axis (JX1) is, in other words, closer to the connection unit 3400.

In addition, the pulley axis (JX3) may be disposed adjacent to the pulley axis (JX4). Additionally, the pulley axis (JX5) may be further disposed.

For example, the pulley axis (JX3) and the pulley axis (JX5) may be disposed on both sides of the pulley axis (JX4) interposed therebetween, and the pulley axis (JX3) and the pulley axis (JX5) may have an axis parallel to the pulley axis (JX4).

As a specific example, the pulley axis (JX3) may be disposed between the pulley axis (JX2) and the pulley axis (JX4), and may have an axis that is oriented intersecting or orthogonal to the pulley axis (JX2) and the pulley axis (JX1). The pulley axis (JX5) may be disposed further from the working member 3140 than the pulley axis (JX4) is, in other words, closer to the connection member 3400.

One or more switching pulley axes (AX1, AX2), in other words, a first switching pulley axis (AX1) and a second switching pulley axis (AX2), may be disposed and may be disposed closer to the working member 3140 than the pulley axes (JX1, JX2, JX3, JX4, JX5) are.

The first switching pulley axis (AX1) and the second switching pulley axis (AX2) may be formed parallel to each other, and may be disposed to be misaligned with respect to the width direction of the first jaw 3101. The first switching pulley axis (AX1) and the second switching pulley axis (AX2) may be disposed sequentially along a direction toward the distal unit 3101*d* of the first jaw 3101, and may be disposed so that some areas overlap.

One or more pulleys may be disposed on the pulley axes (JX1, JX2, JX3, JX4, JX5) and the switching pulley axes (AX1, AX2).

When explaining in order along a direction toward the connection unit 3400 in the proximal unit of the first jaw 3101, one or more switching pulleys (AXP1) corresponding to the first switching pulley axis (AX1) and one or more switching pulleys (AXP2) corresponding to the second switching pulley axis (AX2) are disposed.

At least one switching pulley (AXP1) corresponding to the first switching pulley axis (AX1) and at least one switching pulley (AXP2) corresponding to the second switching pulley axis (AX2) may be disposed in a location overlapping the first jaw 3101, and may be disposed, for example, in an area of the coupling area 3101*z* of the first jaw 3101 so as not to overlap with the pitch hub 3107.

The path may be guided while at least one area of the first forward wire 3111 and the second forward wire 3112 contacts the switching pulley (AXP1) and the switching pulley (AX2), respectively.

For example, the first forward wire 3111 may enter the switching pulley (AXP1) from the outside, be wound inward, and be wound out to an area of the switching pulley (AXP2) adjacent thereto.

The path may be guided by contacting at least one area of the second forward wire 3112 with the switching pulley (AXP2), and the first forward wire 3111 and the second forward wire 3112 gathered in the switching pulley (AXP2) may be wound in the same direction on one or more pulleys (JXP1) corresponding to the pulley axis (JX1) described later in the same direction.

Thus, the first forward wire 3111 and the second forward wire 3112 may be moved in one direction, and each articulation motion, for example, the pulley axis and pulleys for the pitch motion and the pulley axis and pulleys for the yaw motion may be gathered and organized on one side instead of both sides. In addition, it is possible to precisely implement simultaneous and easy control of the first forward wire 3111 and the second forward wire 3112.

For example, when the end tool 3100 performs yaw or pitch motion, the wires wrapped around the yaw pulley (pulley for yaw motion) or the pitch pulley (pulley for pitch motion) are wound or unwound to one side, and the first forward wire 3111 and the second forward wire 3112 of an embodiment of the present disclosure are gathered at one side; in other words, the wires may be wound in the same direction around the yaw pulley and the pitch pulley, and are wound or unwound by the same distance. Accordingly, in order to perform yaw or/pitch manipulation so that the working member 3140 does not move, the first forward wire 3111 and the second forward wire 3112 only need to be wound or unwound by the same distance, so that the two wires may be easily controlled together with one driving unit (for example, an actuator).

As an optional embodiment, the first forward wire 3111 and the second forward wire 3112 may be wound in different directions around the yaw pulley and the pitch pulley, respectively. When the first forward wire 3111 or the second forward wire 3112 is pulled, an unwanted rotational force may be generated in the end tool 3100. This may be caused by the asymmetrical application of force since the first forward wire 3111 and the second forward wire 3112 are offset by the radius of the yaw pulley or the pitch pulley, respectively. In this connection, when the first forward wire 3111 and the second forward wire 3112 are wound in opposite directions around the yaw pulley and the pitch pulley, respectively, the rotational force to the end tool 3100 may be offset through the symmetrical application of force, and thereby the shaking or location/position change of the end tool 3100 during the stapling process may be reduced. In this connection, since the first forward wire 3111 and the second forward wire 3112 may be wound on one side and unwound on the other side, a compensation member may be additionally disposed to compensate therefor. For example, a common pulley may be disposed in an area of the end tool 3100, the connection unit 3400 adjacent thereto, or the manipulation unit 3200 to form the first forward wire 3111 and the second forward wire 3112 into a single loop. As another example, the first forward wire 3111 and the second forward wire 3112 may be manipulated by separate driving units (for example, actuators).

In order to facilitate a path guidance of the first forward wire 3111 and the second forward wire 3112, the switching pulley (AXP1) and the switching pulley (AXP2) may have a structure that is symmetrical to each other with respect to the extension line of the working member 3140, in other words, offset by the same distance based on the extension line of the working member 3140. Thus, the size of the switching pulley (AXP1) and the switching pulley (AXP2) may be increased to improve the efficiency and stability of the path guide of the first forward wire 3111 and the second forward wire 3112.

At least one pulley (JXP1) is disposed to correspond to the pulley axis (JX1), and at least one pulley (JXP2) is disposed to correspond to the pulley axis (JX2) adjacent thereto. The pulley (JXP1) and the pulley (JXP2) may include parallel axes.

For example, the pulley (JXP1) and the pulley (JXP2) are disposed on the first hub 3107*a* (FIG. 5) of the pitch hub 3107. One or more pulleys (JXP2) guide the path of driving of wires disposed corresponding to one or more pulleys (JXP1) to secure a smooth path toward the pulley axis (JX4) or, more closely, the pulley axis (JX3) and the corresponding pulley (JXP3).

In addition, one or more pulleys (JXP3) are disposed corresponding to the pulley axis (JX3), and one or more pulleys (JXP4) corresponding to the pulley axis (JX4) are disposed adjacent thereto. For example, the pulley (JXP3) and the pulley (JXP4) are disposed on the second hub 3107*b* (FIG. 54) of the pitch hub 3107. In addition, one or more pulleys (JXP5) may be disposed corresponding to the pulley axis (JX5). The pulley (JXP3), the pulley (JXP4) and the pulley (JXP5) may include parallel axes, and may include axes intersecting or orthogonal to the pulley (JXP1) and the pulley (JXP2).

As illustrated in FIGS. 22 and 23, the paths of the first forward wire 3111 and the second forward wire 3112 may be precisely controlled to maximize the driving efficiency and control characteristics of the working member 3140 through the first forward wire 3111 and the second forward wire 3112.

As described above, the first switching pulley (AXP1) and the second switching pulley (AXP1) are disposed forward, in other words, closer to the working member 3140, than the pulley axis (JX4) is for the pitch motion and the pulley axis (JX1) for the yaw motion, which are two articulation motions of the end tool 3100.

As a specific example, the first switching pulley (AX1) and the second switching pulley (AX2) are disposed forward, in other words, closer to the working member 3140, than the pulley (JXP4) corresponding to the pulley axis (JX4) for the pitch motion, the pulley (JXP1) corresponding to the pulley axis (JX1) for the yaw motion, the pulleys (JXP3) and (JXP5) corresponding to the pitch auxiliary pulley, and the pulley (JXP2) which is the yaw auxiliary pulley are.

As a result, the first switching pulley (AX1) and the second switching pulley (AX2) may be disposed forward, in other words, closer to the working member 3140 than the pulleys (JXP1), (JXP2), (JXP3), (JXP4), and (JXP5) are.

Thus, the first forward wire 3111 enters the switching pulley (AXP1) from the outside, is wound inward, and is wound into an area of the switching pulley (AXP2) adjacent thereto, and the first forward wire 3111 and the second forward wire 3112 may be gathered together on one side of the switching pulley (AXP2), for example, on the outside.

In addition, the first forward wire 3111 and the second forward wire 3112 gathered together on the outside of the switching pulley (AXP2) may simultaneously correspond to the outside of the pulley (JPX1) corresponding to the pulley axis (JX1), which is the yaw pulley axis, and after the path is changed, are wound around the pulley (JXP2) corresponding to the pulley axis (JX2), which is the yaw auxiliary pulley axis. Then, after the path is changed, the height of the path may be controlled by the pulley (JXP3) corresponding to the pulley auxiliary axis (JX3), and then the first forward wire 3111 and the second forward wire 3112 may stably correspond to the lower side of the pulley (JXP4) corresponding to the pulley (JX4), which is the pitch axis, and then may pass through the pulley (JXP5) toward the connection unit 3400.

In other words, by primarily bringing the first forward wire 3111 and the second forward wire 3112 together through the switching pulley (AXP1) and the switching pulley (AXP2), the first forward wire 3111 and the second forward wire 3112 may be easily guided along the path by simultaneously corresponding to the rotation axis and the pulley for the articulation motion of the end tool 3100 and the pulley assisting the same, thereby improving the accuracy and stability of the forward motion of the working member 3140.

In addition, the height of the path is controlled by the pulley (JXP3) before the first forward wire 3111 and the second forward wire 3112 gathered together head toward the pulley (JXP4) corresponding to the pitch axis of the pulley (JX4), so that the first forward wire 3111 and the second forward wire 3112 may be stably wound around the pulley (JXP4) corresponding to the pitch axis of the pulley (JX4), and the degree of freedom in the size, design, and disposition of the pulley (JXP4) may be improved.

As an optional embodiment, the backward wire (BRW) may be further disposed as described, in which case the backward wire (BRW) may pass between the switching pulley (AXP1) and the switching pulley (AXP2) or pass therebetween while contacting the common area of the switching pulley (AXP1) and the switching pulley (AXP2) and then pass therebetween while corresponding to the other pulleys (JXP1, JXP2, JXP3, JXP4, JXP5).

For example, the backward wire (BRW) may correspond to the switching pulley disposed on an axis parallel to or the same as at least one of the switching pulley axes (AX1, AX2). As a specific example, the backward wire (BRW) may be disposed on the switching pulley axes (AX1, AX2) and pass therebetween in a corresponding manner to one or more pulleys opposing the switching pulley (AXP1) or the switching pulley (AXP2).

The backward wire (BRW) may be wound in the opposite direction with respect to the pulleys (JXP1, JXP2) around which the first forward wire 3111 and the second forward wire 3112 are wound. For example, when the first forward wire 3111 and the second forward wire 3112 are wound backward with respect to the pulley (JXP1) and forward with respect to the pulley (JXP2), the backward wire (BRW) may be wound forward with respect to the pulley (JXP1) and backward with respect to the pulley (JXP2). Thus, the first forward wire 3111 and the second forward wire 3112 may be wound on one side and the backward wire (BRW) on the other side for one or more pulley axles. When at least one of the first forward wire 3111 and the second forward wire 3112 and the backward wire (BRW) forms a closed loop, it is easy to maintain tension of the entire wire.

For example, when the yaw motion or pitch motion of the end tool is manipulated, the wire wound around the axis corresponding to the motion may be additionally wound or unwound depending on the wound direction. In this connection, when the forward wire 3111, 3112 and the backward wire (BRW) are wound in opposite directions, the backward wire (BRW) is unwound as much as the forward wire 3111, 3112 is wound, or the forward wire 3111, 3112 is unwound as much as the backward wire (BRW) is wound. As a result, the entire length of the closed loop of the forward wire 3111, 3112 and the backward wire (BRW) may be maintained, making it easy to maintain tension. In this connection, in order to additionally limit unnecessary movement of the working member 3140, the driving unit (for example, an actuator) may be used to pull the forward wire 3111, 3112 or the backward wire (BRW).

As an additional example, the way in which the closed loop of the forward wire 3111, 3112 and the backward wire (BRW) is formed may be in the form of the forward wire 3111, 3112 and the backward wire (BRW) being wound around the common pulley, and this common pulley may be fixed to the rotation axis of the rotating the driving unit (for example, an actuator).

When the first forward wire 3111 and the second backward wire 3112 of an embodiment of the present disclosure are pulled, a certain amount of rotational force may be generated in the end tool 3100 due to the tension thereof. As a result, the jaw 3103 biting the body tissue may be unbalanced or an unnecessary external force may be applied to the body tissue. In this connection, the pulleys of the end tool 3100 and the corresponding pulley axes slightly tilt or move, and as a result, the inner diameter edges of the pulleys dig into the pulley axes, thereby increasing the frictional force and solidifying the coupling between the pulley and the pulley axes. Thus, a frictional force that acts as resistance to the abnormal rotational force generated in the end tool 3100 is generated, thereby improving the stable usability of the end tool 3100. In addition, this may be applied even when the backward wire (BRW) is used, and may be applied as is to the embodiment described below and the embodiment described above.

This frictional force may be removed together when the tension applied to the first forward wire 3111 and the second backward wire 3112 or the backward wire (BRW) is removed.

Figure 24:
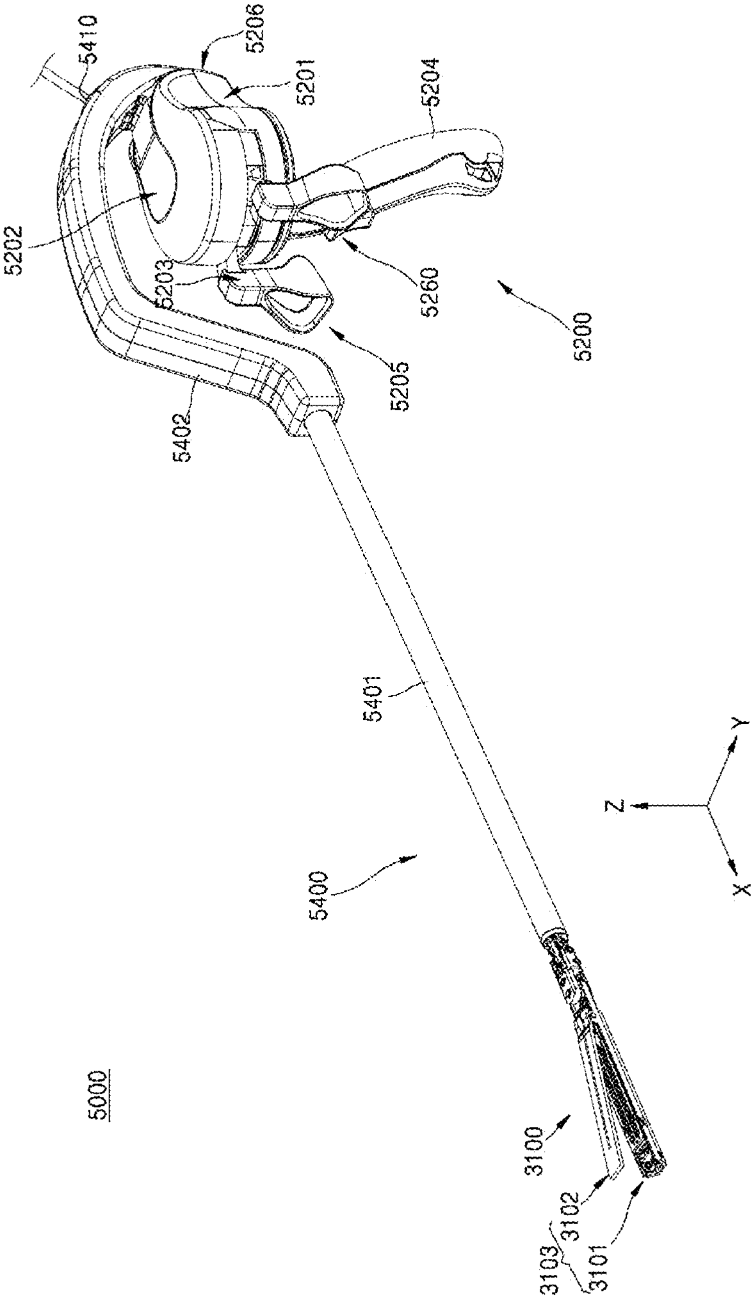
FIG. 24 is a schematic perspective view of a surgical instrument according to another embodiment of the present disclosure.
Figure 25:
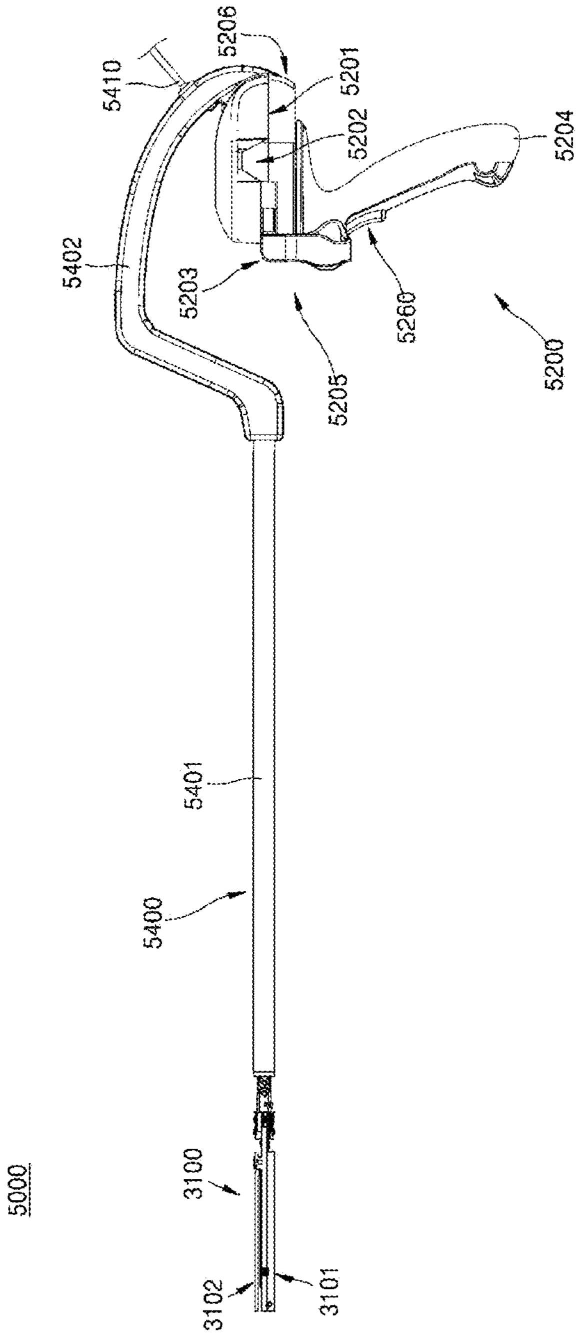
FIG. 25 is a side view of the surgical instrument of FIG. 24.
Figure 26A:
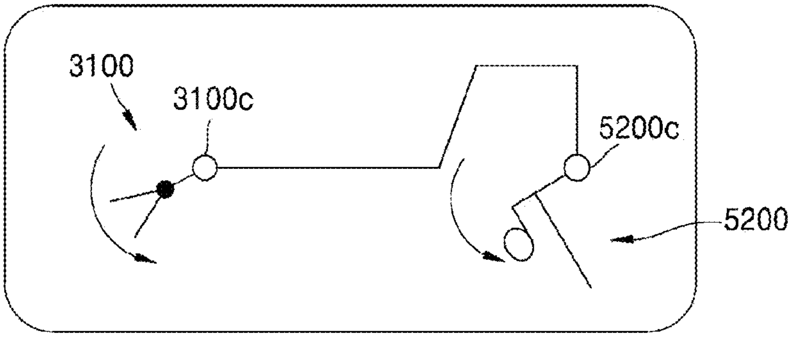
FIG. 26A to 26B is a diagram schematically illustrating the operation concept of the surgical instrument of FIG. 24.
Figure 26B:
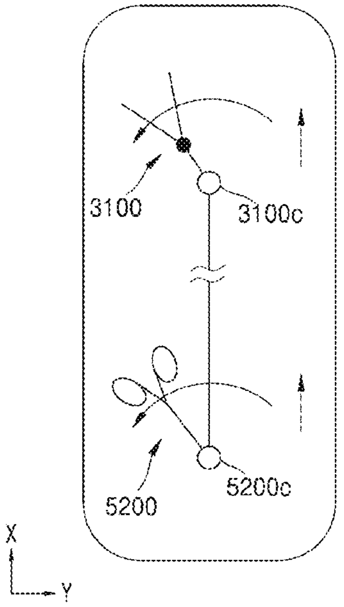

FIG. 24 is a schematic perspective view of a surgical instrument according to another embodiment of the present disclosure. FIG. 25 is a side view of the surgical instrument of FIG. 24. FIG. 26A to 26B is a diagram schematically illustrating the operation concept of the surgical instrument of FIG. 24.

Referring to FIGS. 24 and 25, a surgical instrument 5000 according to an embodiment of the present disclosure may include the end tool 3100, the manipulation unit 5200, the power transmission unit (not shown), and the connection unit 5400.

The end tool 3100 may include the end tool 3100 of the embodiment of FIG. 1 described above, so a detailed description thereof will be omitted. In addition, although not shown, as an optional embodiment, the surgical instrument 5000 may selectively apply one of the aforementioned end tools, and may also selectively apply the aforementioned modified examples. The end tool 3100 is illustrated only for the convenience of explanation.

The connection unit 5400 is formed in a hollow shaft shape, so that one or more wires and electric wires may be accommodated therein. The manipulation unit 5200 is coupled to one end of the connection unit 5400, and the end tool 3100 is coupled to the other end, so that the connection unit 5400 may perform a role of connecting the manipulation unit 5200 and the end tool 3100.

As an optional embodiment, the connection unit 5400 has a straight line unit 5401 and a bent unit 5402, wherein the straight line unit 5401 may be formed on the side coupled with the end tool 3100, and the bent unit 5402 may be formed on the side coupled with the manipulation unit 5200. As such, since the end of the manipulation unit 5200 of the connection unit 5400 is formed by being bent, a pitch manipulation unit 5201, a yaw manipulation unit 5202, and an actuation manipulation unit 5203 are formed on an extension line of the end tool 3100 or adjacent to the extension line thereof. In other words, it may be described that at least a portion of the pitch manipulation unit 5201 and the yaw manipulation unit 5202 are accommodated in a concave unit formed by the bent unit 5402. The shape of the bent unit 5402 may make the shapes and operations of the manipulation unit 5200 and the end tool 3100 more intuitively consistent.

The plane on which the bent unit 5402 is formed may be substantially the same plane as a pitch plane. In this way, since the bent unit 5402 is formed on a plane substantially the same as an XZ plane, interference between the manipulation units may be reduced. For the intuitive operation of the end tool and the manipulation unit, other types of configurations may be possible, in addition to the XZ plane.

As an optional embodiment, a connector 5410 may be formed on the bent unit 5402. The connector 5410 may be connected to an external power source (not shown), and further, the connector 5410 may be connected to the end tool 3100 via an electric wire, so as to transmit electric energy supplied from the external power source (not shown) to the end tool 3100.

The manipulation unit 5200 is formed at the one end portion of the connection unit 5400 and is provided with an interface that may be directly controlled by a medical doctor, for example, a handle 5204, a tong shape, a stick shape, a lever shape, or the like. When the medical doctor controls the manipulation unit 5200, the end tool 3100 connected to the corresponding interface and inserted into the body of a surgical patient performs certain operation, thereby performing surgery. Herein, although the manipulation unit 5200 is illustrated as being formed in the shape of a handle that may be rotated while inserting a finger, the idea of the present disclosure is not limited thereto, and various types of manipulation units that are connected to the end tool 3100 and manipulate the end tool 3100 are possible. In addition, various controls for the manipulation unit 5200 may be possible through one or more driving axes disposed in the direction from the distal unit 5205 to the proximal unit 5206 of the manipulation unit 5200.

In addition, the manipulation unit 5200 of the surgical instrument 5000 may further include a staple manipulation unit 5260 that performs stapling and cutting of the end tool 3100.

An embodiment of the present disclosure may be applied to a robot-driven type instead of a manual type that is directly controlled by a person. In this connection, the end tool 3100 may be connected directly to a robot or to a robot driving arm or other area through the connection unit 5400 instead of the manual type manipulation unit 5200.

The end tool 3100 of the surgical instrument 5000 according to an embodiment of the present disclosure is formed to be rotatable in at least one direction, and for example, may be formed to perform a pitch motion centered on a Y-axis, and simultaneously, a yaw motion and an actuation motion centered on the Z-axis.

Herein, each of the pitch, yaw, and actuation motions used in FIGS. 24 to 26 are defined as follows.

First, the pitch motion means a motion in which the end tool 3100 rotates up and down with respect to the extension direction (X-axis direction of FIG. 24) of the connection unit 5400, in other words, a motion in which the end tool 3100 rotates centered on the Y-axis of FIG. 24. In other words, the pitch motion means a motion in which the end tool 3100 formed by extending from the connection unit 5400 in the extension direction of the connection unit 5400 (X-axis direction of FIG. 24) rotates up and down around the Y-axis with respect to the connection unit 5400.

Next, the yaw motion means a motion in which the end tool 3100 rotates left and right with respect to the extension direction (X-axis direction) of the connection unit 5400, in other words, a motion in which the end tool 3100 rotates around the Z-axis. In other words, the yaw motion means a motion in which the end tool 3100 formed by extending from the connection unit 5400 in the extension direction (X-axis direction) of the connection unit 5400 rotates left and right around the Z-axis with respect to the connection unit 5400. In other words, the yaw motion means a motion in which two jaws 3001, 1002 formed on the end tool 3100 rotate in the same direction around the Z-axis.

The actuation motion means a motion in which the end tool 3100 rotates around the same rotation axis as the yaw motion, but the two jaws 3001, 1002 rotate in opposite directions while the jaws close or open. In other words, the actuation motion means a motion in which the two jaws 3001, 1002 formed on the end tool 3100 rotate in opposite directions around the Z axis.

The power transmission unit (not shown) connects the manipulation unit 5200 and the end tool 3100 to transmit the driving force of the manipulation unit 5200 to the end tool 3100, and may include a plurality of wires, pulleys, links, joints, and gears.

FIGS. 26A to 26B may explain an example of the operation of the surgical instrument 5000 of FIG. 24.

Specifically, referring to FIGS. 26A and 26B, the surgical instrument is characterized in that the end tool 3100 is formed in front of a rotation center 3100*c* of the end tool, and the manipulation unit 5200 is also formed in front of a rotation center 5200*c* of the manipulation unit, so that the operations of the manipulation unit 5200 and the end tool 3100 are intuitively consistent. When the characteristics are expressed in a different way, the surgical instrument according to an embodiment of the present disclosure is formed so that at least a portion of the manipulation unit may be closer to the end tool (than its own articulation) based on its own articulation at one or more moments during a manipulation process.

Since the surgical instrument according to an embodiment of the present disclosure moves based on the rotation center formed at the rear of both the end tool and the manipulation unit, the operations are intuitively consistent with each other in terms of structure. In other words, since the moving portion of the end tool moves based on the rotation center formed at the rear, and the moving portion of the manipulation unit also moves based on the corresponding rotation center formed at the rear, the operations are intuitively consistent with each other in terms of structure. As a result, a user can intuitively and quickly perform control of the direction of the end tool, and the possibility of making a mistake may be reduced.

As an optional embodiment, the surgical instrument applying the end tool of an embodiment of the present disclosure may be driven in various ways. For example, it may be applied to the embodiments both in which the front and rear of the central axis of the end tool are swapped, or the front and rear of the manipulation unit and its central axis are swapped.

Surgical Instrument—Power Transmission Unit

Hereinafter, the power transmission unit of the surgical instrument according to an embodiment of the present disclosure will be described.

Figure 27:
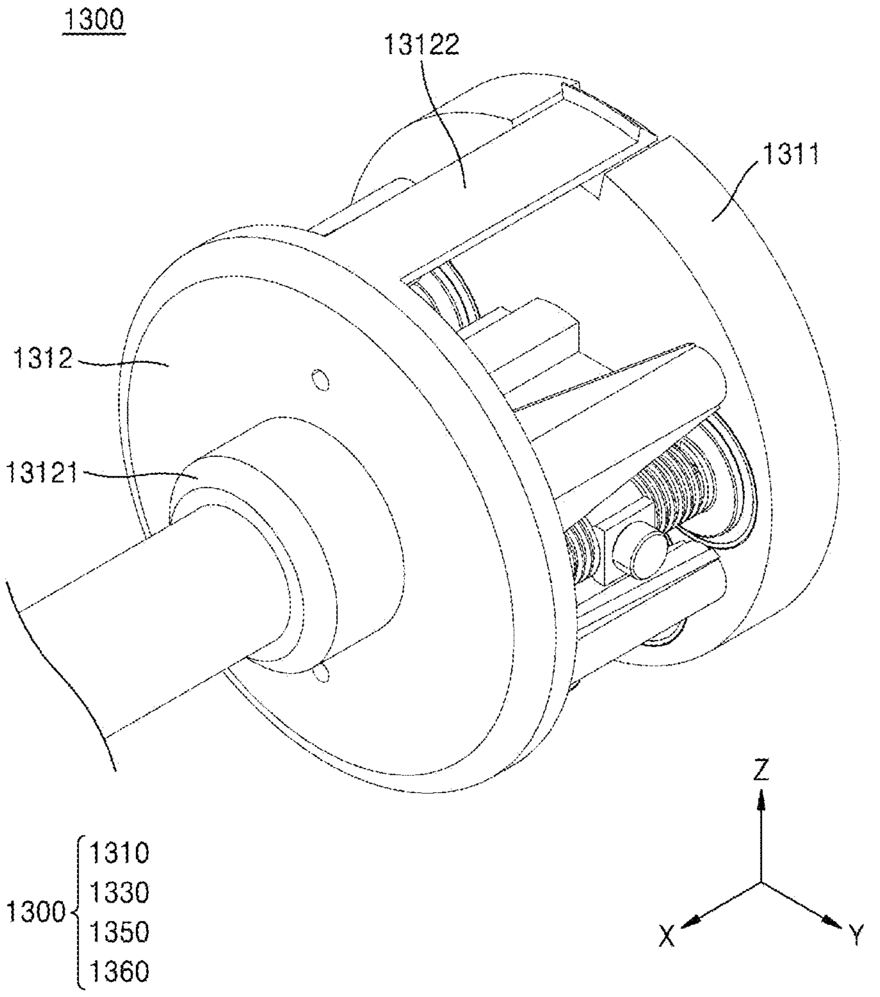
FIG. 27 is a perspective view of a power transmission unit and a shaft of the surgical instrument according to an embodiment of the present disclosure.
Figure 28:
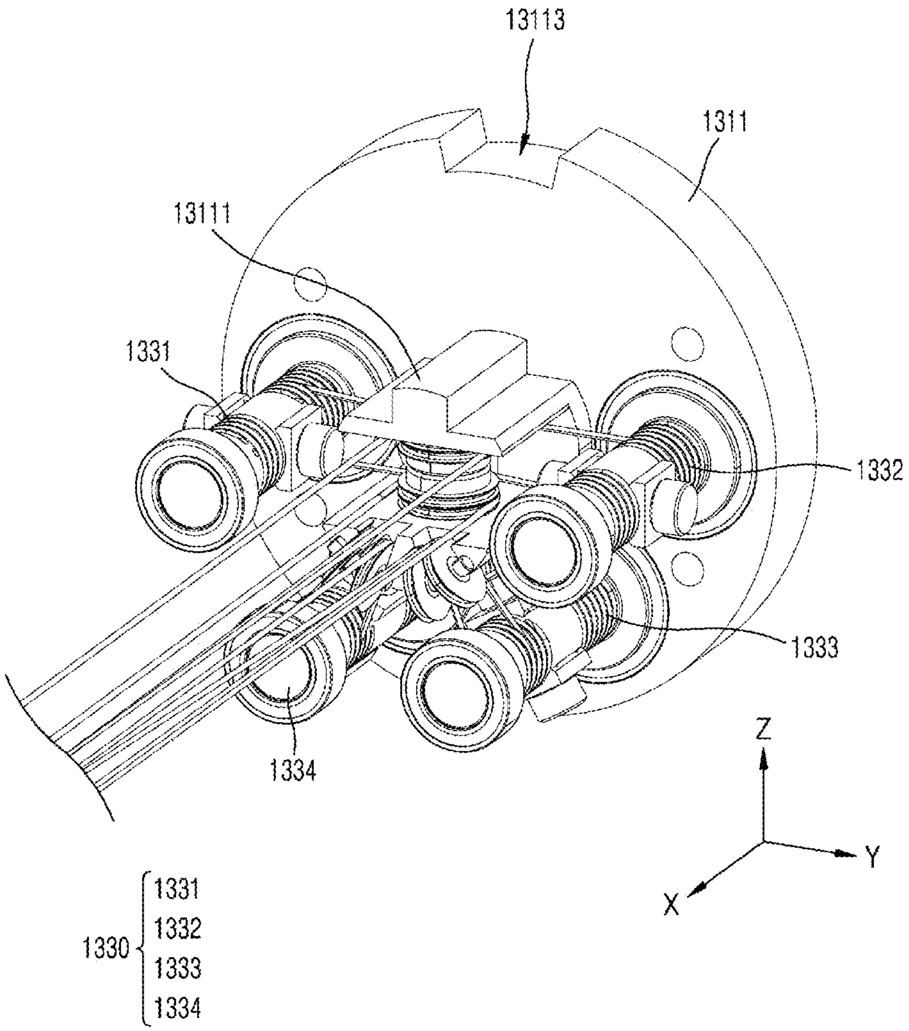
FIG. 28 is a diagram illustrating the internal structure of the power transmission unit according to a first embodiment of the present disclosure.
Figure 29:
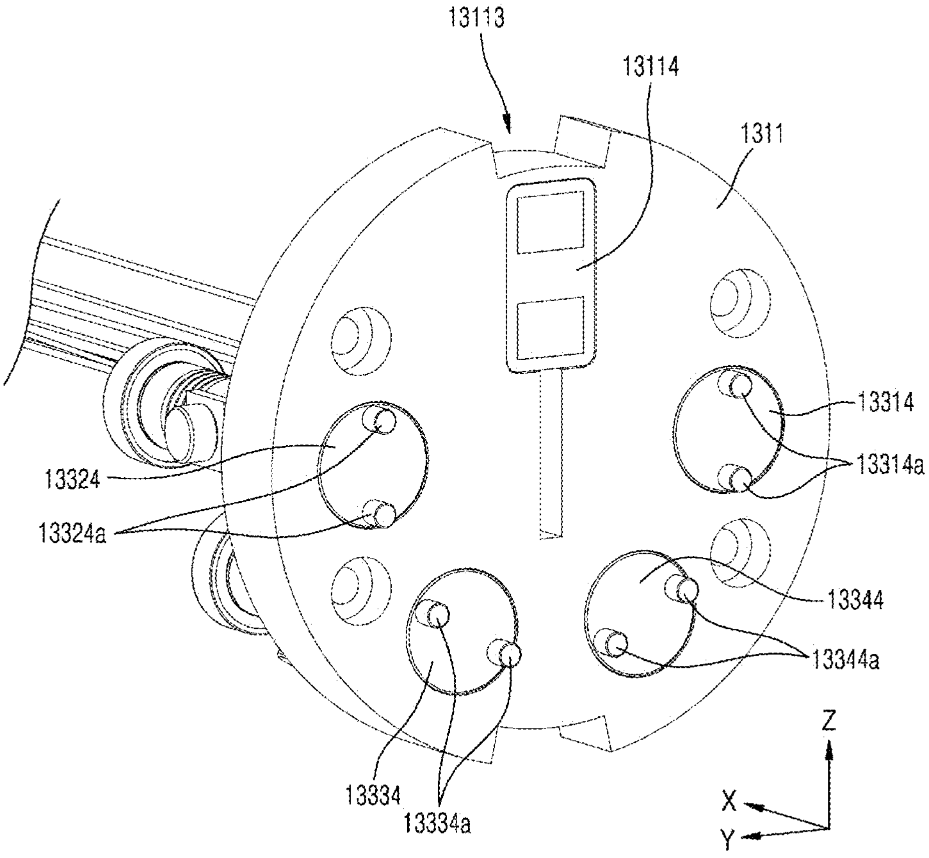
FIG. 29 is a diagram illustrating a view of the power transmission unit of FIG. 28 as seen from behind.
Figure 30:
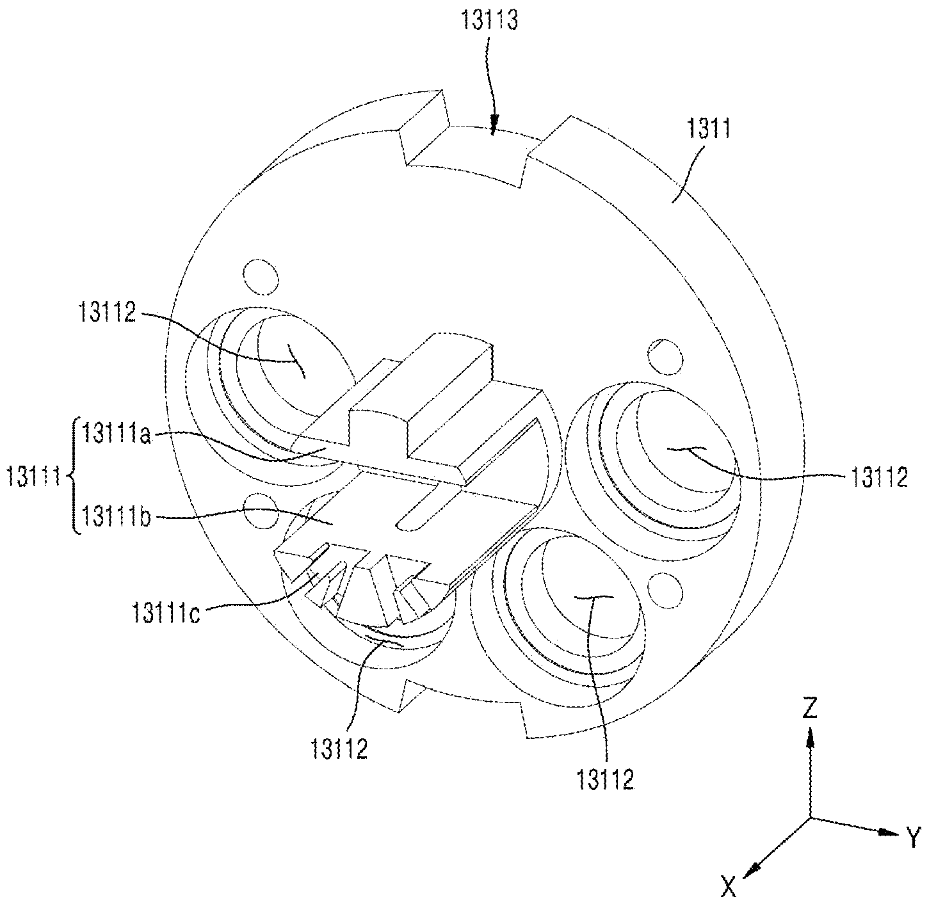
FIG. 30 is a perspective view of a first pulley frame of the power transmission unit of FIG. 28.
Figure 31:
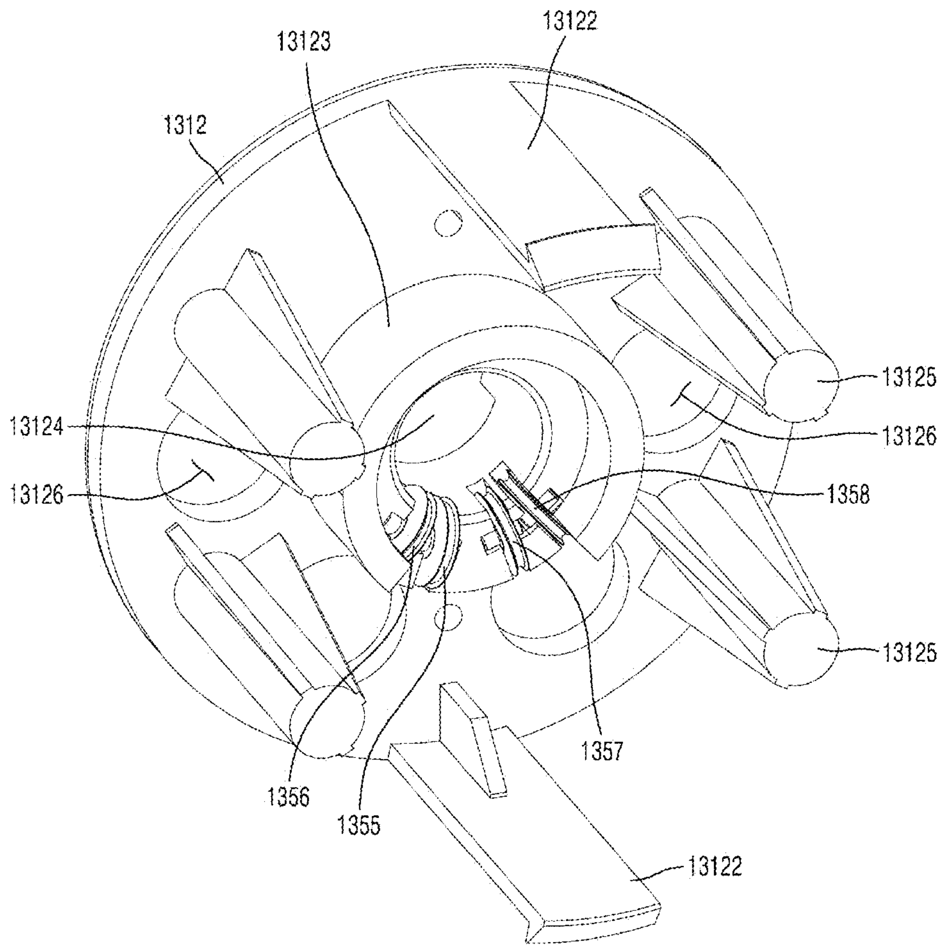
FIG. 31 is a perspective view of a second pulley frame of the power transmission unit of FIG. 27.
Figure 32:
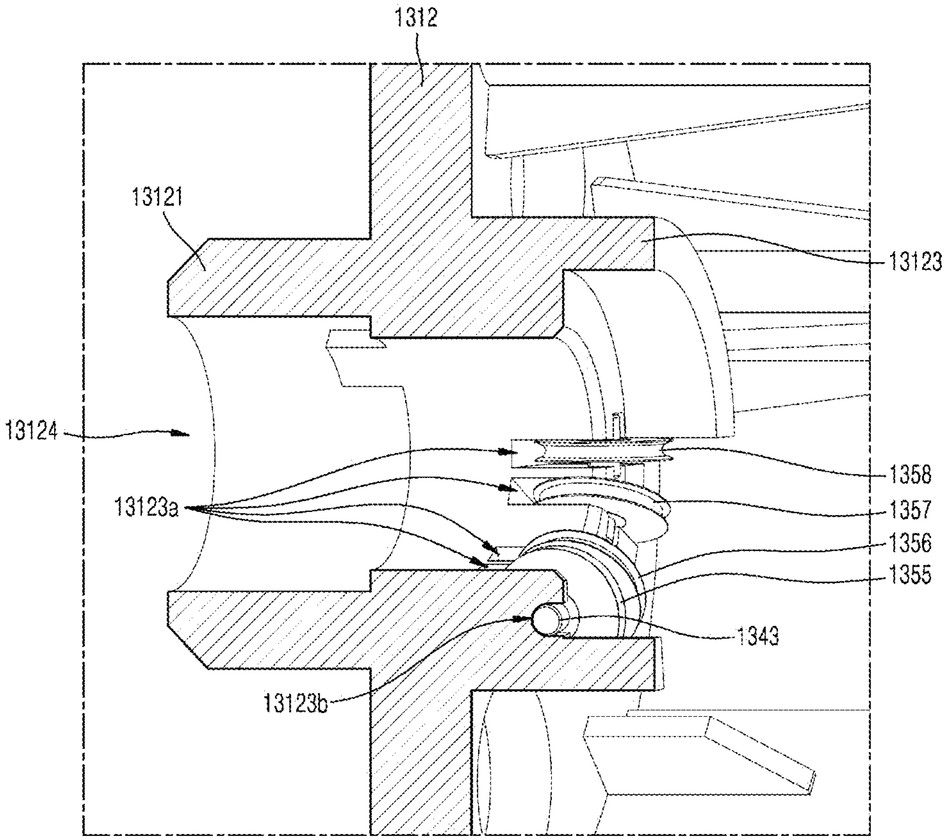
FIG. 32 is a cross-sectional perspective view of a side cross-section of the second pulley frame of FIG. 31.

FIG. 27 is a perspective view of a power transmission unit 1300 and a shaft of the surgical instrument according to an embodiment of the present disclosure. FIG. 28 is a diagram illustrating the internal structure of the power transmission unit 1300 according to a first embodiment of the present disclosure. FIG. 29 is a diagram illustrating a view of the power transmission unit 1300 of FIG. 28 as seen from behind. FIG. 30 is a perspective view of a first pulley frame 1311 of the power transmission unit 1300 of FIG. 28. FIG. 31 is a perspective view of a second pulley frame 1312 of the power transmission unit 1300 of FIG. 27. FIG. 32 is a cross-sectional perspective view of a side cross-section of the second pulley frame 1312 of FIG. 31.

Referring to FIGS. 27 to 32, the power transmission unit 1300 of the surgical instrument 3000 according to the first embodiment of the present disclosure may include a pulley frame 1310, a driving pulley unit, an auxiliary pulley unit, and a wire unit.

The driving pulley unit refers to a driving pulley itself or refers to a plurality of driving pulleys. In other words, the driving pulley unit may include a plurality of driving pulleys, and when explaining common content for each driving pulley, for the convenience of explanation, a representative driving pulley will be referred to as a driving pulley 1330.

Similarly, the wire unit may include a plurality of wires, and when explaining common content for each wire, for the convenience of explanation, a representative wire will be referred to as a wire 1360.

In addition, the auxiliary pulley unit may include a plurality of auxiliary pulleys, and when explaining common content for each auxiliary pulley, for the convenience of explanation, a representative auxiliary pulley will be referred to as an auxiliary pulley 1350.

The pulley frame 1310 may be connected to a power generation unit (not shown) described above. Specifically, the pulley frame 1310 is coupled with a housing of the manipulation unit 3200 and may be connected to the power generation unit provided in the manipulation unit 3200. Specifically, the pulley frame 1310 may be connected to a pulley coupling plate of the power generation unit, which will be described later. Thus, the pulley frame 1310 may play a role in supporting the driving pulley 1330 so that the driving pulley 1330 described later may be stably connected to a driving motor of the power generation unit. However, the idea of the present disclosure is not limited thereto, and other devices including a drape device may be interposed between the manipulation unit 3200 and the power transmission unit 1300 so that the power transmission unit 1300 may be connected to the other device and connected to the power generation unit.

In addition, the pulley frame 1310 may accommodate the driving pulley 1330 so as to rotate about its axis. Accordingly, the driving pulley 1330 may be connected to the driving motor and rotate by receiving the driving force generated from the driving motor. This will be described in detail later.

The pulley frame 1310 may include the first pulley frame 1311 and a second pulley frame 1312. Herein, the first pulley frame 1311 and the second pulley frame 1312 may be members that are coupled to each other.

The first pulley frame 1311 may be a portion that is coupled to the power generation unit as described above. In addition, the second pulley frame 1312 may be a portion to which a shaft 3400 is coupled.

From another perspective, the pulley frame 1310 may be interposed between the shaft 3400 and the power generation unit, and the first pulley frame 1311 may be disposed at the proximal unit and the second pulley frame 1312 may be disposed at the distal unit.

The first pulley frame 1311 may include a driving pulley coupling unit 13112 that accommodates at least a portion of the driving pulley 1330. The driving pulley coupling unit 13112 may be formed at a location corresponding to the driving motor (not shown) of the power generation unit. The driving pulley coupling unit 13112 may be formed in a hollow shape penetrating the first pulley frame 1311. Specifically, the hollow inner surface of the driving pulley coupling unit 13112 may be formed to accommodate a bearing 13303 of the driving pulley 1330.

In addition, the driving pulley coupling unit 13112 may be formed in plural numbers corresponding to the number of driving pulleys 1330. In addition, the plural driving pulley coupling units 13112 may be disposed symmetrically with respect to the center of the first pulley frame 1311.

The first pulley frame 1311 may form an auxiliary pulley fixing unit that accommodates at least a portion of the auxiliary pulley 1350.

In addition, the auxiliary pulley fixing unit may include a center auxiliary pulley fixing unit 13111 that is formed to extend from the first pulley frame 1311 toward the shaft 3400. In addition, the center auxiliary pulley, which will be described later, may be accommodated in the center auxiliary pulley fixing unit 13111.

Specifically, the center auxiliary pulley fixing unit 13111 may include an upper unit **13111*a* and a lower end unit 13111*b*. Herein, the upper unit 13111*a* and the lower end unit 13111*b* of the center auxiliary pulley fixing unit 13111 are formed to extend in a direction parallel to an axis of the shaft 3400 from the first pulley frame 1311, and the upper unit 13111*a* and the lower end unit 13111*b*** may be formed so that the opposing surfaces are parallel.

In addition, an auxiliary pulley rotation axis 1341 (FIG. 39) may be formed to accommodate at least a portion of the center auxiliary pulley by being coupled between the upper unit 13111*a* and the lower end unit 13111*b* of the center auxiliary pulley fixing unit 13111.

Referring to FIG. 30, a space may be formed in the lower end unit 13111*b* of the center auxiliary pulley fixing unit 13111 to accommodate a portion of an auxiliary pulley other than the center auxiliary pulley. From another perspective, an auxiliary pulley accommodation groove 13111*c* may be formed in the lower end unit 13111*b* of the center auxiliary pulley fixing unit 13111.

Figure 39:
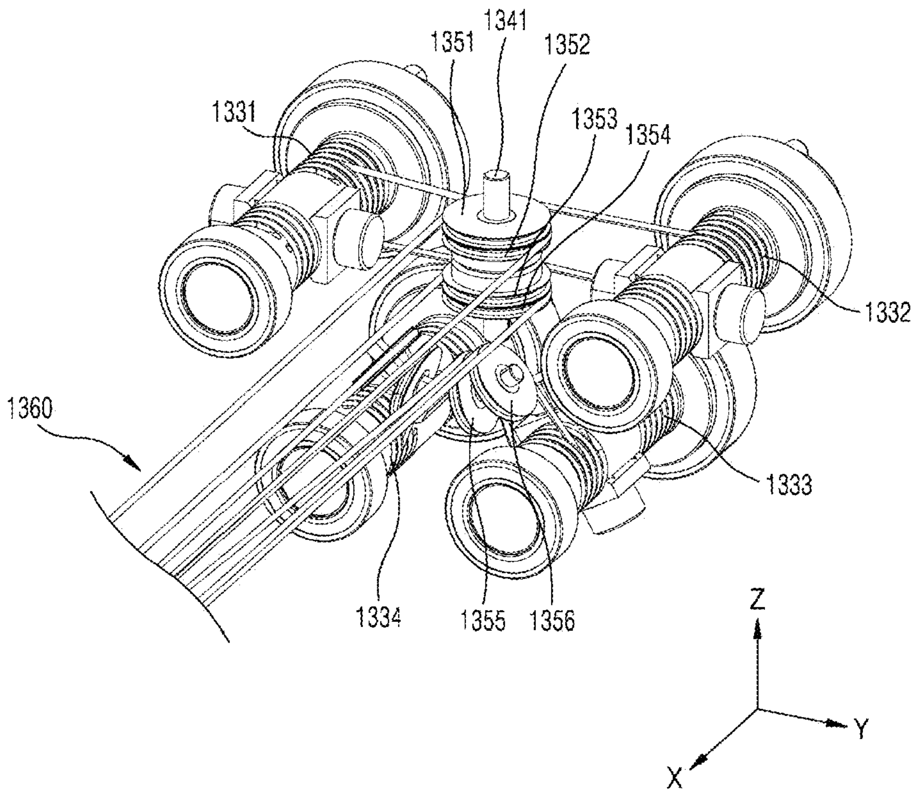
FIG. 39 is a perspective view of the state where the first pulley frame of the power transmission unit of FIG. 28 is removed.

Although an embodiment of the present disclosure has been described as having only a portion of the auxiliary pulley disposed in the lower end unit 13111*b* of the center auxiliary pulley fixing unit 13111, the idea of the present disclosure is not necessarily limited thereto, and the auxiliary pulley rotation axis 1341 (FIG. 39) may be formed to be coupled to the lower end unit 13111*b* of the center auxiliary pulley fixing unit 13111 so that the auxiliary pulleys 1355, 1356, 1357, 1358 rotate around the rotation axis 1341 (FIG. 39).

In addition, the center auxiliary pulley fixing unit 13111 may be formed to be coupled with an extension unit 13123 of a shaft coupling unit of the second pulley frame 1312 to be described later. Specifically, the center auxiliary pulley fixing unit 13111 may be formed to be inserted into the hollow formed by the extension unit 13123 of the shaft coupling unit. In other words, the outermost diameter of the center auxiliary pulley fixing unit 13111 may be smaller than the inner diameter of the extension unit 13123 of the shaft coupling unit.

The first pulley frame 1311 may form one or more fastening member accommodation grooves 13113 on a circumference of a side surface. The fastening member accommodation grooves 13113 may be formed to be capable of accommodating a fastening member 13122 that is formed by extending from the second pulley frame 1312. For example, the fastening member accommodation grooves 13113 may receive an end of the fastening member 13122. Specifically, the fastening member accommodation groove 13113 may be formed wider than the width of the fastening member 13122 and may be formed to have a certain depth so that the end of the fastening member 13122 may move in a thickness direction.

The first pulley frame 1311 may further include a data transmission/reception unit 13114 that may be electrically connected to the manipulating unit 3200 or another device on the rear surface opposite to the surface facing the second pulley frame 1312.

The data transmission/reception unit 13114 may further include a memory. The memory may store programs and instructions for processing and controlling a processor, and may also store data input from or output to a device.

For example, the memory may include a storage medium of at least one of a flash memory type, a multimedia card micro type, a card type memory (for example, an SD or XD memory, etc.), a random access memory (RAM), a static random access memory (SRAM), a read-only memory (ROM), an electrically erasable programmable read-only memory (EEPROM), and a programmable read-only memory (PROM).

The data transmission/reception unit 13114 may read and write data, store information related to the end tool 3100, and provide information to prevent reuse. For example, information including the length of the entire reload including the end tool 3100, the shaft 3400, and the power transmission unit 1300, the specifications of the reload including the type of the end tool 3100, and the number of times the reload has been used may be stored.

Referring to FIG. 31 and FIG. 32, the second pulley frame 1312 may include a shaft coupling unit 13121, the extension unit 13123 of the shaft coupling unit, a fastening member 13122, and a driving pulley coupling unit 13126.

The shaft coupling unit 13121 may be formed to protrude toward the distal unit from the second pulley frame 1312. In addition, the shaft coupling unit 13121 may form a shaft insertion hole 13124 that accommodates at least a portion of the shaft 3400. Herein, the shaft insertion hole 13124 may be formed to penetrate the second pulley frame 1312. In other words, an inner diameter of the shaft coupling unit 13121 may be formed to correspond to an outer diameter of the shaft 3400 so that the shaft 3400 may be fitted therein, and the end of the shaft 3400 may be inserted into the shaft coupling unit 13121.

In addition, the second pulley frame 1312 may have the extension unit 13123 of the shaft coupling unit formed on the opposite surface of the surface on which the shaft coupling unit 13121 is formed. In other words, the extension unit 13123 of the shaft coupling unit may be formed to protrude toward the proximal unit. In addition, the extension unit 13123 of the shaft coupling unit may form a hollow space therein. From another perspective, the shaft coupling unit 13121 may be formed on the front and rear surfaces of the second pulley frame 1312 so that the shaft coupling unit 13121 may be formed as if penetrating the second pulley frame 1312. However, the idea of the present disclosure is not limited thereto, and the extension unit 13123 of the shaft coupling unit may be formed in various shapes.

In addition, as described above, the extension unit 13123 of the shaft coupling unit may be coupled with the center auxiliary pulley fixing unit 13111 of the first pulley frame 1311. Specifically, the extension unit 13123 of the shaft coupling unit may be formed to accommodate the center auxiliary pulley fixing unit 13111 in a hollow interior. In other words, an inner diameter of the extension unit 13123 of the shaft coupling unit may be formed to be larger than an outermost diameter of the center auxiliary pulley fixing unit 13111.

As illustrated in FIG. 32, the extension unit 13123 of the shaft coupling unit may form an auxiliary pulley accommodation groove 13123*a* and a rotation axis fixing groove 13123*b*. The auxiliary pulley accommodation groove 13123*a* may be formed to accommodate at least a portion of the auxiliary pulley 1355, 1356, 1357, 1358, and the rotation axis fixing groove 13123 may be formed to accommodate the auxiliary pulley rotation axis 1342, 1343, 1344, 1345.

Specifically, the auxiliary pulley accommodation groove 13123*a* may be formed in a slit shape corresponding to the thickness of the auxiliary pulley 1355, 1356, 1357, 1358.

The rotation axis fixing groove 13123*b* may be formed as a structure that is laterally open so that the auxiliary pulley rotation axis 1342, 1343, 1344, 1345 is fixed in the direction of a rotation axis but may move laterally.

The rotation axis fixing groove 13123*b* and the auxiliary pulley accommodation groove 13123*a* may be formed along the circumference of the shaft insertion hole 13124. The auxiliary pulley rotation axis 1342, 1343, 1344, 1345 is disposed to be perpendicular to the central axis of the shaft 3400, but each auxiliary pulley rotation axis 1342, 1343, 1344, 1345 may not be parallel.

The fastening member 13122 of the second pulley frame 1312 may be a portion formed by extending from the second pulley frame 1312 as described above.

Specifically, the fastening member 13122 may be formed in a shape with a thin thickness relative to the length and width, and for example, the fastening member 13122 may be formed in a snap-fit structure.

In other words, the end of the fastening member 13122 may be formed in a hook shape so as to be coupled with a fastening groove formed in the manipulation unit 3200 or another device.

In addition, the fastening member 13122 may be formed so as to be at least partially accommodated in the fastening member accommodation groove 13113 of the first pulley frame 1311.

The second pulley frame 1312 may include a frame coupling unit 13125 that may be fixedly coupled with the first pulley frame 1311. The frame coupling unit 13125 may be formed to extend from the second pulley frame 1312 toward the first pulley frame 1311. For example, the frame coupling unit 13125 may be formed in a pillar shape, and a plurality of frame coupling units may be formed along the circumference of the second pulley frame 1312. Accordingly, the frame coupling unit 13125 may connect the first pulley frame 1311 and the second pulley frame 1312 so as to be coupled to each other, and may serve to support a side surface of the pulley frame 1310.

The driving pulley coupling unit 13126 formed on the second pulley frame 1312 may be formed at a location corresponding to the driving pulley coupling unit 13112 formed on the first pulley frame 1311.

Accordingly, one end of the rotation axis of the driving pulley 1330 or the driving pulley 1330 may be coupled to the first pulley frame 1311, and the other end may be coupled to the second pulley frame 1312.

For example, bearings 13303 may be coupled to both ends of the driving pulley 1330, and the bearings 13303 may be coupled to the driving pulley coupling unit 13126. Alternatively, the bearings 13303 may be coupled to both ends of the rotation axis of the driving pulley 1330, and similarly, the bearings 13303 may be coupled to the driving pulley coupling unit 13112.

From another perspective, the driving pulley 1330 may be disposed between the first pulley frame 1311 and the second pulley frame 1312, and the first pulley frame 1311 and the second pulley frame 1312 may be disposed spaced apart by the length of the driving pulley 1330.

However, the shape and structure of the pulley frame are not necessarily limited thereto, and the pulley frame 1310 may have various structures for disposing the driving pulley 1330 parallel to the shaft 3400.

Hereinafter, the driving pulley 1330 of the power transmission unit 1300 according to the first embodiment of the present disclosure will be described in detail.

Figure 33:
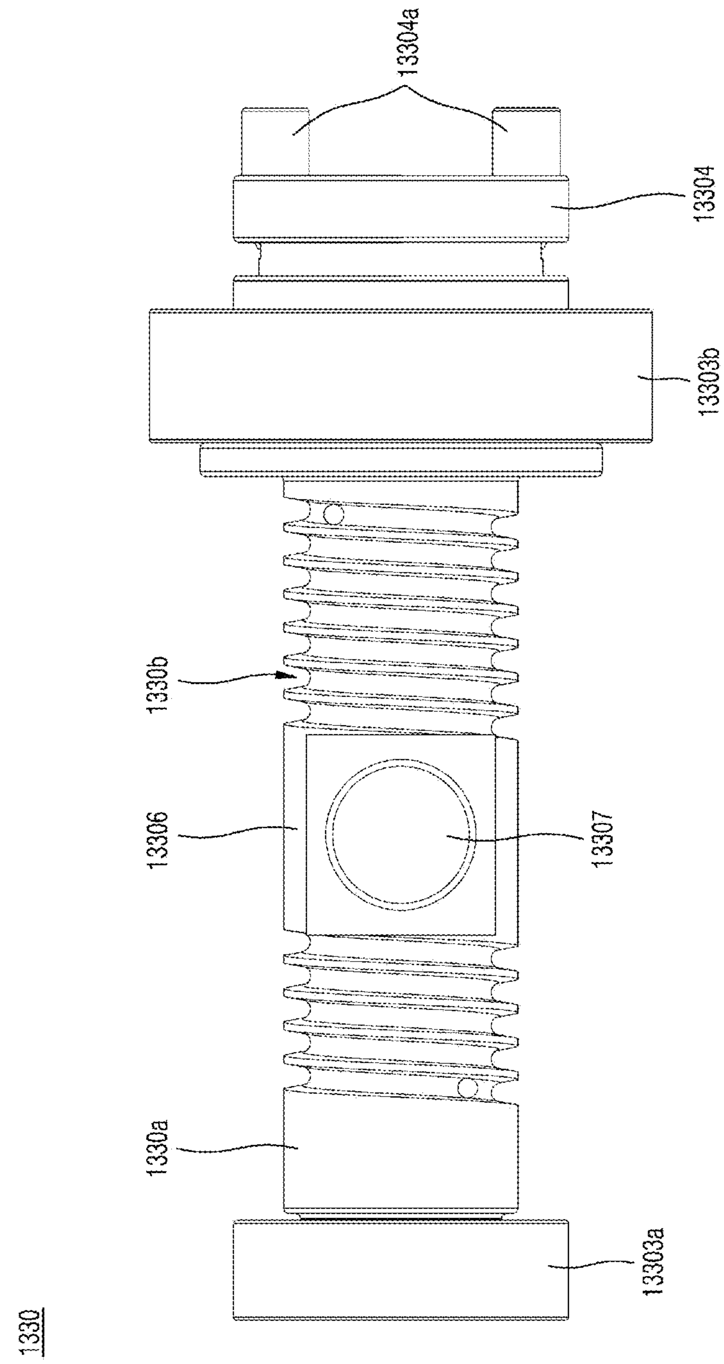
FIG. 33 is a side view of a driving pulley of the power transmission unit according to the first embodiment of the present disclosure.
Figure 34:
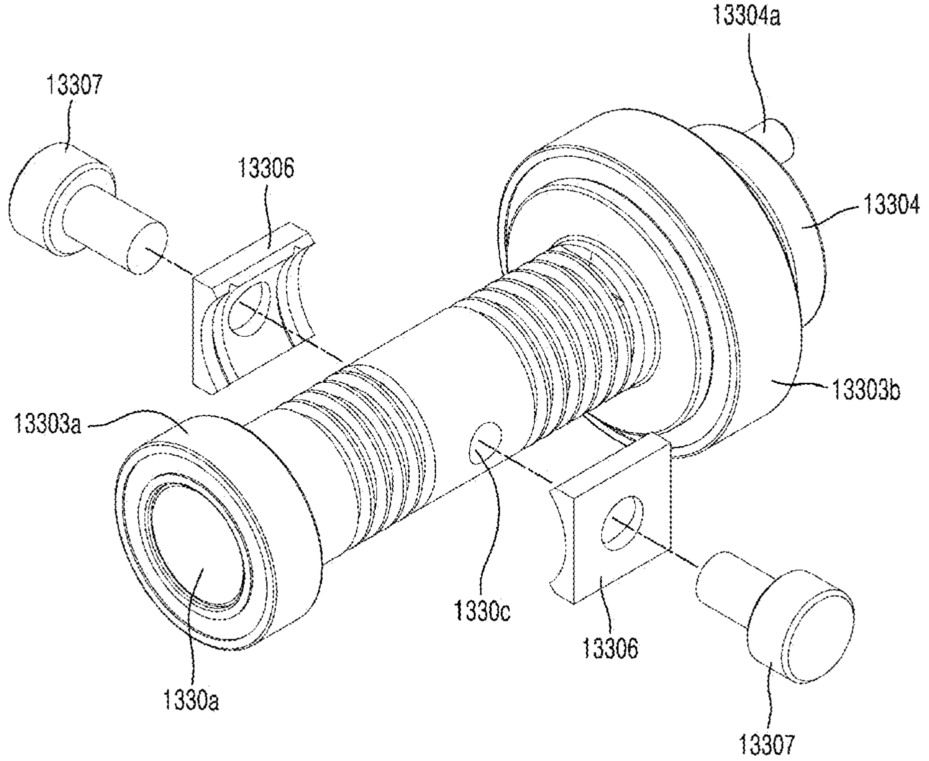
FIG. 34 is an exploded perspective view of the driving pulley of FIG. 33.
Figure 35A:
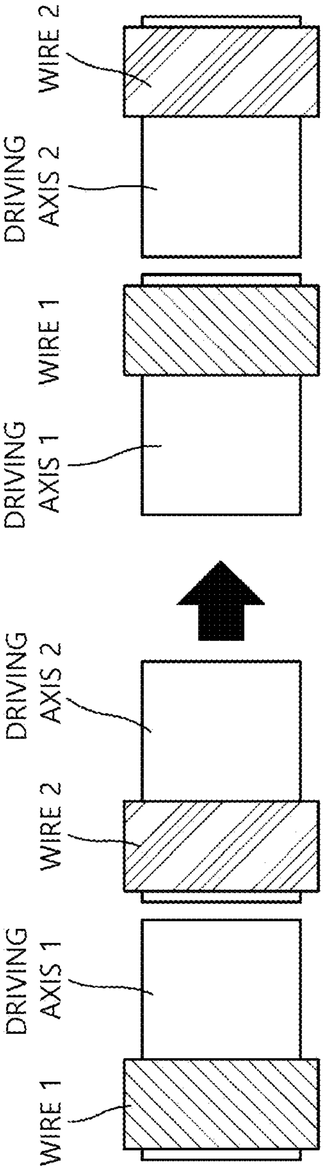
FIG. 35A to 35B is a diagram illustrating the relationship between the driving pulley and the wire according to a driving process of the power transmission unit according to the first embodiment of the present disclosure.
Figure 35B:
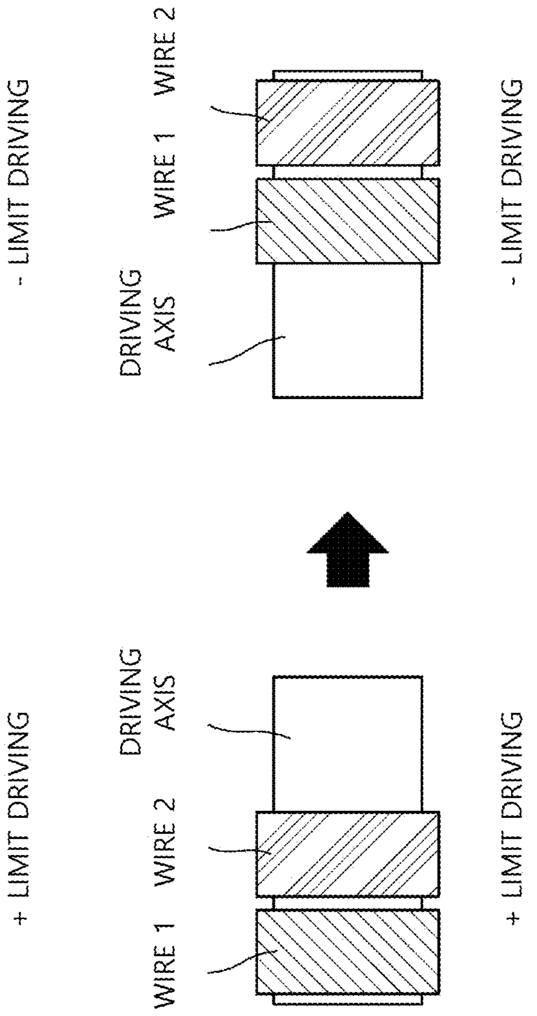
Figure 36:
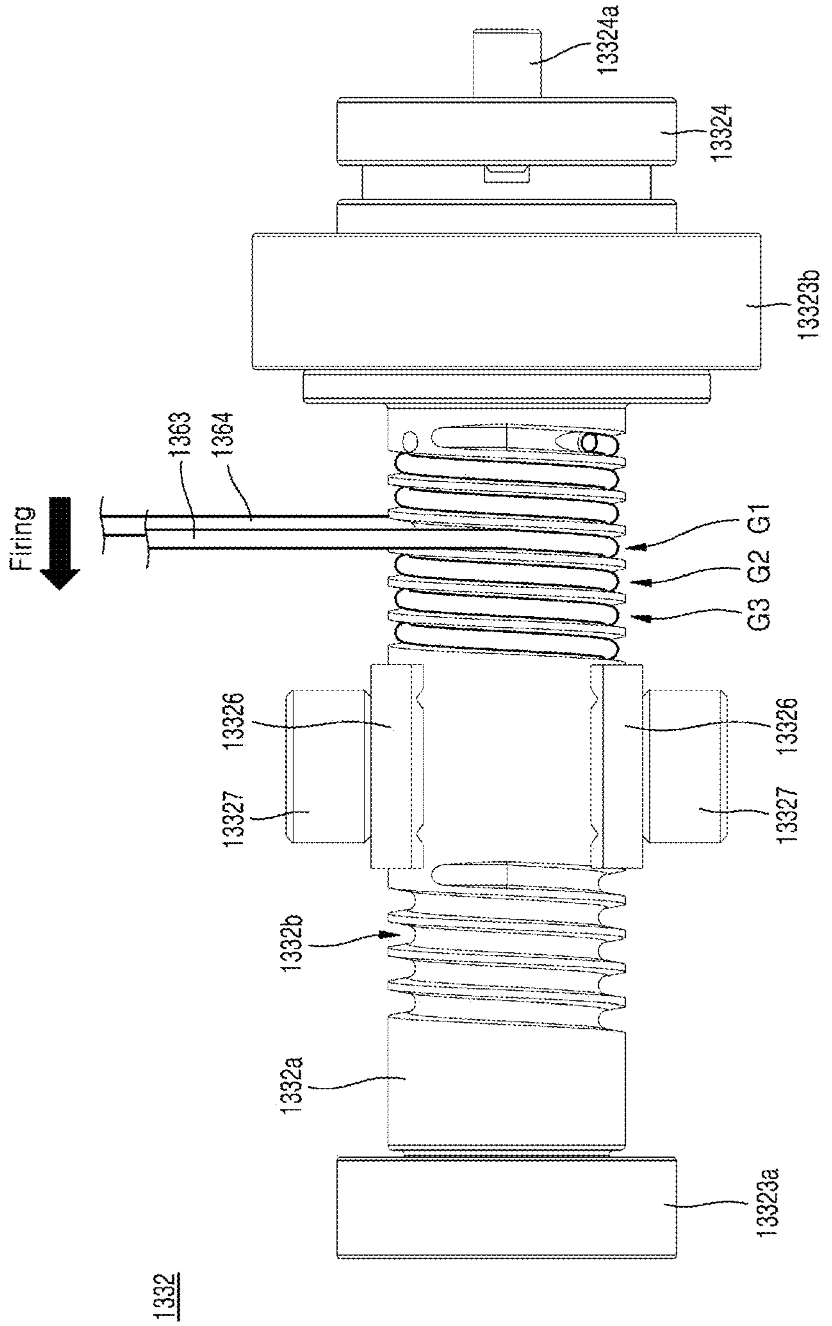
FIGS. 36 to 38 are diagrams illustrating a process of winding or unwinding a pair of wires around the driving pulley of FIG. 33.
Figure 37:
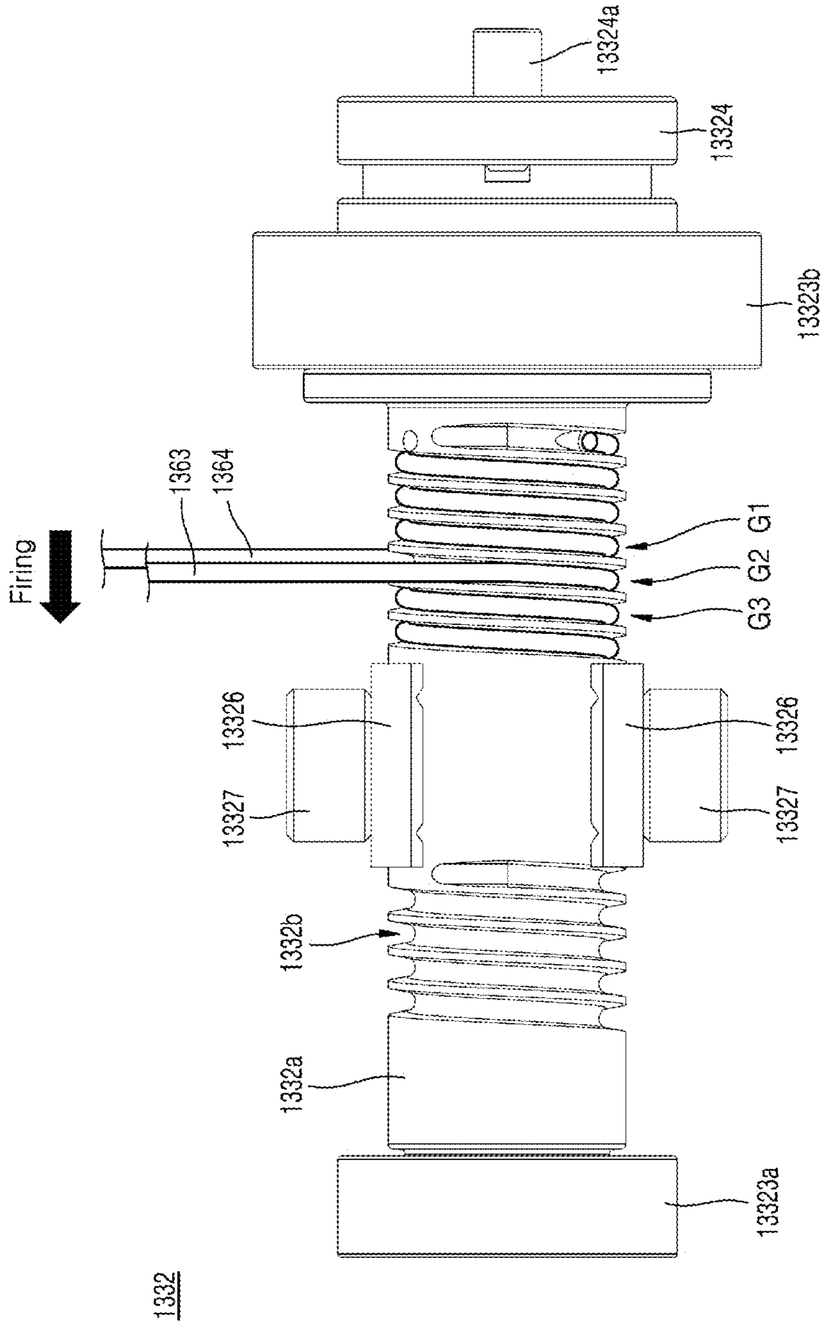
Figure 38:
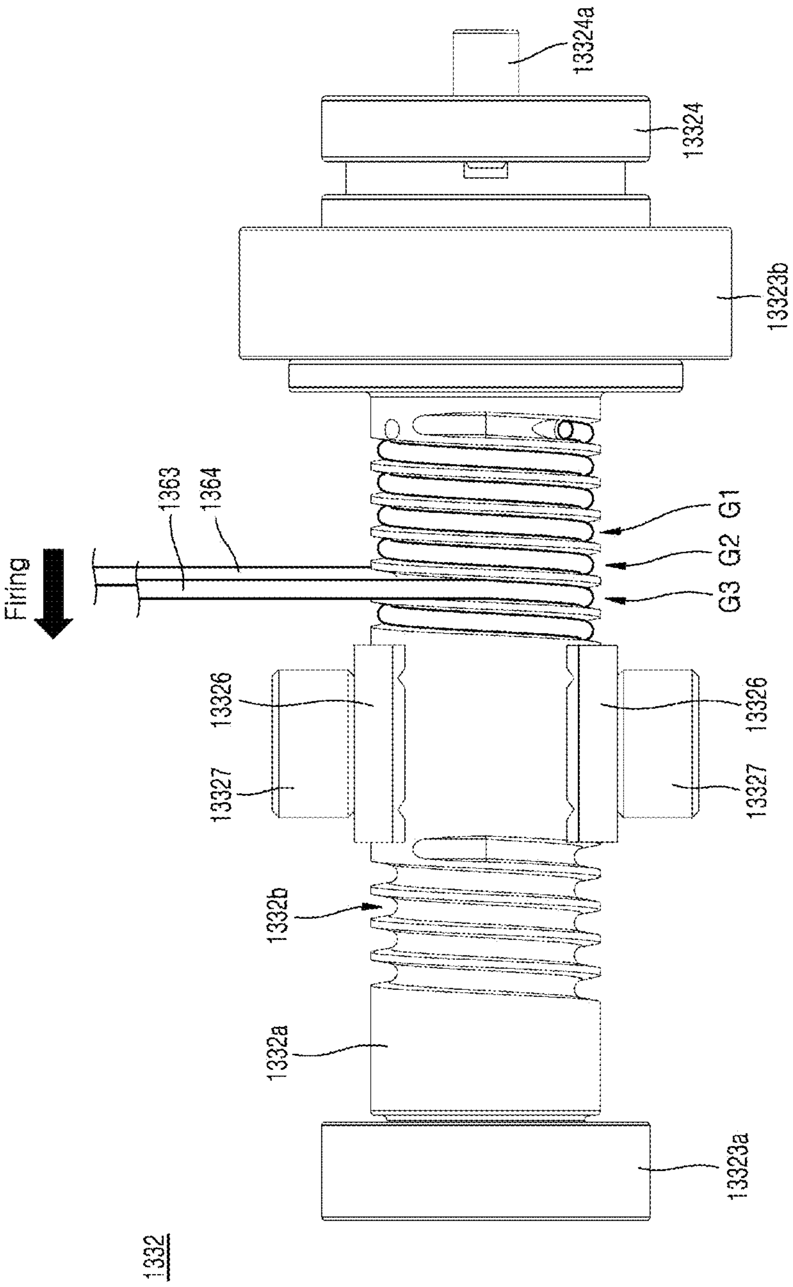

FIG. 33 is a side view of the driving pulley 1330 of the power transmission unit 1300 according to the first embodiment of the present disclosure. FIG. 34 is an exploded perspective view of the driving pulley 1330 of FIG. 33. FIG. 35A to 35B is a diagram illustrating the relationship between the driving pulley 1330 and the wire 1360 according to a driving process of the power transmission unit 1300 according to the first embodiment of the present disclosure. FIGS. 36 to 38 are diagrams illustrating a process of winding or unwinding a pair of wires 1360 around the driving pulley 1330 of FIG. 33.

Referring again to FIGS. 27 to 29, the driving pulley 1330 is accommodated in the pulley frame 1310 and may rotate around an axis by receiving power generated from the power generation unit. In addition, the rotation axis of the driving pulley 1330 may be disposed parallel to the shaft 3400. In the case where a plurality of driving pulleys 1330 are provided, the plurality of driving pulleys 1330 may be disposed parallel to each other.

Specifically, one end of the driving pulley 1330 may be coupled to the first pulley frame 1311, and the other end may be coupled to the second pulley frame 1312. Alternatively, in the case where the driving pulley 1330 is coupled to a separate rotation axis, one end of the rotation axis of the driving pulley 1330 may be coupled to the first pulley frame 1311, and the other end may be coupled to the second pulley frame 1312.

The driving pulley 1330 of the power transmission unit 1300 according to the first embodiment of the present disclosure may include a firing driving pulley 1331, 1332 on which the forward wire and the backward wire are wound, a yaw driving pulley 1333 on which the yaw wire is wound, and a pitch driving pulley 1334 on which the pitch wire is wound. As will be described later, the firing driving pulley 1331, 1332 may include a first firing driving pulley 1331 and a second firing driving pulley 1332.

The firing driving pulley 1331, 1332 is a driving pulley associated with the movement of the working member 1140 of the end tool 3100, and the forward wire and the backward wire are wires associated with the movement of the working member 1140 of the end tool 3100.

The yaw driving pulley 1333 is a driving pulley associated with the yaw rotation of the end tool 3100, and the yaw wire is a wire associated with the yaw rotation of the end tool 3100.

The pitch driving pulley 1334 is a driving pulley associated with the pitch rotation of the end tool 3100, and the pitch wire is a wire associated with the pitch rotation of the end tool 3100.

Each driving pulley will be described in detail later.

In addition, the wire 1360 is connected to the side surface of the driving pulley 1330, and the wire 1360 may be wound or unwound according to the rotation of the driving pulley 1330. In other words, one end of the wire 1360 is connected to the driving pulley 1330, and the other end is connected to the end tool 3100, so that power generated from the power generation unit may be transmitted to the end tool 3100. This will be described in detail later.

Referring to FIGS. 33 and 34, the driving pulley 1330 of the power transmission unit 1300 according to the first embodiment of the present disclosure may include a body 1330*a*, a wire fixing unit 13306, a pulley plate 13304, and the bearing 13303.

The body 1330*a* may be formed in a cylindrical shape and may form a center of rotation of the driving pulley 1330. In addition, the pulley plate 13304 may be coupled to one end of the body 1330*a*. Accordingly, the driving pulley 1330 may receive a rotational force applied to the pulley plate 13304 and rotate around the axis.

The body 1330*a* may form a groove 1330*b* on a side surface. Specifically, the driving pulley 1330 may form a screw-shaped groove 1330*b* on an outer circumstance, and the groove 1330*b* may be formed so that the wire 1360 is wound around the body 1330*a* of the driving pulley 1330.

The bearing 13303 may be disposed at one end or both ends of the driving pulley 1330. The bearing 13303 may support the driving pulley axis to facilitate the driving pulley 1330 to rotate about its axis within the pulley frame 1310.

Specifically, the bearing 13303*a* may be inserted into the driving pulley coupling unit 13112 formed in the first pulley frame 1311, and the bearing 13303*b* may be inserted into the driving pulley coupling unit 13126 formed in the second pulley frame 1312, so that the driving pulley 1330 may be formed to rotate along the axis within the pulley frame 1310.

There may be a method of using a fixing member or a bolt as a method of fixing the wire 1360 to the driving pulley 1330. Herein, the fixing member may have various shapes, such as a ball shape or a tube shape, as needed.

For example, the fixing member (not shown) may be coupled to one end of the wire 1360, and the fixing member may be placed over the driving pulley 1330 to fix one end of the wire 1360 to the driving pulley 1330.

Alternatively, one end of the wire 1360 may be fastened to the driving pulley 1330 with a bolt or the like. Specifically, one end of the wire 1360 may be wound half a turn or one turn under a bolt head, and the bolt may be fastened to the driving pulley 1330 to secure the wire 1360 to the driving pulley 1330.

In addition, the driving pulley 1330 according to an embodiment may have a washer disposed under the bolt to more stably press the wire 1360.

The pair of wires may be wound around the driving pulley 1330, and in this connection, one wire may be fastened using a bolt, and the other wire may be fastened with the fixing member.

For example, one end of one wire may be wound 1.5 turns around the driving pully 1330 and then the fixing member may be fastened to the driving pulley 1330, thereby fixing the wire to the driving pulley 1330. In addition, by rotating the driving pulley 1330 while the wire is wound to a certain extent, the wire may be wound further around the driving pulley 1330. Thus, the wire may be wound around the driving pulley 1330 while initial tension is applied.

In this state, the other wire may be wound around the driving pulley 1330 and fixed to the driving pulley 1330 via a bolt. Accordingly, the other wire may be pulled before being wound around the bolt so that initial tension may be applied, and the other wire may be fixed to the driving pulley 1330 via the bolt while initial tension is applied.

In addition, since the wire has initial tension, the wire may rotate the bolt in a specific direction. In this connection, the wire is wound in the opposite direction to the rotational direction in which the bolt is fastened, so that the bolt may be fastened more tightly as the wire is pulled.

When both wires are fixed to the driving pulley 1330 by the fixing member, it may be difficult to apply initial tension to the wire unless the fixing member is fixed at a precise location. However, as described above, by fixing one wire with the fixing member and fixing the other wire with a bolt, it may be easy to apply initial tension to the wire.

As such, the surgical instrument 3000 according to an embodiment of the present disclosure may easily control the process in the process of fixing different wires to the driving pulley 1330, thereby improving productivity.

The wire fixing unit 13306 may be formed to be coupled to the side surface of a driving pulley body 1330*a*. In addition, a fixing pin 13307 may be further included so that the wire fixing unit 13306 may be coupled to the driving pulley body 1330*a*.

Herein, the fixing pin 13307 may play the role of the bolt described above, and the wire fixing unit 13306 may additionally play the role of fixing the wire.

Specifically, the wire fixing unit 13306 may have a through hole formed into which the fixing pin 13307 is inserted. In addition, an insertion hole 1330*c* into which the fixing pin 13307 is inserted may be formed on the side surface of the driving pulley body 1330*a*. Accordingly, the fixing pin 13307 may be sequentially coupled to the through hole of the wire fixing unit 13306 and the insertion hole 1330*c* of the body 1330*a*, thereby coupling the wire fixing unit 13306 to the body 1330*a*.

The wire fixing unit 13306 may be coupled so as to be in close contact with the body 1330*a* by forming an inner surface coupled to the body 1330*a* in a shape corresponding to the shape of the body 1330*a*. Specifically, the inner surface of the wire fixing unit 13306 may be formed in a curved surface corresponding to the side surface of the body 1330*a*. For example, the cross section of the wire fixing member 13306 may form an arc corresponding to the circular shape formed by the cross section of the driving pulley body 1330*a*.

In addition, the wire fixing member 13306 may form one or more grooves on the inner surface that is coupled to the body 1330*a*. In addition, when the wire fixing member 13306 is closely coupled to the driving pulley body 1330*a*, a portion of the wire may be disposed in the groove.

Thus, one end of the wire wound around the driving pulley 1330 may be compressed between the wire fixing member 13306 and the driving pulley body 1330*a* and fixed to the driving pulley 1330.

Such wire fixing members 13306 may be provided as a pair and may be disposed opposite to each other on the side surface of the driving pulley body 1330*a*.

The pulley plate 13304 may be coupled to one end of the driving pulley body 1330*a*. The pulley plate 13304 may further include a protrusion unit 13304*a* that protrudes outward. This protrusion unit 13304*a* may be fastened to a motor plate provided on the driving motor of another device. Accordingly, the protrusion unit 13304*a* may stably fasten the pulley plate 13304 and the motor plate so that the rotational force of the driving motor is transmitted to the driving pulley 1330 through the pulley plate 13304.

However, the idea of the present disclosure is not limited thereto, and the groove may be formed on the pulley plate 13304 and the protrusion unit may be formed on the motor plate so as to be fastened to each other.

FIG. 35A to 35B is a diagram illustrating the relationship between the driving pulley and the wire according to a driving process of the power transmission unit according to the first embodiment of the present disclosure. FIGS. 36 to 38 are diagrams illustrating a process of winding or unwinding the pair of wires around the driving pulley of FIG. 33.

Referring to FIGS. 35A to 38, the wire may be wound around an outer circumference of the driving pulley or unwound from the outer circumference of the driving pulley according to the rotation of the driving pulley.

The wire unit may include the pair of wires, each of which is classified into a first wire and a second wire. The first wire may be wound around the driving pulley 1330 in a first direction, and the second wire may be wound around the driving pulley 1330 in a second direction opposite to the first direction. In addition, by the rotation of the driving pulley 1330 in either direction, one of the first wire and the second wire may be wound around the driving pulley 1330 and the other may be unwound from the driving pulley 1330.

For example, in the case where the first wire is wound clockwise around the driving pulley 1330 and the second wire is wound counterclockwise around the driving pulley 1330, when the driving pulley 1330 rotates clockwise, the first wire is wound further around the driving pulley 1330 and the second wire is unwound from the driving pulley 1330. Conversely, when the driving pulley 1330 rotates counterclockwise, the first wire is unwound from the driving pulley 1330 and the second wire is unwound further around the driving pulley 1330.

As such, the one-way rotation of the driving pulley 1330 may cause the first wire and the second wire to move in different directions. In other words, the one-way rotation of the driving pulley 1330 may cause one wire to be pulled and one wire to be unwound.

For example, the forward wire and the backward wire connected to the firing driving pulley 1331, 1332 are connected to the working member 1140 of the end tool 3100, and the forward wire and the backward wire connected to the same working member 1140 may move in opposite directions at a 1:1 ratio.

Specifically, when the forward wire is wound around the firing driving pulley 1331, 1332 as the firing driving pulley 1331, 1332 rotates in one direction, the working member 1140 of the end tool 3100 may move forward. Conversely, when the backward wire is wound around the firing driving pulley 1331, 1332 as the firing driving pulley 1331, 1332 rotates in the opposite direction, the working member 1140 of the end tool 3100 may move backward.

When the pair of wires are wound in different directions around the driving pulley 1330, the location where the wires are wound may move laterally towards the driving pulley 1330 as the wires are wound or unwound.

FIG. 35A shows a case where the pair of wires are wound around two driving pulleys respectively, and FIG. 35B shows a case where the pair of wires are each wound around one driving pulley.

Herein, FIG. 35A to 35B briefly illustrates only the wires at the location unwound from the driving pulley in the wires wound around the driving pulley.

Generally, in the process of winding wires around the driving pulley, the driving pulley is decoupled into at least two parts as shown in FIG. 35A. First, each wire is fixed to each part, and when the two parts rotate in opposite directions, the wires with a surplus length are wound around the driving pulley and initial tension is applied to the wires. Thereafter, the two parts are fixed relative to each other. However, in such a case, a gap is generated between the two parts, and when the wire is wound around the driving pulley, it may be difficult to pass from one part to the other across this gap. Alternatively, when the threads formed on the two parts are misaligned and the threads are not continuously connected while the two parts are coupled, it may be difficult to pass from one part to the other when the wire is wound around the driving pulley.

For example, as shown in FIG. 35A, wire 1 and wire 2 may be wound around driving axis 1 and driving axis 2, respectively. In this connection, wire 1 may be wound from the left end of driving axis 1, and wire 2 may be wound from the right end of driving axis 2.

A first drive (+Limit drive in FIG. 35A to 35B) may be a state in which wire 1 is wound around driving axis 1 to a minimum extent, and wire 2 is wound around driving axis 2 to a maximum extent. A second drive (−Limit drive in FIG. 35A to 35B) may be a state in which wire 1 is wound around driving axis 1 to the maximum extent and wire 2 is wound around driving axis 2 to the minimum extent.

In the process of driving from the first drive (+Limit drive) in which the wire is located to the left end of the driving axis in the drawing to the second drive (−Limit drive) in which the wire is located to the right end of the driving axis, the location where each wire is wound around the driving pulley moves laterally. In other words, wire 1 is wound around driving axis 1, and wire 2 is unwound from driving axis 2.

In this connection, wire 1 may have difficulty passing over the gap formed between driving axis 1 and driving axis 2 to driving axis 2.

As illustrated in FIG. 35B, two wires may be wound around one driving pulley. In other words, wire 1 may be wound from the left end of the driving axis, and wire 2 may be wound from the right end of the driving axis.

The first drive (+Limit drive) may be a state in which wire 1 is wound around the driving axis to the minimum extent, and wire 2 may be wound around the driving axis to the maximum extent without overlapping wire 1. The second drive (−Limit drive) may be a state in which wire 2 is wound around the driving axis to the minimum extent, and wire 1 may be wound around the driving axis to the maximum extent without overlapping wire 2.

In this connection, in the process of driving the driving pulley from the first drive (+Limit drive) to the second drive (−Limit drive), wire 1 is wound and wire 2 is unwound, so that the two wires move sideways together, and thus the two wires may move without overlapping each other. Accordingly, since two wires may be wound around one driving axis, the required space may be reduced.

Hereinafter, the second firing driving pulley 1332 will be described as an example.

FIG. 36 is a diagram illustrating a state in which the pair of wires is wound around the second firing driving pulley 1332. Herein, the pair of wires may be a second backward wire 1363 and a second forward wire 1364.

FIG. 37 is a diagram illustrating a state in which the second firing driving pulley 1332 of FIG. 36 rotates in one direction, so that the second backward wire 1363 is unwound from the second firing driving pulley 1332 and the second forward wire 1364 is further wound around the second firing driving pulley 1332.

FIG. 38 is a diagram illustrating a state in which the second firing driving pulley 1332 of FIG. 37 rotates in one direction, so that the second backward wire 1363 is further unwound from the second firing driving pulley 1332 and the second forward wire 1364 is further wound around the second firing driving pulley 1332.

In the process of proceeding from FIG. 36 to FIG. 38, the second firing driving pulley 1332 may have rotated one turn. In other words, each time the second firing driving pulley 1332 rotates one turn, the second backward wire 1363 may be unwound one turn from the second firing driving pulley 1332, and the second forward wire 1364 may be wound one turn around the second firing driving pulley 1332.

In other words, the driving pulley 1330 forms a continuous groove 1330*b* in which the first wire and the second wire are wound, and depending on the rotation of the driving pulley 1330, the other wire may be wound in the place where one wire is unwound.

Specifically, as illustrated in FIG. 36, the second backward wire 1363 and the second forward wire 1364 are wound around a first groove (G1). However, as the driving pulley rotates in one direction, the second backward wire 1363 and the second forward wire 1364 are wound around a second groove (G2), and as the driving pulley rotates further, the second backward wire 1363 and the second forward wire 1364 are wound around a third groove (G3).

In other words, the driving pulley 1330 according to the first embodiment of the present disclosure may have not only one wire wound around a groove 1330*b*, but also the first wire or the second wire wound therearound. From another perspective, the pair of wires connected to one driving pulley 1330 may share the groove 1330*b*.

Hereinafter, the disposition structure of the driving pulley 1330, the auxiliary pulley 1350, and the wire 1360 of the power transmission unit 1300 according to the first embodiment of the present disclosure will be described in detail.

Figure 40:
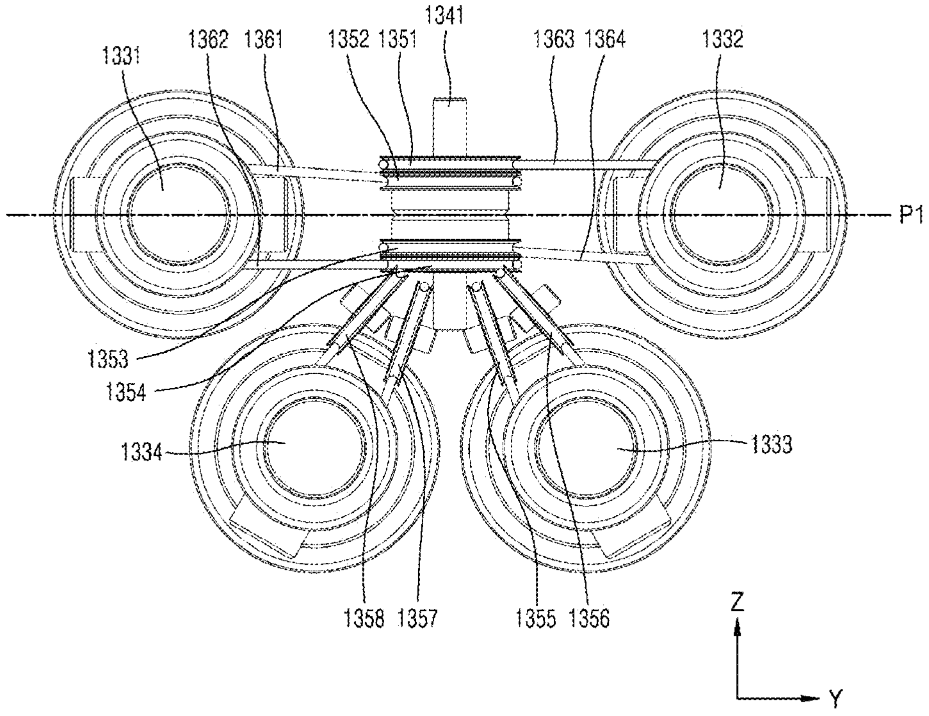
FIG. 40 is a view of the power transmission unit of FIG. 39 as viewed from the front in an X-axis direction.
Figure 41:
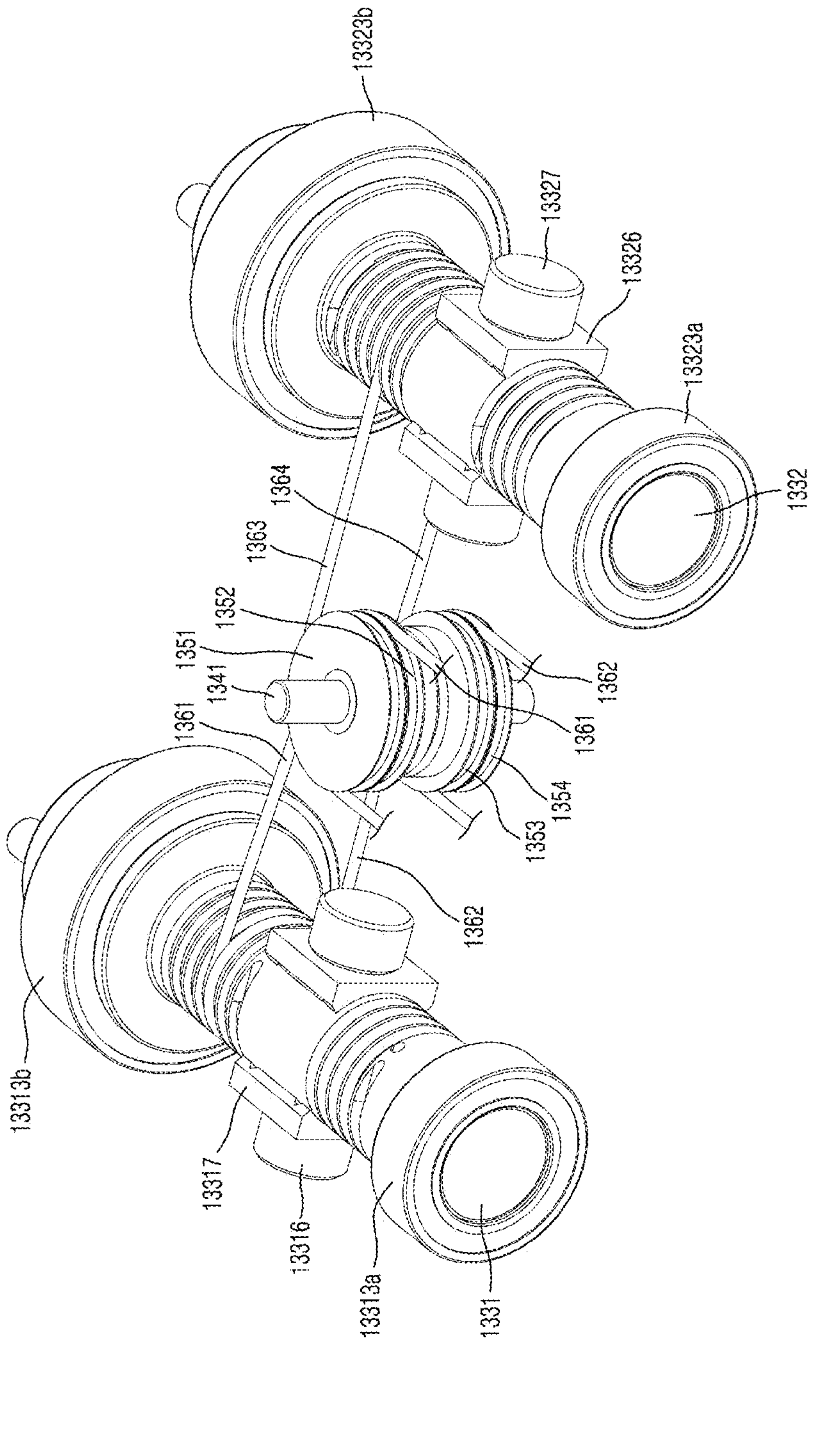
FIG. 41 is a perspective view of a wire connected to a driving pulley and a center auxiliary pulley in the power transmission unit of FIG. 39.
Figure 42:
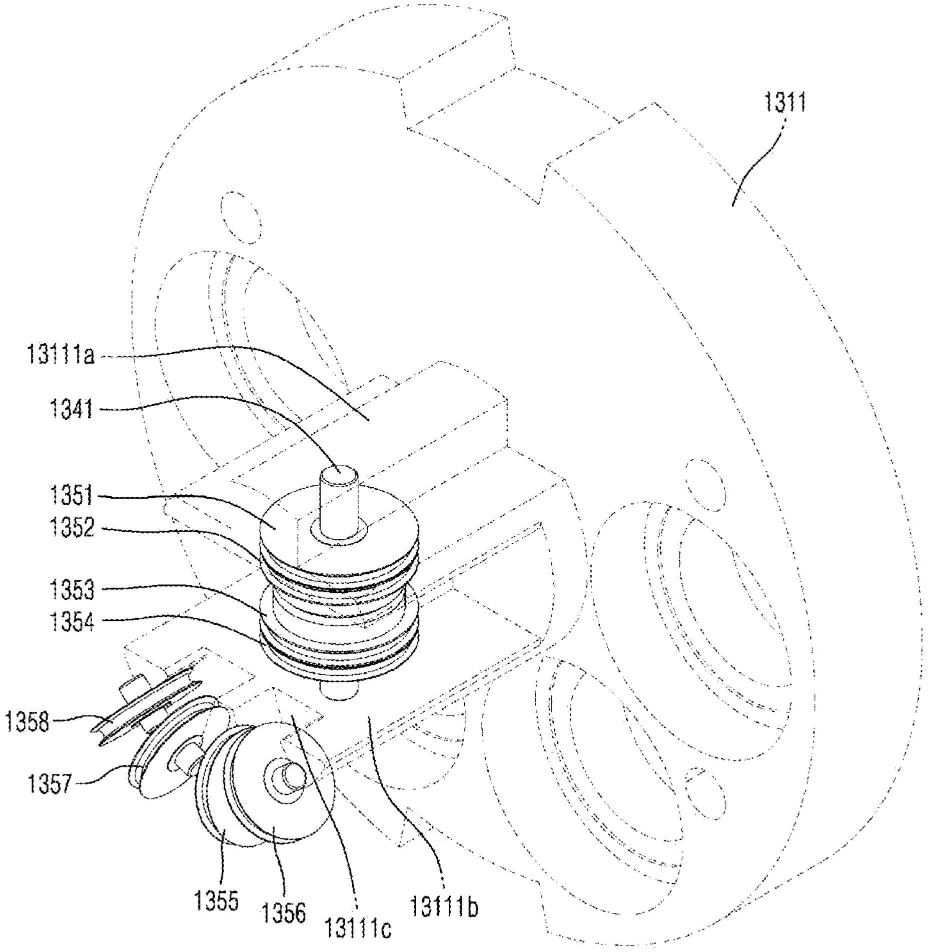
FIG. 42 is a view of an auxiliary pulley disposed on a first pulley frame in the power transmission unit of FIG. 28.
Figure 43:
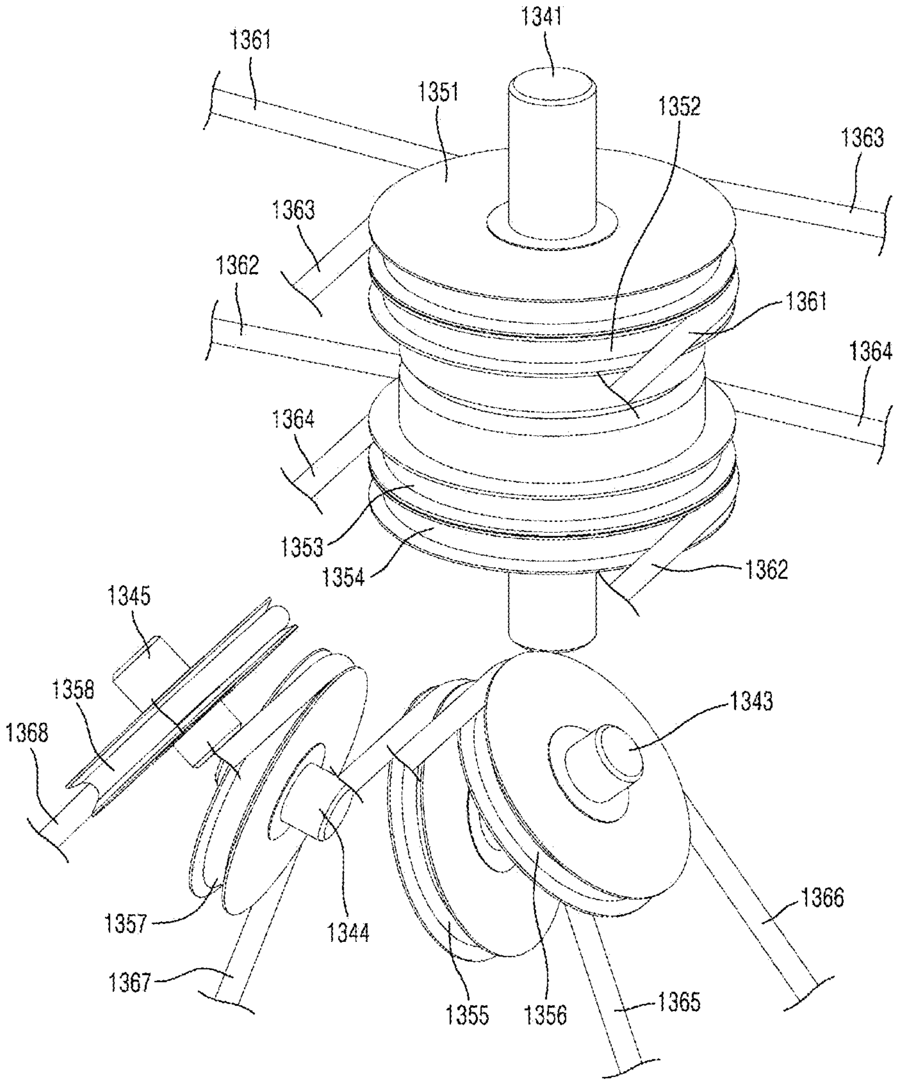
FIG. 43 is a perspective view of a state in which the wire is wound around the auxiliary pulley of FIG. 42.

FIG. 39 is a perspective view of the state where the first pulley frame of the power transmission unit of FIG. 28 is removed. FIG. 40 is a view of the power transmission unit of FIG. 39 as viewed from the front in an X-axis direction. FIG. 41 is a perspective view of a wire connected to a driving pulley and a center auxiliary pulley in the power transmission unit of FIG. 39. FIG. 42 is a view of an auxiliary pulley disposed on a first pulley frame in the power transmission unit of FIG. 28. FIG. 43 is a perspective view of a state in which the wire is wound around the auxiliary pulley of FIG. 42.

Referring to FIGS. 39 to 41, the driving pulley unit may include the firing driving pulley 1331, 1332, the yaw driving pulley 1333, and the pitch driving pulley 1334.

The firing driving pulley 1331, 1332 may be a driving pulley around which a forward wire and a backward wire are wound. The yaw driving pulley 1333 may be a driving pulley around which a yaw wire is wound. The pitch driving pulley 1334 may be a driving pulley around which a pitch wire is wound.

The driving pulley unit may include a pair of driving pulleys symmetrically disposed with respect to the central axis of the shaft 3400.

Herein, the pair of driving pulleys symmetrically disposed with respect to the central axis of the shaft 3400 may be the first firing driving pulley 1331 and the second firing driving pulley 1332.

In addition, the yaw driving pulley 1333 and the pitch driving pulley 1334 may be disposed parallel to the shaft 3400 and spaced apart from a pair of firing driving pulleys 1331, 1332. In the drawing, the yaw driving pulley 1333 and the pitch driving pulley 1334 are disposed below the firing driving pulley 1331, 1332, but the spirit of the present disclosure is not limited thereto, and the yaw driving pulley 1333 and the pitch driving pulley 1334 may be disposed within the pulley frame 1310 so as to be parallel to the firing driving pulley 1331, 1332.

Referring to FIGS. 39 to 43, the auxiliary pulley 1350 is disposed so that the wire 1360 partially contacts, so that the wire 1360 extending from the driving pulley 1330 may be diverted to guide the wire 1360 into the shaft 3400.

From another perspective, the wire 1360 wound around the driving pulley 1330 may be disposed inside the shaft 3400 through the auxiliary pulley 1330. In addition, each wire 1360 may be connected to the pulley of the end tool 3100 through the shaft 3400.

The auxiliary pulley unit includes at least one pair of auxiliary pulleys, and the pair of auxiliary pulleys may be disposed spaced apart from each other in correspondence with the diameter of the driving pulley 1330 around which the pair of wires are wound.

The pair of wires are wound around one driving pulley 1330 and disposed to extend from the driving pulley 1330, and each wire may be disposed to be parallel or nearly parallel to each other. In this connection, each wire extending from the driving pulley 1330 may be disposed to pass through each auxiliary pulley 1350 that is spaced apart from each other so that each wire is sufficiently spaced apart.

The auxiliary pulley unit may include a center auxiliary pulley disposed to be adjacent to the central axis of the shaft 3400.

In other words, the center auxiliary pulley may be disposed to be adjacent to the extension line of the shaft 3400. From another perspective, the center auxiliary pulley may be disposed between the pair of firing driving pulleys 1331, 1332.

In addition, the center auxiliary pulley may be disposed within the center auxiliary pulley fixing unit 13111 of the first pulley frame 1311.

Herein, the center auxiliary pulley is axially coupled to the center auxiliary pulley rotation axis 1341, and the center auxiliary pulley rotation axis 1341 may be coupled to the center auxiliary pulley fixing unit 13111.

The center auxiliary pulley rotation axis 1341 to which the center auxiliary pulley is axially coupled may be perpendicular to the central axis of the shaft 3400. In addition, the center auxiliary pulley rotation axis 1341 may be perpendicular to a virtual plane (P1) that includes the rotation axes of the pair of driving pulleys symmetrically disposed based on the central axis of the shaft 3400.

In other words, since the center auxiliary pulley rotates based on the center auxiliary pulley rotation axis 1341, the rotation plane on which the center auxiliary pulley rotates may be parallel to the virtual plane (P1).

Accordingly, the wire extended from the firing driving pulley 1331, 1332 may change direction by nearly 90° by passing through the center auxiliary pulley and enter the inside of the shaft 3400.

The auxiliary pulley of the power transmission unit 1300 according to the first embodiment of the present disclosure is disposed as described above so that the wire extending from the inside of the shaft 3400 to the power transmission unit 1300 may be stably wound around the driving pulley 1330 disposed parallel to the shaft 3400.

The center auxiliary pulley may include a first auxiliary pulley 1351, a second auxiliary pulley 1352, a third auxiliary pulley 1353, and a fourth auxiliary pulley 1354 that are axially coupled around the same rotation axis.

Herein, the first auxiliary pulley 1351 and the second auxiliary pulley 1352 may be disposed on one side based on the central axis of the shaft 3400, and the third auxiliary pulley 1353 and the fourth auxiliary pulley 1354 may be disposed on the other side based on the central axis of the shaft 3400.

From another perspective, the first auxiliary pulley 1351 and the second auxiliary pulley 1352 may be disposed on one side of the virtual plane (P1) including each rotation axis of the pair of driving pulleys, and the third auxiliary pulley 1353 and the fourth auxiliary pulley 1354 may be disposed on the other side.

From another perspective, the first auxiliary pulley 1351 and the second auxiliary pulley 1352 may be disposed close to each other, and the third auxiliary pulley 1353 and the fourth auxiliary pulley 1354 may be disposed close to each other. In addition, the first auxiliary pulley 1351 and the second auxiliary pulley 1352 may be disposed spaced apart from the third auxiliary pulley 1353 and the fourth auxiliary pulley 1354.

As described above, the power transmission unit 1300 according to an embodiment of the present disclosure has the pair of wires wound around one driving pulley 1330, for example, the forward wire and the backward wire may be wound in different directions around one firing driving pulley 1331, 1332.

Herein, one of the forward wire and the backward wire may pass through the auxiliary pulley disposed at an upper end, and the other may pass through the auxiliary pulley disposed at a lower end.

Specifically, the driving pulley unit includes a first driving pulley and a second driving pulley disposed symmetrically with respect to the central axis of the shaft 3400. A first forward wire 1361 and a first backward wire 1362 may be wound around the first driving pulley, and the second forward wire 1364 and the second backward wire 1363 may be wound around the second driving pulley.

For example, the first driving pulley may be the first firing driving pulley 1331 and the second driving pulley may be the second firing driving pulley 1332.

In addition, the first forward wire 1361 may be wound around the second auxiliary pulley 1352, the first backward wire 1362 may be wound around the fourth auxiliary pulley 1354, the second forward wire 1364 may be wound around the third auxiliary pulley 1353, and the second backward wire 1363 may be wound around the first auxiliary pulley 1351.

In an embodiment, the first forward wire 1361 may be wound around the first auxiliary pulley 1351, the first backward wire 1362 may be wound around the third auxiliary pulley 1353, the second forward wire 1364 may be wound around the fourth auxiliary pulley 1354, and the second backward wire 1363 may be wound around the second auxiliary pulley 1352.

In the case where both pairs of wires wound around one driving pulley are disposed only at an upper end or a lower end relative to the central axis of the shaft 3400, when the wire passes the auxiliary pulley and is wound around the driving pulley, one of the wires may be sharply bent.

In other words, upon examining the progressing route along which the wire enters the auxiliary pulley from the shaft 3400 and exits from the auxiliary pulley to the driving pulley, even when the wire enters parallel to the rotational plane of the auxiliary pulley, the wire may be bent at a large angle relative to the rotational plane of the auxiliary pulley when exiting from the auxiliary pulley. Accordingly, the wire may apply a force to the auxiliary pulley, which may cause a large friction between the wire and the auxiliary pulley.

However, as described above, the power transmission unit 1300 according to an embodiment of the present disclosure may reduce the force that the auxiliary pulley 1350 receives from the wire 1360 by disposing the auxiliary pulley 1350, and may reduce the friction that occurs between the wire 1360 and the auxiliary pulley 1350.

In addition, the power transmission unit 1300 according to an embodiment of the present disclosure may partially offset the force applied to the center auxiliary pulley rotation axis 1341 by axially coupling the first auxiliary pulley 1351, the second auxiliary pulley 1352, the third auxiliary pulley 1353, and the fourth auxiliary pulley 1354 to one rotation axis.

Specifically, since the first forward wire 1361 and the second forward wire 1364 change directions in opposite directions along a Y-axis and move, and the first backward wire 1362 and the second backward wire 1363 change directions in opposite directions along the Y-axis and move, a Y-axis component force among the forces applied to the rotation axis may be offset from each other.

Referring again to FIGS. 39 to 43, a pair of yaw wires 1365, 1366 that are wound around the yaw driving pulley 1333 and extended from the yaw driving pulley 1333 may extend toward the shaft 3400 through the yaw auxiliary pulley 1355, 1356, respectively. In addition, a pair of pitch wires 1367, 1368 wound around the pitch driving pulley 1334 and extended from the pitch driving pulley 1334 may extend toward the shaft 3400 through the pitch auxiliary pulley 1357, 1358, respectively.

The yaw auxiliary pulley 1355, 1356 and the pitch auxiliary pulley 1357, 1358 may be coupled to different axes, respectively.

Specifically, the yaw auxiliary pulley 1355, 1356 is provided as a pair, and the pair of yaw auxiliary pulleys 1355, 1356 may be disposed to be spaced apart from each other, but the yaw auxiliary pulleys 1355, 1356 may be disposed so as not to be parallel to each other.

In other words, the pair of yaw auxiliary pulleys 1355, 1356 may be disposed to become closer to each other in a direction away from the yaw driving pulley 1333.

Likewise, the pitch auxiliary pulley 1357, 1358 is provided as a pair, and the pair of pitch auxiliary pulleys 1357, 1358 may be disposed to be spaced apart from each other, but the pitch auxiliary pulleys 1357, 1358 may be disposed so as not to be parallel to each other.

In other words, the pair of pitch auxiliary pulleys 1357, 1358 may be disposed to become closer to each other in a direction away from the pitch driving pulley 1334.

The pitch auxiliary pulley 1355, 1356 and the pitch auxiliary pulley 1357, 1358 may be partially accommodated in the auxiliary pulley accommodation groove 13111*c* formed in the lower end unit 13111*b* of the center auxiliary pulley fixing unit 13111.

In addition, as described above, the auxiliary pulley 1355, 1356 and the pitch auxiliary pulley 1357, 1358 may be partially accommodated in the auxiliary pulley accommodation groove 13123*a* formed in the second pulley frame 1312. In addition, the auxiliary pulley rotation axis 1342, 1343, 1344, 1345 may be fixed to the rotation axis fixing groove 13123*b*.

Reverse Drive

A surgical instrument including a stapler may operate based on power from an actuator. However, a conventional surgical instrument including the stapler may experience situations where the power of the actuator is not transmitted to the end tool due to various reasons. For example, the surgical instrument may be driven based on power from a motor. However, when an emergency situation occurs, such as a power cutoff to a motor or a motor failure, the articulations or working members of the surgical instrument, such as a blade of the stapler, may not be manipulated. Accordingly, when the power supply to the actuator is interrupted during a laparoscopic surgery using a conventional hand-held surgical instrument, it may inevitably be necessary to switch from a laparoscopic surgery to a laparotomic surgery and remove the surgical instrument from the body of a patient.

To give a non-limiting but more specific example, the surgical instrument driven by a motor may not be driven during surgery, and it may be impossible due to a battery discharge or a motor failure. In this connection, when the conventional handheld surgical instrument is used, for example, since the surgical instrument whose articulation in the yaw direction and/or the articulation in the pitch direction is manipulated may not be returned to its original location, there was an issue that the instrument might not be removed through a trocar, so that the laparoscopic surgery had to be switched to an laparotomic surgery. In addition, various issues might occur, such as the inability to take out the body tissue that the surgical instrument was biting.

As an attempt to address this issue, it may be possible to consider activating driving elements, such as articulations in a surgical instrument manipulated by a hand of a person, replacing the function of a motor. However, this is not only very unintuitive to a user, but also causes great inconvenience. As an example, when a situation occurs during surgery using the surgical instrument in which the motor may not be operated, a method may be attempted in which the motor is decoupled, a wrench is inserted into the driving axis of the surgical instrument, and the user directly activates the driving elements, such as the articulations, to return the driving elements to the state before the manipulation, and then the surgical instrument is removed from the body of a patient. This method is very non-intuitive and physically inconvenient, as it requires the user to be aware of the rotation direction of the driving axis and the activation direction of the driving element.

According to an embodiment of the present disclosure, by applying an external force to the end tool of the surgical instrument itself to move the driving element, such as an articulation, in the desired direction, the driving element may be returned to the state before manipulation in the most intuitive and convenient way. In other words, the surgical instrument according to an embodiment of the present disclosure may be configured to enable reverse drive, in which the driving element, such as an articulation, is directly manipulated by applying an external force to the driving element, rather than controlling the same by the actuator, such as a motor, so that the power is transmitted in the opposite direction.

In particular, the surgical instrument such as the stapler exemplified by the present disclosure have been configured so that reverse drive is not possible in the past. This is because the conventional stapler uses a motor to rotate a screw, and a manipulation member of the end tool moves by the rotation of the screw. Power transmission structures such as screws and worm gears are designed so that forward drive, in which the screw is activated by a power unit and the manipulation member is driven accordingly, is possible but reverse drive, in which the screw is activated by operating the manipulation member, is not possible.

Figure 44:
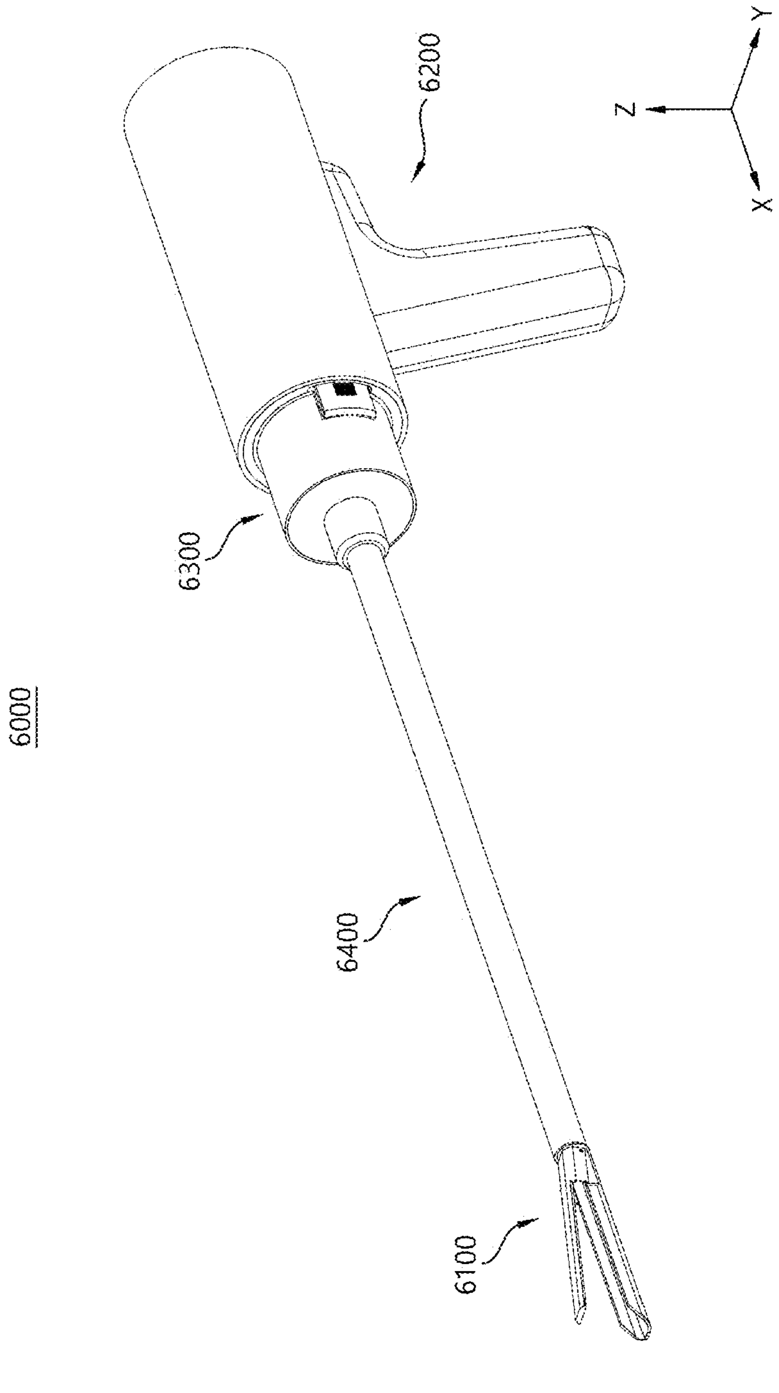
FIG. 44 is a schematic perspective view of a hand-held surgical instrument according to an embodiment of the present disclosure.
Figure 45:
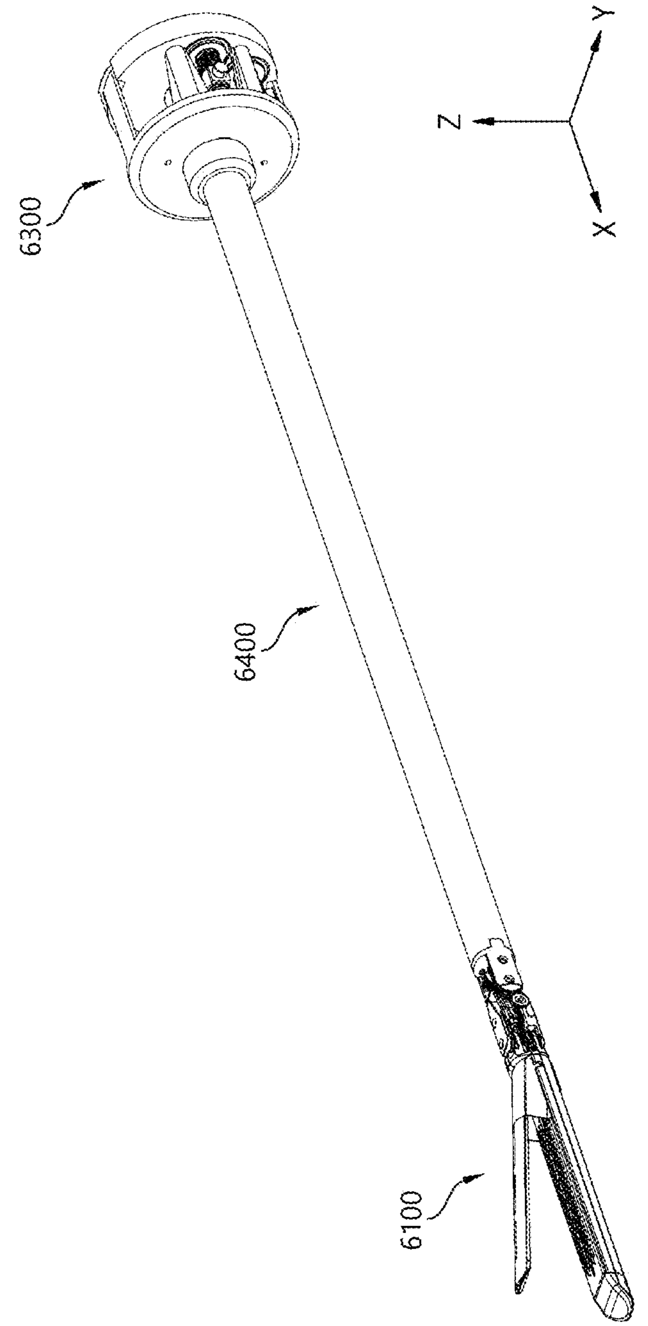
FIG. 45 illustrates a state in which the manipulation unit of the surgical instrument of FIG. 44 is decoupled.

FIG. 44 is a schematic perspective view of a hand-held surgical instrument according to an embodiment of the present disclosure. FIG. 45 illustrates a state in which the manipulation unit of the surgical instrument of FIG. 44 is decoupled. As illustrated in FIGS. 44 and 45, the surgical instrument according to an embodiment of the present disclosure may be a hand-held stapler. However, it should be noted that the technical idea of the present disclosure is not limited thereto.

The surgical instrument according to an embodiment of the present disclosure, as illustrated in FIGS. 44 to 45, may be configured to enable reverse drive in which a conversion element of the power transmission unit is activated by activating at least one driving element provided in the end tool by an external force. Accordingly, even in a state where the power transmission of the actuator and the conversion element is decoupled, the driving element may be controlled as intended. Even in a state where the power transmission of the actuator becomes impossible during surgery, the surgical instrument may be easily removed from the inside of the body by directly controlling the driving element by an external force.

Non-limitingly, but more specifically, for example, even in an emergency situation where the power transmission of the actuator is interrupted in a situation where the end tool is manipulated inside the body during laparoscopic surgery, it is possible to enable at least one driving element of the end tool to be controlled by an external force. Accordingly, for example, in the process of moving the end tool out of the body, the articulation of the end tool may be rotated by the trocar for guiding the pupil of the body or the surgical instrument, so that the end tool may be safely taken out of the body. Alternatively, for example, by moving the working member of the stapler on which the blade is mounted by an external force, it is possible to decouple the body tissue that was bitten by the pair of jaws from the end tool.

As illustrated in FIGS. 44 and 45, a surgical instrument 6000 capable of reverse drive according to an embodiment of the present disclosure may include an end tool 6100, a shaft 6400, and a power transmission unit 6300. According to an aspect, the surgical instrument according to an embodiment of the present disclosure may be a hand-held device. In other words, the surgical instrument according to an aspect may further include a manipulation unit 6200 coupled to the power transmission unit 6300, as illustrated in FIG. 44, for example. For example, the manipulation unit 6200 may have the actuator and the handle unit, as described above in the present disclosure with reference to FIG. 1. In addition, the manipulation unit 6200 may be provided with an interface that may be directly controlled by a medical doctor, for example, a tong shape, a stick shape, a lever shape, or the like. When the medical doctor controls the manipulation unit 6200, the end tool 6100 connected to the corresponding interface and inserted into the body of a surgical patient performs certain activation, thereby performing surgery. Herein, although the manipulation unit 3200, 6200 is illustrated in FIG. 1 or 4 as being formed in the shape of a handle that allows fingers to make close contact and perform one or more operations, such as pulling or pushing, the idea of the present disclosure is not limited thereto, and various types of manipulation units that are connected to the end tool 3100, 6100 and manipulate the end tool 3100, 6100 are possible. For example, the manipulation unit of the surgical instrument according to an embodiment of the present disclosure may be a manual type manipulation unit 5200 as described above with reference to FIGS. 24 to 26. However, it should be noted that the technical idea according to the present disclosure is not limited thereto.

Referring again to FIGS. 44 to 45, another end tool 6100 on one side of the present disclosure may be provided with at least one driving element that is activated by a wire. For example, the driving element may include, but is not limited to, an articulation element or the working member. In addition, the driving element may include one that is manipulated by the wire or link structure.

The power transmission unit 6300 may be configured to control the linear movement of the wire for activating the driving element based on the rotational movement of the conversion element according to the power from the actuator. According to an aspect, the power transmission unit 6300 connects the manipulation unit 6200 and the end tool 6100 to transmit the driving force of the manipulation unit 6200 to the end tool 6100, and may include a plurality of wires, pulleys, links, joints, and gears. Herein, the power transmission unit 6300 may borrow the structure of the power transmission unit 1300 described above with reference to FIGS. 27 to 43 of an embodiment of the present disclosure, but is not limited thereto. In addition, the conversion element provided in the power transmission unit 6300 may be the driving pulley 1330 of the power transmission unit 1300 described above with reference to FIGS. 27 to 43, but is not limited thereto.

The shaft 6400 may be disposed between the end tool 6100 and the power transmission unit 6300, connect the end tool 6100 and the power transmission unit 6300, and provide a passage for the movement of the wire.

The surgical instrument according to an embodiment of the present disclosure is configured to enable reverse drive by controlling the linear movement of the wire based on the rotational movement of the conversion element as described above, and controlling the driving element to activate accordingly. In other words, according to an embodiment of the present disclosure, the surgical instrument is configured to be capable of forward drive in which the driving element is activated according to the activation of the actuator, as well as reverse drive in which the conversion element is activated according to the activation of the driving element according to an external force.

As described above, according to an aspect of the present disclosure, the driving element provided in the end tool 6100 may include at least one articulation or at least one of the pair of jaws that rotate within a predetermined angular range according to the linear movement of the wire.

The articulation element may include a rotation axis configured to enable the end tool according to an embodiment of the present disclosure to rotate in at least one direction. For example, the end tool 6100 of the surgical instrument 6000 according to an embodiment of the present disclosure may be configured to rotate in at least one direction, and may be configured to perform, for example, a pitch motion around the Y-axis, and a yaw motion and an actuation motion around the Z-axis. Such a rotational motion may be performed, for example, by providing a pitch axis articulation or a yaw axis articulation as the driving element.

Herein, each of the pitch, yaw, and actuation motions used in FIGS. 44 to 45 are defined as follows.

First, the pitch motion means a motion in which the end tool 6100 rotates up and down with respect to the extension direction (X-axis direction of FIG. 44) of the shaft 6400, in other words, a motion in which the end tool 6100 rotates centered on the Y-axis of FIG. 44. In other words, the pitch motion means a motion in which the end tool 6100 formed by extending from the shaft 6400 in the extension direction of the shaft 6400 (X-axis direction of FIG. 44) rotates up and down around the Y-axis with respect to the shaft 6400.

Next, the yaw motion means a motion in which the end tool 6100 rotates left and right with respect to the extension direction (X-axis direction) of the shaft 6400, in other words, a motion in which the end tool 6100 rotates around the Z-axis. In other words, the yaw motion means a motion in which the end tool 6100 formed by extending from the shaft 6400 in the extension direction (X-axis direction) of the shaft 6400 rotates left and right around the Z-axis with respect to the shaft 6400. In other words, the yaw motion means a motion in which two jaws formed on the end tool 3100 rotate in the same direction around the Z-axis.

The actuation motion means a motion in which the end tool 6100 rotates around the same rotation axis as the yaw motion, but the two jaws rotate in opposite directions while the jaws close or open. In other words, the actuation motion means a motion in which the two jaws formed on the end tool 3100 rotate in opposite directions around the Z axis.

According to an aspect, the driving element provided in the end tool 6100 may be the working member. For example, the surgical instrument according to an embodiment of the present disclosure may be a stapler or a vessel sealer. Herein, the working member may be a component that performs an operation by moving forward toward the distal unit of the end tool or moving backward away from the distal unit in the surgical instrument such as the stapler or the vessel sealer. The working member may be, but is not limited to, the working member 3140 as described above with reference to FIGS. 2 to 23 of an embodiment of the present disclosure. As a non-limiting example, the working member may be provided with a blade area for cutting the body tissue of a patient. The working member or an inclined unit for withdrawing a staple of the staple cartridge in conjunction with the working member may be provided. In addition, the working member may be provided with a clamp that applies pressure toward each other to the pair of jaws provided in the surgical instrument. The working member according to an aspect of the present disclosure including various embodiments may be understood as the driving element that performs a linear motion toward or away from the distal unit of the end tool due to the linear motion of the wire, but is not limited thereto.

Figure 46:
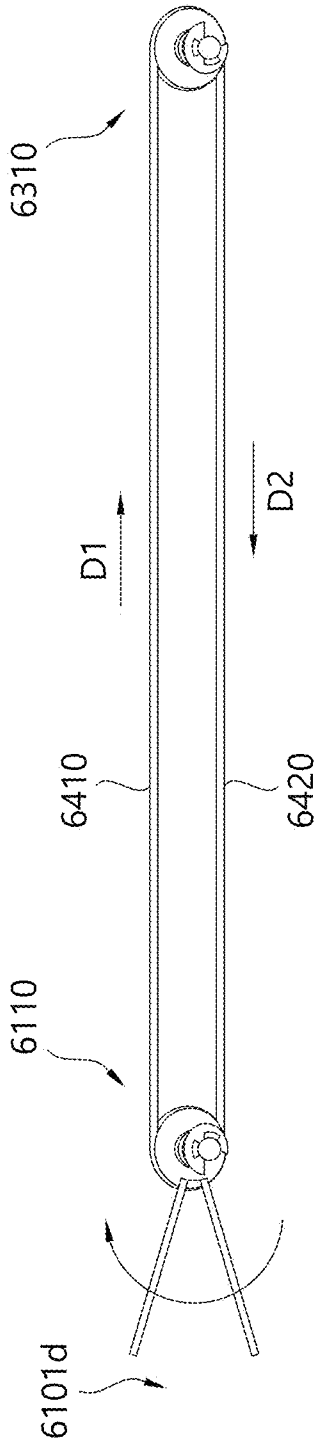
FIG. 46 is an exemplary view of a closed loop by a driving element and a wire of the surgical instrument according to an embodiment of the present disclosure.

FIG. 46 is an exemplary view of a closed loop by a driving element and a wire of the surgical instrument according to an embodiment of the present disclosure. As illustrated in FIG. 46, according to an aspect of the present disclosure, a straight line movement of the wires 6410, 6420 is controlled based on the rotational movement of the conversion element 6310, and a driving element 6110 may be activated accordingly.

Herein, the wires may include a first wire 6410 that moves backward in a direction (D1) away from a distal unit 6101*d* of the end tool to activate the driving element 6110 in a first direction, and a second wire 6420 that moves forward toward the distal unit 6101*d* of the end tool to activate the driving element 6110 in the first direction. As a non-limiting example, when the driving element 6110 is a driving element that performs a rotational movement such as the articulation as illustrated in FIG. 46, the switching element 6310 may be rotated clockwise to rotate the driving element 6110 clockwise on the ground. Accordingly, the first wire 6410 may move backward in the direction (D1) away from the distal unit 6101*d* of the end tool, and the second wire 6420 may move forward toward the distal unit 6101*d* of the end tool. Accordingly, the driving element 6110 may rotate clockwise on the ground, which may be understood as a rotational movement of the articulation.

Conversely, the conversion element 6310 may be rotated counterclockwise to rotate the driving element 6110 counterclockwise on the ground. Accordingly, the second wire 6420 may move backward in the direction (D1) away from the distal unit 6101*d* of the end tool, and the first wire 6410 may move forward toward the distal unit 6101*d* of the end tool. Accordingly, the driving element 6110 may rotate counterclockwise on the ground, which can be understood as a rotational movement of the articulation.

In FIGS. 46 to 51, the rotation axis is illustrated in one direction perpendicular to the ground to explain the operational relationship of the driving element, the wire, and the conversion element, but it is obvious that the technical idea of the present disclosure is not limited thereto. For example, as described above with reference to FIGS. 1 to 23, the end tool may be provided with a plurality of additional pulleys in addition to an articulation rotation axis, so that the rotation axis of the driving element may be configured to rotate in various directions. In addition, as described above with reference to FIGS. 27 to 43, the power transmission unit may be provided with the plurality of additional pulleys in addition to the driving pulley, so that the rotation axis of the conversion element may be configured to rotate in various directions.

As illustrated in FIG. 46, according to an aspect of the present disclosure, the first wire 6410, at least a portion of the driving element 6110, the second wire 6420, and the conversion element 6310 may form a closed loop. Accordingly, it is possible to configure the forward drive in which the wire moves and the driving element 6110 is activated according to the activation of the conversion element 6310 as well as the reverse drive in which the driving element 6110 operates by an external force acting on the driving element 6110, and the wire moves accordingly to operate the conversion element 6310.

For example, as illustrated in FIG. 46, a closed loop formed by the first wire 6410, at least a portion of the driving element 6110, the second wire 6420, and the conversion element 6310 may include a plurality of wires, in other words, the first wire and the second wire, for moving the driving element 6110 in different directions. In a basic state in which no control operation is performed, the tensions of the first wire and the second wire may be set to be substantially the same, with a difference within a predetermined threshold range. The tensions of the first wire and the second wire may be offset from each other, so that the driving element 6110 may be maintained in a fixed state.

In other words, one driving element may be driven, for example, through two wires, and may be configured to pull one wire when moving the driving element in one direction, and pull the other wire when the driving element is moved in the other direction. Herein, two wires for manipulating one driving element may form one loop, and such a loop may be assembled to have a certain pre-tension in the initial state.

According to an aspect of the present disclosure, the reverse drive of the surgical instrument may be performed in a state where the power transmission between the conversion element and the actuator is decoupled. Herein, even in a state where the power transmission between the conversion element and the actuator is decoupled, the tension of the loop including the aforementioned wires may not be changed. For example, even when the actuator such as a motor is decoupled from the conversion element, the end tool may be configured so as not to move unless an external force (including gravity) is applied to the end tool.

Figure 48:
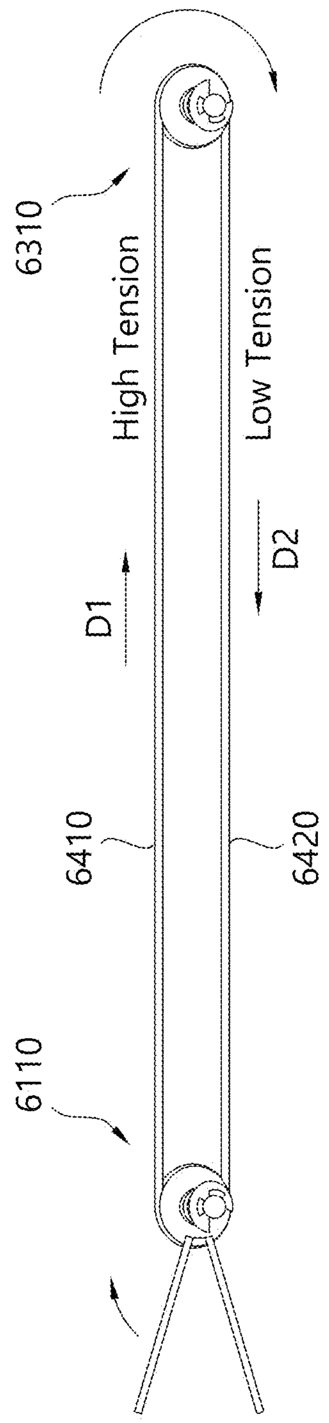
FIG. 48 illustrates a tension change of the wire according to a forward drive of the closed loop of FIG. 46.
Figure 49:
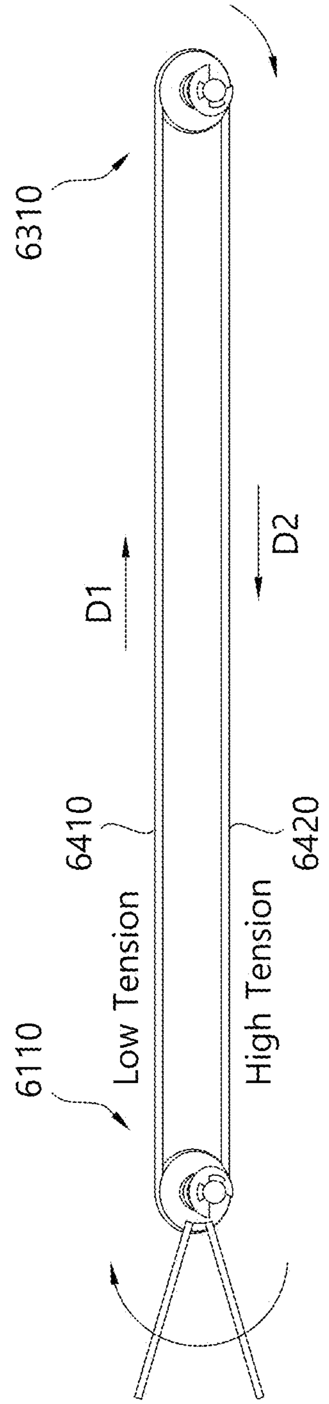
FIG. 49 illustrates a tension change of the wire according to a reverse drive of the closed loop of FIG. 46.

FIG. 48 illustrates a tension change of the wire according to a forward drive of the closed loop of FIG. 46. FIG. 49 illustrates a tension change of the wire according to a reverse drive of the closed loop of FIG. 46. As illustrated in FIGS. 48 and 49, the tension of the first wire 6410 or the second wire 6420 may be changed by operating the surgical instrument. For example, when the driving element operates in the first direction according to the forward drive, the tension of the first wire increases and the tension of the second wire decreases, and when the driving element operates in the first direction according to the reverse drive, the tension of the first wire decreases and the tension of the second wire increases.

Non-limitingly, but more specifically, as illustrated in FIG. 48, upon examining the tension change according to the forward drive, when the conversion element 6310 rotates in the first direction (clockwise in FIG. 48) for the forward drive, the first wire is pulled in a backward direction (D1), so that the tension of the first wire 6410 increases. As the first wire is pulled in the backward direction (D1), the driving element 6110 also activates in the first direction (clockwise in FIG. 48). Herein, when the conversion element 6310 rotates in the first direction (clockwise in FIG. 48), the tension of the second wire 6420 rather decreases. When the activation of the conversion element 6310 is stopped, this tension change is restored to the original state by the tensions of the first wire and the second wire being offset, so that the tensions of the first wire and the second wire become balanced.

As illustrated in FIG. 49, upon examining the tension change according to the reverse drive, when the driving element 6110 rotates in the first direction (clockwise in FIG. 49) for the reverse drive, the second wire is pulled in a forward direction (D2), so that the tension of the second wire 6420 increases. As the second wire is pulled in the forward direction (D2), the conversion element 6310 also is activated in the first direction (clockwise in FIG. 48). Herein, when the driving element 6110 rotates in the first direction (clockwise in FIG. 48), the tension of the first wire 6410 rather decreases. When the activation of the driving element 6110 is stopped, this tension change returns to the original state by the tensions of the first wire and the second wire being offset, so that the tensions of the first wire and the second wire become balanced.

In other words, depending on whether the driving element 6110 is reverse driven or forward driven while activating in the same first direction, the change pattern of the tension occurring in the first wire and/or the second wire may be set differently.

Figure 47:
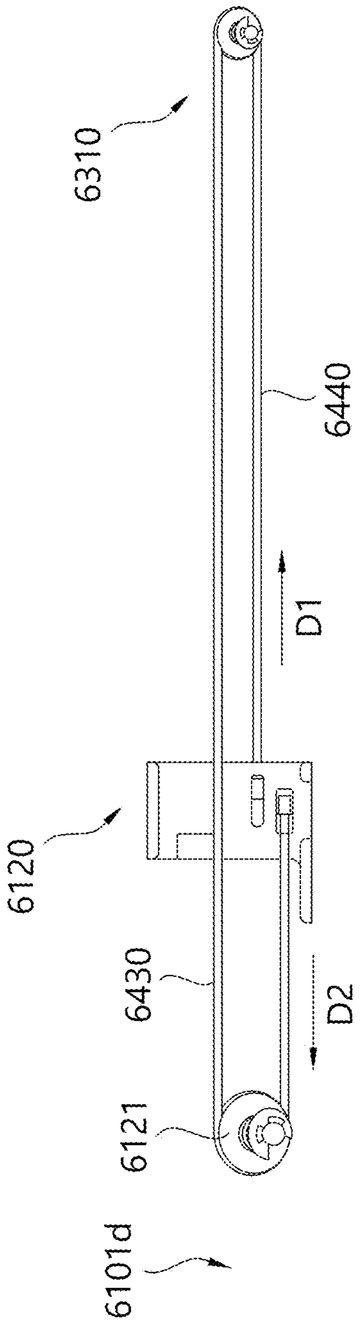
FIG. 47 is an exemplary view of a closed loop by another driving element and wire of the surgical instrument according to an embodiment of the present disclosure.

FIG. 47 is an exemplary view of a closed loop by another driving element and wire of the surgical instrument according to an embodiment of the present disclosure. As illustrated in FIG. 47, according to an aspect of the present disclosure, the straight line movement of the wire 6430, 6440 is controlled based on the rotational movement of the conversion element 6310, and the driving element 6120 may be activated accordingly. As a non-limiting example, the driving element 6120 may be a driving element that performs a linear movement forward toward the distal unit 6101*d* of the end tool or backward away from the distal unit 6101*d* as illustrated in FIG. 47. As described above, such a driving element may be, but is not limited to, the working member of the stapler or the vessel sealer.

Non-limitingly, but more specifically, the surgical instrument according to an embodiment of the present disclosure may be the stapler having the staple cartridge in the end tool, and the driving element may include the working member that moves forward toward a distal unit of the end tool or moves backward away from the distal unit of the end tool according to the linear movement of the wire.

As illustrated in FIG. 47, the wire may include a backward wire 6440 that moves the working member 6120 backward in a direction (D1) away from the distal unit 6101*d* of the end tool, and a forward wire 6430 that moves the working member 6120 forward (D2) toward the distal unit 6101*d* of the end tool. For example, as illustrated in FIG. 47, the forward wire 6430 may be configured to change direction by being wound around a fixed pulley 6121. Herein, the fixed pulley 6121 may be implemented to include at least some of the technical features of the first fixed pulley 3121 or the second fixed pulley 3122 described above with reference to FIGS. 2 to 23.

As a non-limiting example, when the driving element 6120 is the driving element that performs the linear movement such as the working member as illustrated in FIG. 47, the conversion element 6310 may be rotated clockwise to move the driving element 6120 in a forward direction. Accordingly, the portion of the forward wire 6430, before being wound around the fixed pulley 6121, in other words, the upper portion in FIG. 47, may move backward in the direction (D1) away from the distal unit 6101*d* of the end tool, and the portion of the forward wire 6430 connected to the working member after being wound around the fixed pulley 6121, in other words, the lower portion in FIG. 47, may move forward in a direction toward the distal unit 6101*d* of the end tool. In addition, the backward wire 6440 may move forward toward the distal unit 6101*d* of the end tool according to the clockwise rotation of the conversion element 6310. Accordingly, the driving element 6110 may move forward in the direction of the distal unit 6101*d* of the end tool, which may be understood as the linear movement of the working member.

Conversely, the conversion element 6310 may be rotated counterclockwise to move the driving element 6120 in a backward direction. Accordingly, the backward wire 6440 moves backward in the direction (D1) away from the distal unit 6101*d* of the end tool, and the portion of the forward wire 6430 before being wound around the fixed pulley 6121 may move forward toward the distal unit 6101*d* of the end tool. Accordingly, the driving element 6120 may move backward in the direction away from the distal unit 6101*d* of the end tool, which may be understood as the linear movement of the working member.

As described above, in FIGS. 46 to 51, the rotation axis is illustrated in one direction perpendicular to the ground in order to explain the operational relationship of the driving element, the wire, and the conversion element, but it is obvious that the technical idea of the present disclosure is not limited thereto. For example, as described above with reference to FIGS. 1 to 23, the end tool may be provided with the plurality of additional pulleys in addition to the auxiliary pulley, so that the rotation axis of the auxiliary pulley may be configured to rotate in various directions. In addition, as described above with reference to FIGS. 27 to 43, the power transmission unit may also be provided with the plurality of additional pulleys in addition to the driving pulley, so that the rotation axis of the conversion element may be configured to rotate in various directions.

As illustrated in FIG. 47, according to an aspect of the present disclosure, the forward wire 6430, at least a portion of the driving element 6120, the backward wire 6440, and the conversion element 6310 may form a closed loop. Accordingly, it may be configured to enable forward drive in which the wire moves and the driving element 6120 is activated according to the activation of the conversion element 6310, as well as reverse drive in which the driving element 6120 operates by an external force acting on the driving element 6120 and the wire moves accordingly to operate the conversion element 6310.

For example, as illustrated in FIG. 47, a closed loop formed by the forward wire 6430, at least a portion of the driving element 6120, the backward wire 6440, and the conversion element 6310 may include a plurality of wires, in other words, a forward wire and a backward wire, for moving the driving element 6120 in different directions. In the basic state in which no control operation is performed, the tensions of the forward wire and the backward wire have a difference within a predetermined critical range, and may be set to be almost the same. The tension of the forward wire and the backward wire may be offset from each other, so that the driving element 6120 may be maintained in a fixed state.

In other words, one driving element may be driven by, for example, two wires, and may be configured to pull one wire when moving the driving element in one direction, and pull the other wire when moving the driving element in the other direction. Herein, the two wires for manipulating one driving element may form one loop, and such a loop may be assembled to have a constant pre-tension in the initial state.

According to an aspect of the present disclosure, the reverse drive of the surgical instrument may be performed in a state where the power transmission between the conversion element and the actuator is decoupled. Herein, even in a state where the power transmission between the conversion element and the actuator is decoupled, the tension of the loop including the aforementioned wires may not be changed. For example, even when the activator such as the motor is decoupled from the conversion element, the end tool and/or the driving elements provided therein may be configured not to move unless an external force (including gravity) is applied to the end tool.

Figure 50:
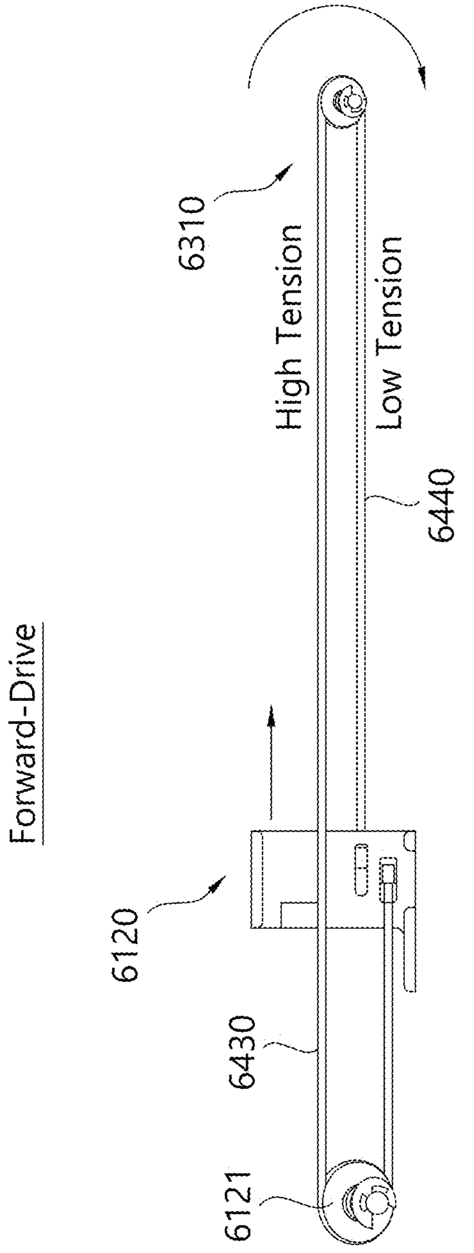
FIG. 50 illustrates a tension change of the wire according to the forward drive of the closed loop of FIG. 47.
Figure 51:
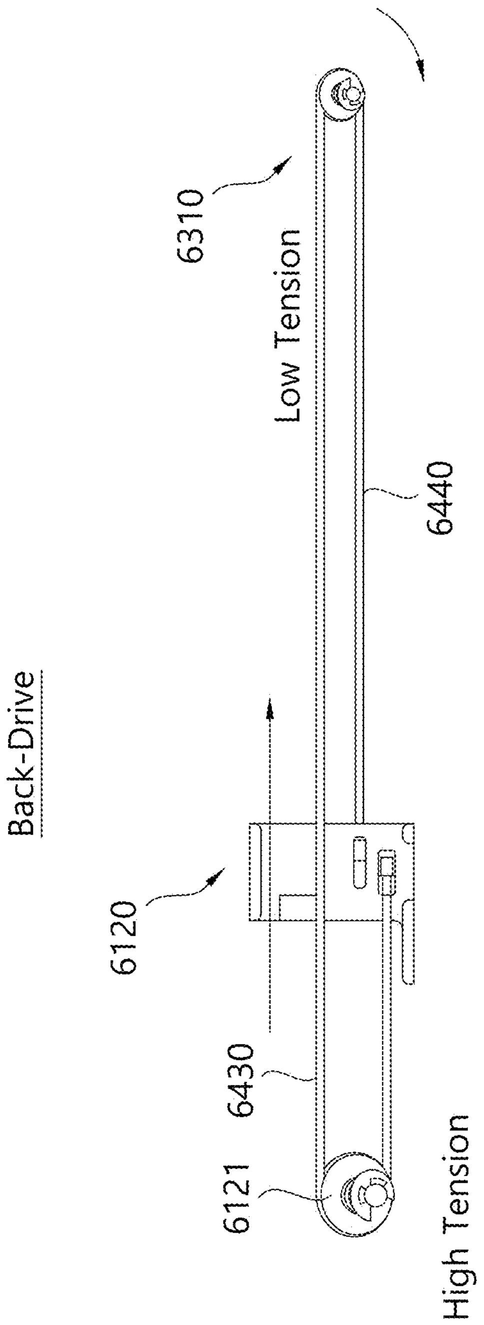
FIG. 51 illustrates a tension change of the wire according to the reverse drive of the closed loop of FIG. 47.

FIG. 50 illustrates a tension change of the wire according to the forward drive of the closed loop of FIG. 47. FIG. 51 illustrates a tension change of the wire according to the reverse drive of the closed loop of FIG. 47. As illustrated in FIGS. 50 and 51, the tension of the forward wire 6430 or the backward wire 6440 may be changed by operating the surgical instrument.

Non-limitingly, but more specifically, as illustrated in FIG. 50, upon examining the tension change according to the forward drive, when the conversion element 6310 rotates in the first direction (clockwise in FIG. 50) for the forward drive, the portion of the forward wire 6430 before being wound around the fixed pulley 6121 is pulled in the backward direction (D1), and the portion of the forward wire after being wound around the fixed pulley 6121 is pulled in the forward direction (D2), so that the tension of the forward wire 6430 increases. The driving element 6120 is activated in the forward direction by the forward wire being pulled. Herein, when the conversion element 6310 rotates in the first direction (clockwise in FIG. 50), the tension of the backward wire 6440 rather decreases. When the activation of the conversion element 6310 is stopped, this tension change returns to the original state by the tensions of the forward wire and the backward wire being offset, so that the tensions of the forward wire and the backward wire become balanced.

As illustrated in FIG. 51, upon examining the tension change according to the reverse drive, when the driving element 6120 is activated in the forward direction for the reverse drive by an external force, the backward wire 6440 is rather pulled in the forward direction, so that the tension increases. As the backward wire 6440 moves forward, the conversion element 6310 is activated in the first direction (clockwise in FIG. 51). When the driving element 6120 is activated in the forward direction for reverse drive by an external force, the tension of the portion of the forward wire 6430 fixed to the working member 6120 after being wound around the fixed pulley 6121, in other words, the lower portion in FIG. 51, is reduced. When the activation of the driving element 6120 is stopped, this tension change is restored to the original state by the tensions of the forward wire and the backward wire being offset, so that the tensions of the forward wire and the backward wire become balanced.

In other words, depending on whether the driving element 6120 is reverse driven or forward driven while activating in the same first direction (for example, forward direction), the change pattern of the tension occurring in the forward wire and/or the backward wire may be set differently.

Hereinafter, although the articulation element or the working member has been described with reference to FIGS. 46 to 51 as an exemplary driving element of an embodiment of the present disclosure, it should be noted that the technical idea of the present disclosure is not limited thereto. It should be noted that the technical features described in connection with the driving element are not limited to a specific driving element such as the articulation element or the working member unless explicitly limited in the present disclosure.

According to an aspect of the present disclosure, the conversion efficiency between the rotational movement of the conversion element 6310 according to the forward drive and the linear movement of the wire may be configured to be substantially the same as the conversion efficiency between the linear movement of the wire and the rotational movement of the conversion element 6310 according to the reverse drive. For example, the amount of change in the degree to which the conversion element 6310 is rotated may be the same depending on the degree to which the wire and/or the driving element in conjunction therewith is activated by the degree to which the conversion element 6310 is rotated and the degree to which the driving element is activated and the wire moves in conjunction therewith. As a non-limiting example, assuming that the actuator is rotated by X to move a specific driving element by Y, when the reverse drive is performed, the actuator may be configured to rotate by X when the driving element is moved by Y. In other words, the ratio of forward and reverse drives may be 1:1. In other words, the efficiency of power transmission when the wire is driven in the forward direction may be the same as the efficiency of power transmission when the wire is driven in the reverse direction.

According to another aspect of the present disclosure, the surgical instrument may include a conversion structure for converting the linear movement of a wire or link structure into the rotational movement. Herein, such a conversion structure may have a pulley shape as exemplified in the drawings, but is not limited thereto. For example, the conversion structure may have a screw shape capable of reverse drive. When the conversion structure has a screw shape, it may have an efficiency of 50% or more for reverse drive, but may be configured to have an efficiency of less than or equal to a first threshold value determined in advance. For example, in order to move the driving element 6120 forward and/or backward performing the linear movement such as the working member, a structure for rotating a screw shaft may be employed. In general, considering the driving efficiency and the operating limit of the surgical instrument, it is advantageous to have high efficiency. However, when the efficiency for forward drive is set to a high level at a normal level, the reverse drive may be configured to be impossible or very inefficient. Accordingly, according to an aspect of the present disclosure, the driving element performing a linear movement may be operated based on a screw, and the straight line movement conversion efficiency of the driving element corresponding to the rotation of the screw may be set to be less than or equal to a first threshold value that is determined in advance. Herein, the first threshold value may be the highest efficiency at which the rotation of the screw according to the straight line movement of the driving element is possible. According to another aspect, considering the reverse drive, the forward efficiency, that is, the efficiency indicating the amount of movement of the working member according to the rotation of the screw, may be set to 50%. Herein, the efficiency of the screw may be determined as follows.

$$\text{Efficiency }\%=[\tan(\text{helix angle})/\tan(\text{helix angle}+\arctan f)]*100$$

In other words, it may be determined according to the angle of the screw thread and the friction coefficient F.

According to an aspect of the present disclosure, the reverse drive may be performed in a state where the power transmission between the conversion element 6310 and the actuator is decoupled. Herein, the actuator may be, for example, a motor provided in the manipulation unit, but is not limited thereto. In other words, according to an aspect of the present disclosure, the surgical instrument may be coupled to the manipulation unit, and may be configured to receive power by coupling the actuator such as the motor provided in the manipulation unit, or a coupling element connected to the actuator to the conversion element 6310 provided in the power transmission unit 6300. The driving element provided in the end tool may be activated based on such power.

Herein, the state in which the power transmission between the conversion element 6310 and the actuator is decoupled may be a state in which the conversion element 6310 and the actuator are physically spaced, but is not limited thereto. For example, it may include all cases in which the power generated in the driving unit may not be transmitted to the end tool, such as a state in which the power of the actuator is not transmitted to the conversion element 6310 due to a failure of the actuator or a discharge of the power supply unit. Accordingly, the surgical instrument according to an embodiment of the present disclosure may be configured so that the actuator is allowed to activate when the surgical instrument is driven in the reverse direction in a state in which the conversion element 6310 and the actuator are not physically spaced. In other words, the actuator may be configured so as not to resist the rotation of the rotation axis of the driving unit by an external force, rather than being rotated by the power. When an external force is applied to at least one of the driving elements for reverse drive, the external force applies a rotational force or a force for the linear movement to the driving element, and this force is transmitted to the conversion element 6310 via a wire or link to rotate the conversion element 6310. When the physical coupling between the conversion element 6310 and the actuator is not decoupled, the rotational force of the conversion element 6310 is transmitted to an axis of the actuator, causing the axis of the actuator to rotate. As a non-limiting example, when the reverse drive is attempted while the actuator and the conversion element 6310 are coupled to each other, the torque applied to the actuator may be measured to perform admittance control to determine whether to allow reverse drive. In addition, according to an aspect, when the actuator is assumed to be a motor, the motor may be equipped with a gear box, and a member for connection with the conversion element 6310 may be provided on the rotation axis of the gear box. Herein, an elastic spring may be provided between the member for connection of the motor and the conversion element 6310 to assist the connection therebetween.

As described above, the surgical instrument according to an embodiment of the present disclosure may be configured to enable reverse drive in which an external force is applied to the driving element of the end tool to manipulate the driving element, and forward drive in which the driving element is manipulated by, for example, actuating the actuator to rotate the conversion element 6310.

According to an aspect of the present disclosure, the surgical instrument may be equipped with a plurality of driving elements. Herein, the driving elements may include at least one of a rotational moving element such as an articulation or a jaw, and a linear moving element such as a working member. Non-limitingly, but more specifically, the end tool 6100 of the surgical instrument 6000 may include the plurality of driving elements including a first driving element and a second driving element. Correspondingly, the power transmission unit 6300 may include a plurality of conversion elements including a first conversion element corresponding to the first driving element and a second conversion element corresponding to the second driving element. In other words, the first conversion element for the operation of the first driving element and the second conversion element for the operation of the second driving element may be provided, respectively. Here, at least one of the first driving element and/or the second driving element may be configured to be capable of reverse drive.

Herein, in response to one of the plurality of driving elements being reversely driven, the conversion element corresponding to the other driving element that is not being reversely driven may also be activated. For example, in response to the first driving element being reversely driven, both the first conversion element and the second conversion element may be activated. Herein, the first conversion element may be directly reversely driven, and the second conversion element may be activated due to a rotational force according to compensation of the wire. In this regard, as exemplarily described with reference to FIGS. 1 to 43, the surgical instrument may include the plurality of driving elements, and wires for driving at least some of the respective driving elements may be shared. In particular, at least some of the rotational moving elements, such as the yaw articulation, the pitch articulation, and the jaw, are required to perform compensation for the wire rather than allowing the movement of one of the elements to be affected by the movement of the other. When the driving elements are designed to compensate for each other in the forward drive, when one of the driving elements is activated in the reverse drive, the other driving element or the corresponding conversion element may be activated by the compensation design of the wire. Accordingly, when the plurality of driving elements are provided in the surgical instrument, the plurality of conversion elements may be activated in response to driving one of the driving elements in the reverse direction.

For example, as described above with reference to FIGS. 46, 48, and 49, the driving element 6110 according to an aspect of the present disclosure may include at least one of the pair of jaws or at least one articulation that rotates within a predetermined angular range according to the linear movement of the wire.

Herein, at least one of the pair of jaws or at least one articulation may be configured to be capable of reverse drive as described above according to an embodiment of the present disclosure. As such, since at least one of the pair of jaws or at least one articulation is configured to be reversely driven, even when the power transmission between the conversion element 6310 and the actuator is decoupled while the driving element is rotated at a predetermined angle with respect to the extension direction of the shaft 6400 inside a surgical target body, the end tool 6100 may be configured to be reversely driven by an end tool insertion guide member and rotated toward the extension direction of the shaft 6400 when removed from the inside of the body. Accordingly, a user of the surgical instrument may safely remove the end tool from a patient body without a separate manipulation, simply by moving the end tool of the surgical instrument away from a patient, without having to convert a laparoscopic surgery to a laparotomic surgery or directly operate the conversion element 6310 using a separate tool such as a wrench. In other words, even when the user does not directly drive the end tool in the reverse direction, the end tool may be straightened and pulled out by the end tool insertion guide member. Herein, the end tool insertion guide member may be, for example, a trocar, but is not limited to such a name, and may refer to any configuration that maintains a cavity in the patient's abdomen and guides the insertion of a surgical instrument into the body, such as a port member or another name.

When the driving element 6110 according to an aspect of the present disclosure, but not limited to, includes at least one of the pair of jaws or at least one articulation that rotate within a predetermined angular range according to the linear movement of the wire, an issue may occur in which the driving element is reversed by an unintended force such as gravity in a state in which reverse drive is allowed. To prevent this, for example, the conversion element 6310 according to an aspect of the present disclosure may employ a structure that intentionally adds rotational friction to the conversion element, such as an elastic body that comes into contact with a rotating cylindrical surface. In addition, as described with reference to FIGS. 1 to 43, for example, the surgical instrument according to an aspect may be provided with at least one auxiliary pulley that is disposed between the conversion element and the driving element to support the wire. A plurality of such auxiliary pulleys may be provided between the actuator and the driving element to adjust the path of the wire. According to another aspect of the present disclosure, a structure that adds rotational friction to at least one of the auxiliary pulleys may be employed.

Figure 52:
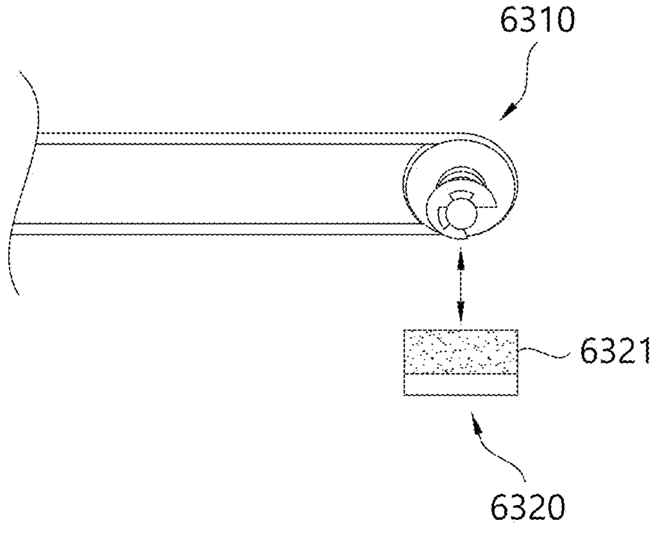
FIG. 52 is an exemplary view of a support element according to an aspect of the present disclosure.

In this regard, FIG. 52 is an exemplary view of a support element according to an aspect of the present disclosure. As illustrated in FIG. 52, the surgical instrument according to an aspect of the present disclosure may further include a support element 6320 that contacts at least one of the conversion element 6310 or the auxiliary pulley to provide frictional force for rotation of at least one of the conversion element 6310 or the auxiliary pulley. The support element 6320 may include, for example, an elastic body 6321 having a frictional force greater than a predetermined threshold value, and the elastic body 6321 may be configured to contact at least one of the conversion element 6310 or the auxiliary pulley. Accordingly, the support element 6320 may be configured to prevent unintentional reverse drive of the driving element due to gravity.

According to an aspect of the present disclosure, when the conversion element 6310 and the actuator are coupled, the support element 6320 may be maintained in a state spaced apart from at least one of the conversion element 6310 or the auxiliary pulley. Accordingly, rotation of the conversion element and/or reduction in actuation efficiency of the driving element due to rotation of the actuator may be prevented.

Alternatively, in response to the decoupling of the conversion element 6310 and the actuator, the support element 6320 may be configured to contact at least one of the conversion element 6310 or the auxiliary pulley to prevent unintentional reverse drive. Herein, in an aspect, the decoupling of the conversion element 6310 and the actuator may mean physical decoupling, which may be sensed by any known component, such as a protruding hinge or a spring, to control movement of the support element. In addition, in another aspect, the decoupling of the conversion element 6310 and the actuator may include a non-physical event, such as the actuator ceasing to operate, which may be sensed by any known component, such as an electrical sensor for the actuator, to control movement of the support element.

As described above, the driving element 6120 according to an aspect of the present disclosure may be the working member 6120 that performs linear movements such as forward and/or backward, as described above with reference to FIGS. 47, 50, and 51. It is noted that such the working member 6120 may borrow at least some of the technical features of the working member as described with reference to FIGS. 1 to 43, for example.

For example, the surgical instrument according to an embodiment of the present disclosure may be the stapler, and the driving element 6120 configured to be capable of reverse drive may be the working member 6120. Conventionally, the working member of such a stapler is not designed to be capable of reverse drive, whereas the stapler according to an aspect of the present disclosure may include the working member 6120 configured to be capable of reverse drive.

Figure 53:
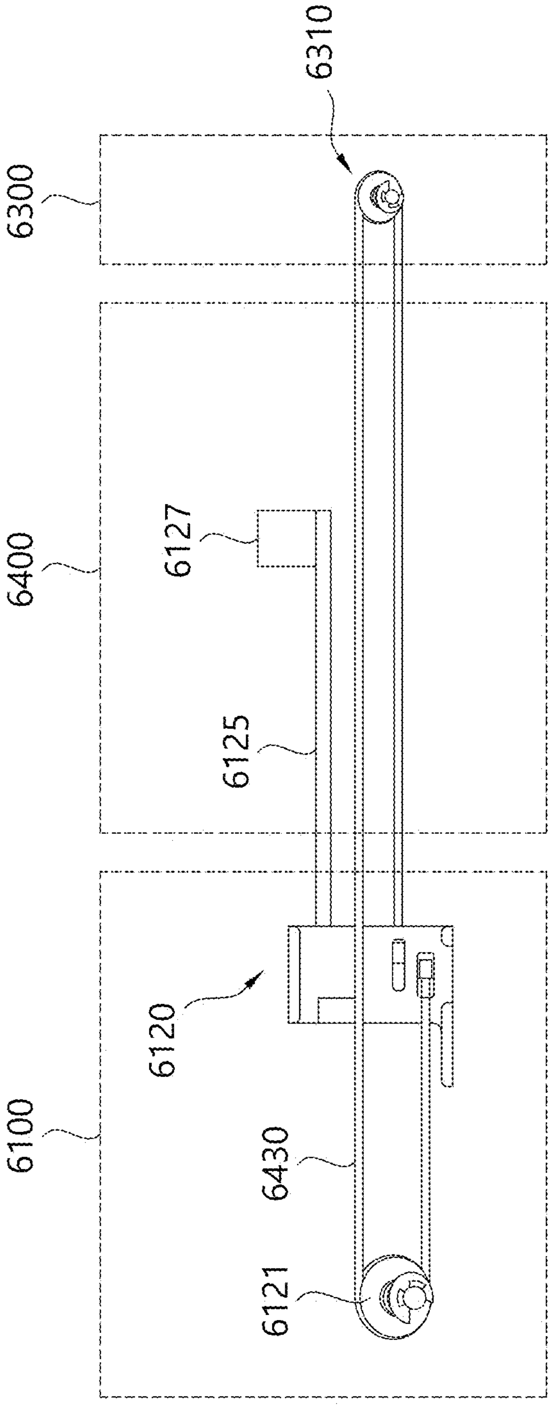
FIG. 53 is an exemplary view of a protruding member according to an aspect of the present disclosure.

In this regard, FIG. 53 is an exemplary view of a protruding member according to an aspect of the present disclosure. The working member according to an aspect of the present disclosure may further include a protruding member connected to the working member and protruding outwardly of the surgical instrument for reverse drive of the working member. For example, such a working member may be the first clamp 3146 or the second clamp 3147 described above with reference to FIGS. 10 to 12. Such clamps may protrude outwardly of each of the pair of jaws, thereby pressurizing the pair of jaws toward each other as the working member moves forward or backward. Hence, a more stable stapling work and gripping of body tissue may be performed. Moreover, since the clamps protrude outwardly of the pair of jaws, a user may perform reverse drive of the working member by applying an external force to at least one of the clamps.

In addition, according to another aspect of the present disclosure, as illustrated in FIG. 53, the protruding member 6127 may be configured to be disposed further from the distal unit of the end tool 6100 than the working member 6120 so that the end tool 6100 may be located outside the body while being inserted into a surgical target body. To this end, the protruding member 6127 may be connected to the working member 6120 via a flexible extension member 6125. Accordingly, the protruding member 6400 may be located outside the body of a patient while the end tool 6100 is located inside the body of a patient while allowing the articulation element provided to the end tool to perform rotational movement. Even when the driving unit and the conversion element 6310 are decoupled while the end tool has gripped at least a portion of the organ tissue inside the body of the patient, a user may apply an external force to the protruding member 6127 located outside the body to take out the gripped body tissue.

Hereinbefore, the embodiments of the present disclosure have been described with reference to the accompanying drawing, but the scope of protection of the present disclosure should not be construed as being limited to the drawings or embodiments. It will be understood by those skilled in the technical field that the present disclosure allows various modifications and variations without departing from the scope and spirit of the present disclosure as described in the claims below.

While the present disclosure has been described on the basis of a series of functional blocks, it is not limited by the embodiments described above and the accompanying drawings and it will be apparent to those skilled in the art that various substitutions, modifications and variations may be made without departing from the scope of the present disclosure.

The combination of the above-described embodiments is not limited to the above-described embodiments, and various forms of combination in addition to the above-described embodiments may be provided according to implementation and/or necessity.

In the above-described embodiments, the methods are described on the basis of a flowchart as a series of operations or blocks, but the present disclosure is not limited to the order of the operations, and some operations may occur in different orders or at the same time unlike those described above. It will also be understood by those skilled in the art that the operations shown in the flowchart are not exclusive, and other operations may be included, or one or more operations in the flowchart may be omitted without affecting the scope of the present disclosure.

The above-described embodiments include examples of various aspects. While it is not possible to describe every possible combination for expressing various aspects, one of ordinary skill in the art will recognize that other combinations are possible. Accordingly, it is intended that the present disclosure include all alternatives, modifications and variations that fall within the scope of the following claims.

What is claimed is:

1. A surgical instrument capable of reverse drive, the instrument comprising:

an end tool having at least one driving element activated by a wire;

a power transmission unit that controls a linear movement of the wire based on a rotational movement of a conversion element in accordance with power from an actuator; and a shaft connecting the end tool and the power transmission unit, and being configured so that both forward drive in which the driving element is activated according to activation of the actuator and the reverse drive in which the conversion element is activated according to activation of the driving element due to an external force are possible, wherein the wire comprises:

a first wire that moves backward in a direction away from a distal unit of the end tool to activate the driving element in a first direction; and a second wire that moves forward toward the distal unit of the end tool to activate the driving element in the first direction, wherein the first wire, at least a portion of the driving element, the second wire, and the conversion element form a closed loop, and wherein:

when the driving element is activated in the first direction according to the forward drive, tension of the first wire increases and tension of the second wire decreases; and when the driving element is activated in the first direction according to the reverse drive, the tension of the first wire decreases and the tension of the second wire increases.

2. The instrument of claim 1, wherein conversion efficiency between the rotational movement of the conversion element and the linear movement of the wire according to the forward drive is the same as the conversion efficiency between the linear movement of the wire and the rotational movement of the conversion element according to the reverse drive.

3. The instrument of claim 1, wherein the reverse drive is performed in a state where power transmission between the conversion element and the actuator is decoupled.

4. The instrument of claim 3, wherein the state where the power transmission is decoupled comprises at least one of:

a state where the conversion element and the actuator are physically spaced; or a state where the power of the actuator is not transmitted to the conversion element due to a failure of the actuator or a discharge of a power supply unit.

5. The instrument of claim 4, wherein the actuator is activated by the surgical instrument being driven in a reverse direction in a state where the conversion element and the actuator are not physically spaced apart from each other.

6. The instrument of claim 1, wherein:

the end tool comprises a plurality of driving elements comprising a first driving element and a second driving element; and the power transmission unit comprises a plurality of conversion elements comprising a first conversion element corresponding to the first driving element and a second conversion element corresponding to the second driving element, wherein the first conversion element and the second conversion element are activated in response to one of the plurality of driving elements being driven in a reverse direction.

7. The instrument of claim 1, further comprising at least one auxiliary pulley disposed between the conversion element and the driving element to support the wire.

8. The instrument of claim 7, further comprising a support element that contacts at least one of the conversion element or the auxiliary pulley to provide a frictional force for rotation of at least one of the conversion element or the auxiliary pulley.

9. The instrument of claim 8, wherein the support element is configured to prevent unintentional reverse drive of the driving element due to gravity.

10. The instrument of claim 8, wherein:

in a state where the conversion element and the actuator are coupled, the support element is spaced apart from at least one of the conversion element or the auxiliary pulley; and in response to decoupling of the conversion element and the actuator, the support element is configured to contact at least one of the conversion element or the auxiliary pulley.

11. The instrument of claim 1, wherein the driving element comprises at least one articulation or at least one of a pair of jaws that rotate within a predetermined angular range according to the linear movement of the wire.

12. The instrument of claim 11, wherein at least one of the at least one articulation or the pair of jaws is configured to rotate toward an extension direction of the shaft by being driven in a reverse direction by an end tool insertion guide member when the end tool is removed from inside of a body, even when power transmission between the conversion element and the actuator is decoupled while being rotated at a predetermined angle with respect to the extension direction of the shaft inside the body.

13. The instrument of claim 1, wherein:

the surgical instrument is a stapler having a staple cartridge in the end tool; and the driving element comprises a working member that moves forward toward a distal unit of the end tool or moves backward away from the distal unit of the end tool according to the linear movement of the wire.

14. The instrument of claim 13, wherein the wire comprises:

a backward wire that moves the working member backward away from the distal unit of the end tool; and a forward wire that moves the working member forward toward the distal unit of the end tool.

15. The instrument of claim 13, further comprising a protruding member connected to the working member for the reverse drive of the working member and protruding outward from the surgical instrument.

16. The instrument of claim 15, wherein the protruding member is configured to be disposed farther from the distal unit of the end tool than the working member so that the protruding member is located outside a body while the end tool is inserted into the body, and is connected to the working member through a flexible extension member.

17. The instrument of claim 1, wherein the surgical instrument is a hand-held device and further comprises a manipulation unit having the actuator and a handle unit and coupled to the power transmission unit.

* * * * *